(12) United States Patent
Levine et al.

(10) Patent No.: US 7,837,643 B2
(45) Date of Patent: Nov. 23, 2010

(54) METHODS AND DEVICES FOR PLACING A GASTROINTESTINAL SLEEVE

(75) Inventors: Andy H. Levine, Newton, MA (US); David A. Melanson, Hudson, NH (US); Ronald B. Lamport, Pelham, NH (US)

(73) Assignee: GI Dynamics, Inc., Lexington, MA (US)

( * ) Notice: Subject to any disclaimer, the term of this patent is extended or adjusted under 35 U.S.C. 154(b) by 1357 days.

(21) Appl. No.: 11/057,861

(22) Filed: Feb. 14, 2005

(65) Prior Publication Data

US 2006/0009858 A1    Jan. 12, 2006

Related U.S. Application Data

(60) Provisional application No. 60/586,521, filed on Jul. 9, 2004, provisional application No. 60/610,614, filed on Sep. 15, 2004.

(51) Int. Cl.
*A61M 5/00* (2006.01)
*A61F 2/04* (2006.01)

(52) U.S. Cl. .................. 604/8; 623/23.7; 623/23.65

(58) Field of Classification Search ............ 604/8; 623/23.65
See application file for complete search history.

(56) References Cited

U.S. PATENT DOCUMENTS

| | | | |
|---|---|---|---|
| 1,899,781 A | 2/1933 | Twiss | |
| 2,464,933 A | 3/1949 | Kaslow | |
| 3,780,740 A | 12/1973 | Rhea | |
| 4,133,315 A | 1/1979 | Berman et al. | |
| 4,134,405 A | 1/1979 | Smit | |
| 4,265,694 A | 5/1981 | Boretos et al. | |
| 4,270,542 A | 6/1981 | Plumley | |
| 4,279,251 A | 7/1981 | Rüsch | |
| 4,315,509 A | 2/1982 | Smit | |
| 4,341,218 A | 7/1982 | Ü | |
| 4,403,604 A | 9/1983 | Wilkinson et al. | |
| 4,416,267 A | 11/1983 | Garren et al. | |
| 4,501,264 A | 2/1985 | Rockey | |
| 4,580,568 A | 4/1986 | Gianturco | |

(Continued)

FOREIGN PATENT DOCUMENTS

DE    33 26 061 A1    2/1984

(Continued)

OTHER PUBLICATIONS

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):Jan. 1-11, 2004.

(Continued)

*Primary Examiner*—Tatyana Zalukaeva
*Assistant Examiner*—Susan Su
(74) *Attorney, Agent, or Firm*—Hamilton, Brook, Smith & Reynolds, P.C.

(57) ABSTRACT

Methods and systems for delivering or placing a gastrointestinal implant device into a mammal. The gastrointestinal implant device can be used to limit absorption of food products in specific parts of the digestive system and can include a gastrointestinal sleeve having an anchor portion and a barrier or sleeve portion. The methods include endoluminal delivery of the device.

25 Claims, 52 Drawing Sheets

U.S. PATENT DOCUMENTS

| | | | |
|---|---|---|---|
| 4,607,618 A | 8/1986 | Angelchik | |
| 4,617,932 A | 10/1986 | Kornberg | |
| 4,641,653 A | 2/1987 | Rockey | |
| 4,648,383 A | 3/1987 | Angelchik | |
| 4,763,653 A | 8/1988 | Rockey | |
| 4,768,507 A | 9/1988 | Fischell et al. | |
| 4,823,808 A | 4/1989 | Clegg et al. | |
| 4,846,836 A | 7/1989 | Reich | |
| 4,878,905 A | 11/1989 | Blass | |
| 4,905,693 A | 3/1990 | Ravo | |
| 4,913,141 A | 4/1990 | Hillstead | |
| 5,035,706 A | 7/1991 | Giantureo et al. | |
| 5,037,387 A | 8/1991 | Quinn et al. | |
| 5,041,126 A | 8/1991 | Gianturco | |
| 5,057,091 A | 10/1991 | Andersen | |
| 5,059,166 A | 10/1991 | Fischell et al. | |
| 5,104,399 A | 4/1992 | Lazarus | |
| 5,135,516 A | 8/1992 | Sahatjian et al. | |
| 5,139,478 A * | 8/1992 | Koninckx et al. | 604/26 |
| 5,152,756 A | 10/1992 | Quinn et al. | |
| 5,176,617 A | 1/1993 | Fischell et al. | |
| 5,190,561 A | 3/1993 | Graber | |
| 5,226,429 A | 7/1993 | Kuzmak | |
| 5,236,423 A | 8/1993 | Mix et al. | |
| 5,254,133 A | 10/1993 | Seid | |
| 5,279,553 A | 1/1994 | Winkler et al. | |
| 5,282,824 A | 2/1994 | Gianturco | |
| 5,290,294 A | 3/1994 | Cox et al. | |
| 5,306,300 A | 4/1994 | Berry | |
| 5,314,444 A | 5/1994 | Gianturco | |
| 5,314,472 A | 5/1994 | Fontaine | |
| 5,314,473 A | 5/1994 | Godin | |
| 5,318,530 A | 6/1994 | Nelson, Jr. | |
| 5,322,501 A | 6/1994 | Mahmud-Durrani | |
| 5,330,500 A | 7/1994 | Song | |
| 5,364,353 A | 11/1994 | Corfitsen et al. | |
| 5,387,235 A | 2/1995 | Chuter | |
| 5,389,090 A | 2/1995 | Fischell et al. | |
| 5,401,241 A | 3/1995 | Delany | |
| 5,405,378 A | 4/1995 | Strecker | |
| 5,417,697 A | 5/1995 | Wilk et al. | |
| 5,423,851 A | 6/1995 | Samuels | |
| 5,443,498 A | 8/1995 | Fontaine | |
| 5,456,713 A | 10/1995 | Chuter | |
| 5,480,423 A | 1/1996 | Ravenscroft et al. | |
| 5,492,530 A | 2/1996 | Fischell et al. | |
| 5,507,767 A | 4/1996 | Maeda et al. | |
| 5,507,771 A | 4/1996 | Gianturco | |
| 5,562,697 A | 10/1996 | Christiansen | |
| 5,569,219 A | 10/1996 | Hakki et al. | |
| 5,605,530 A | 2/1997 | Fischell et al. | |
| 5,607,442 A | 3/1997 | Fischell et al. | |
| 5,611,787 A | 3/1997 | Demeter et al. | |
| 5,620,763 A | 4/1997 | House et al. | |
| 5,624,430 A | 4/1997 | Eton et al. | |
| 5,630,797 A | 5/1997 | Diedrich et al. | |
| 5,634,928 A | 6/1997 | Fischell et al. | |
| 5,639,274 A | 6/1997 | Fischell et al. | |
| 5,643,312 A | 7/1997 | Fischell et al. | |
| 5,662,585 A * | 9/1997 | Willis et al. | 600/104 |
| 5,662,713 A | 9/1997 | Andersen et al. | |
| 5,665,064 A | 9/1997 | Bodicky et al. | |
| 5,669,932 A | 9/1997 | Fischell et al. | |
| 5,683,451 A * | 11/1997 | Lenker et al. | 623/1.11 |
| 5,690,642 A | 11/1997 | Osborne et al. | |
| 5,693,084 A | 12/1997 | Chuter | |
| 5,695,516 A | 12/1997 | Fischell et al. | |
| 5,697,971 A | 12/1997 | Fischell et al. | |
| 5,713,948 A | 2/1998 | Uflacker | |
| 5,715,832 A | 2/1998 | Koblish et al. | |
| 5,718,973 A | 2/1998 | Lewis et al. | |
| 5,720,776 A | 2/1998 | Chuter et al. | |
| 5,722,984 A | 3/1998 | Fischell et al. | |
| 5,730,698 A | 3/1998 | Fischell et al. | |
| 5,733,325 A | 3/1998 | Robinson et al. | |
| 5,735,859 A | 4/1998 | Fischell et al. | |
| 5,735,892 A | 4/1998 | Myers et al. | |
| 5,743,874 A | 4/1998 | Fischell et al. | |
| 5,746,692 A * | 5/1998 | Bacich et al. | 600/104 |
| 5,749,825 A | 5/1998 | Fischell et al. | |
| 5,755,777 A | 5/1998 | Chuter | |
| 5,759,174 A | 6/1998 | Fischell et al. | |
| 5,769,887 A * | 6/1998 | Brown et al. | 623/1.23 |
| 5,776,186 A | 7/1998 | Uflacker | |
| 5,792,144 A | 8/1998 | Fischell et al. | |
| 5,792,172 A | 8/1998 | Fischell et al. | |
| 5,800,381 A * | 9/1998 | Ognier | 604/26 |
| 5,800,456 A | 9/1998 | Maeda et al. | |
| 5,800,526 A | 9/1998 | Anderson et al. | |
| 5,820,584 A | 10/1998 | Crabb | |
| 5,824,071 A * | 10/1998 | Nelson et al. | 606/194 |
| 5,830,229 A | 11/1998 | Konya et al. | |
| 5,833,707 A | 11/1998 | McIntyre et al. | |
| 5,840,009 A | 11/1998 | Fischell et al. | |
| 5,843,164 A | 12/1998 | Frantzen et al. | |
| 5,876,445 A | 3/1999 | Andersen et al. | |
| 5,879,282 A | 3/1999 | Fischell et al. | |
| 5,879,370 A | 3/1999 | Fischell et al. | |
| 5,895,391 A | 4/1999 | Farnholtz | |
| 5,910,145 A | 6/1999 | Fischell et al. | |
| 5,913,895 A | 6/1999 | Burpee et al. | |
| 5,919,225 A | 7/1999 | Lau et al. | |
| 5,925,063 A | 7/1999 | Khosravi | |
| 5,963,620 A | 10/1999 | Frankel et al. | |
| 5,964,771 A | 10/1999 | Beyar et al. | |
| 5,976,153 A | 11/1999 | Fischell et al. | |
| 6,013,019 A | 1/2000 | Fischell et al. | |
| 6,025,044 A | 2/2000 | Campbell et al. | |
| 6,027,508 A | 2/2000 | Ren et al. | |
| 6,086,604 A | 7/2000 | Fischell et al. | |
| 6,099,552 A | 8/2000 | Adams | |
| 6,102,887 A | 8/2000 | Altman | |
| 6,113,607 A | 9/2000 | Lau et al. | |
| 6,120,533 A | 9/2000 | Fischell | |
| 6,132,471 A | 10/2000 | Johlin, Jr. | |
| 6,146,323 A | 11/2000 | Fischell | |
| 6,152,956 A | 11/2000 | Pierce | |
| 6,179,868 B1 | 1/2001 | Burpee et al. | |
| 6,187,016 B1 | 2/2001 | Hedges et al. | |
| 6,190,403 B1 | 2/2001 | Fischell et al. | |
| 6,200,336 B1 | 3/2001 | Pavcnik et al. | |
| 6,221,043 B1 | 4/2001 | Fischell et al. | |
| 6,241,738 B1 | 6/2001 | Dereume | |
| 6,241,757 B1 | 6/2001 | An et al. | |
| 6,251,132 B1 | 6/2001 | Ravenscroft et al. | |
| 6,270,521 B1 | 8/2001 | Fischell et al. | |
| 6,293,960 B1 | 9/2001 | Ken | |
| 6,302,891 B1 | 10/2001 | Nadal | |
| 6,302,917 B1 | 10/2001 | Dua et al. | |
| 6,315,708 B1 | 11/2001 | Salmon et al. | |
| 6,322,538 B1 | 11/2001 | Elbert et al. | |
| 6,331,190 B1 | 12/2001 | Shokoohi et al. | |
| 6,332,877 B1 | 12/2001 | Michels | |
| 6,356,782 B1 | 3/2002 | Sirimanne et al. | |
| 6,375,660 B1 | 4/2002 | Fischell et al. | |
| 6,387,114 B2 | 5/2002 | Adams | |
| 6,406,792 B1 | 6/2002 | Briquet et al. | |
| 6,428,558 B1 | 8/2002 | Jones et al. | |
| 6,450,989 B2 | 9/2002 | Dubrul et al. | |
| 6,458,074 B1 | 10/2002 | Matsui et al. | |
| 6,485,409 B1 | 11/2002 | Voloshin et al. | |
| 6,485,515 B2 | 11/2002 | Strecker | |
| 6,508,833 B2 | 1/2003 | Pavcnik et al. | |
| 6,520,985 B1 | 2/2003 | Burpee et al. | |

| | | |
|---|---|---|
| 6,524,336 B1 | 2/2003 | Papazolgou et al. |
| 6,530,951 B1 | 3/2003 | Bates et al. |
| 6,537,247 B2 | 3/2003 | Shannon |
| 6,540,775 B1 | 4/2003 | Fischell et al. |
| 6,540,789 B1 | 4/2003 | Silverman et al. |
| 6,544,291 B2 | 4/2003 | Taylor |
| 6,547,817 B1 | 4/2003 | Fischell et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,569,181 B1 | 5/2003 | Burns |
| 6,589,213 B2 | 7/2003 | Reydel |
| 6,589,275 B1 | 7/2003 | Ivancev et al. |
| 6,623,518 B2 | 9/2003 | Thompson et al. |
| 6,635,069 B1 | 10/2003 | Teoh et al. |
| 6,635,079 B2 | 10/2003 | Unsworth et al. |
| 6,645,239 B1 | 11/2003 | Park et al. |
| 6,652,555 B1 | 11/2003 | VanTassel et al. |
| 6,656,194 B1 | 12/2003 | Gannoe et al. |
| 6,669,722 B2 | 12/2003 | Chen et al. |
| 6,675,809 B2 | 1/2004 | Stack et al. |
| 6,676,692 B2 | 1/2004 | Rabkin et al. |
| 6,695,875 B2 * | 2/2004 | Stelter et al. ............... 623/1.13 |
| 6,699,263 B2 | 3/2004 | Cope |
| 6,699,278 B2 | 3/2004 | Fischell et al. |
| 6,706,061 B1 | 3/2004 | Fischell et al. |
| 6,716,240 B2 | 4/2004 | Fischell et al. |
| 6,736,840 B2 | 5/2004 | Fischell et al. |
| 6,740,121 B2 | 5/2004 | Geitz |
| 6,755,869 B2 | 6/2004 | Geitz |
| 6,773,440 B2 | 8/2004 | Gannoe et al. |
| 6,776,791 B1 | 8/2004 | Stallings et al. |
| 6,821,291 B2 | 11/2004 | Bolea et al. |
| 6,845,776 B2 | 1/2005 | Stack et al. |
| 6,849,087 B1 * | 2/2005 | Chuter ...................... 623/1.23 |
| 6,936,065 B2 | 8/2005 | Khan et al. |
| 7,011,673 B2 | 3/2006 | Fischell et al. |
| 7,025,791 B2 | 4/2006 | Levine et al. |
| 7,037,327 B2 | 5/2006 | Salmon et al. |
| 7,037,344 B2 | 5/2006 | Kagan et al. |
| 7,054,690 B2 * | 5/2006 | Imran .......................... 607/40 |
| 7,111,627 B2 * | 9/2006 | Stack et al. .................. 128/898 |
| 7,122,058 B2 | 10/2006 | Levine et al. |
| 7,146,984 B2 | 12/2006 | Stack et al. |
| 7,152,607 B2 | 12/2006 | Stack et al. |
| 7,160,312 B2 | 1/2007 | Saadat |
| 7,211,114 B2 | 5/2007 | Bessler et |
| 7,220,237 B2 | 5/2007 | Gannoe et al. |
| 7,220,284 B2 | 5/2007 | Kagan et al. |
| 7,229,428 B2 * | 6/2007 | Gannoe et al. ................. 604/8 |
| 7,267,694 B2 | 9/2007 | Levine et al. |
| 7,314,489 B2 | 1/2008 | McKenna et al. |
| 7,316,716 B2 * | 1/2008 | Egan ........................ 623/23.65 |
| 7,329,285 B2 | 2/2008 | Levine et al. |
| 7,338,520 B2 | 3/2008 | Bailey et al. |
| 7,347,875 B2 | 3/2008 | Levine et al. |
| 7,354,454 B2 | 4/2008 | Stack et al. |
| 7,476,256 B2 | 1/2009 | Meade et al. |
| 7,488,344 B2 * | 2/2009 | Hartley et al. ............... 623/1.23 |
| 2001/0020190 A1 | 9/2001 | Taylor |
| 2002/0032487 A1 | 3/2002 | Dua et al. |
| 2002/0091439 A1 | 7/2002 | Baker et al. |
| 2002/0120277 A1 | 8/2002 | Hauschild et al. |
| 2002/0143387 A1 | 10/2002 | Soetikno et al. |
| 2002/0147489 A1 | 10/2002 | Hong et al. |
| 2002/0151953 A1 | 10/2002 | Chobotov et al. |
| 2002/0183768 A1 | 12/2002 | Deem et al. |
| 2002/0183786 A1 | 12/2002 | Girton |
| 2002/0188344 A1 | 12/2002 | Bolea et al. |
| 2002/0193828 A1 | 12/2002 | Griffin et al. |
| 2003/0032941 A1 | 2/2003 | Boyle et al. |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0233140 A1 | 12/2003 | Hartley et al. |
| 2004/0024386 A1 | 2/2004 | Deem et al. |
| 2004/0039452 A1 | 2/2004 | Bessler |
| 2004/0044357 A1 | 3/2004 | Gannoe et al. |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0098079 A1 | 5/2004 | Hartley et al. |
| 2004/0107004 A1 | 6/2004 | Levine et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0133147 A1 | 7/2004 | Woo |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172141 A1 | 9/2004 | Stack et al. |
| 2004/0172142 A1 | 9/2004 | Stack et al. |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0220682 A1 | 11/2004 | Levine et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0060017 A1 | 3/2005 | Fischell et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096750 A1 | 5/2005 | Kagan et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0267533 A1 | 12/2005 | Gertner |
| 2006/0009858 A1 | 1/2006 | Levine et al. |
| 2006/0064120 A1 | 3/2006 | Levine et al. |
| 2006/0106332 A1 | 5/2006 | Knudson et al. |

| Publication | Date | Inventor |
|---|---|---|
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2007/0005147 A1 | 1/2007 | Levine et al. |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083271 A1 | 4/2007 | Levine et al. |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0208357 A1 | 8/2008 | Melanson et al. |
| 2008/0223476 A1 | 9/2008 | Stinson |
| 2008/0234834 A1 | 9/2008 | Meade et al. |

FOREIGN PATENT DOCUMENTS

| | | |
|---|---|---|
| EP | 0423916 B1 | 4/1991 |
| EP | 0 480 667 B1 | 4/1992 |
| EP | 0 278 937 B1 | 10/1993 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| JP | 04212348 | 8/1992 |
| WO | WO 92/06734 A1 | 4/1992 |
| WO | WO 95/05132 | 2/1995 |
| WO | WO 97/03624 A1 | 2/1997 |
| WO | WO 98/22045 A | 5/1998 |
| WO | WO 99/23953 | 5/1999 |
| WO | WO 99/44536 A | 9/1999 |
| WO | WO 00/12027 A1 | 3/2000 |
| WO | WO 00/32137 | 6/2000 |
| WO | WO 00/42949 A2 | 7/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |
| WO | WO 02/096327 A2 | 12/2002 |
| WO | WO 03/017882 A2 | 3/2003 |
| WO | WO 03/086246 A1 | 10/2003 |
| WO | WO 03/086360 A1 | 10/2003 |
| WO | WO 03/094785 A1 | 11/2003 |
| WO | WO 2004/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/087014 A2 | 10/2004 |
| WO | WO 2004/087233 A2 | 10/2004 |
| WO | WO 2005/011533 A1 | 2/2005 |
| WO | WO 2005/082296 A1 | 9/2005 |
| WO | WO 2005/110280 A2 | 11/2005 |
| WO | WO 2005/120363 A1 | 12/2005 |
| WO | WO 2006/016894 A1 | 2/2006 |
| WO | WO 2006/088578 A1 | 8/2006 |

OTHER PUBLICATIONS

Bethge, N., et al., "Human Tissue Responses to Metal Stents Implanted In Vivo for the Palliation of Malignant Stenoses," *Gastrointestinal Endoscopy*, 43(6): 596-602 (1996).
Binkert, C.A., et al., "Benign and Malignant Stenoses of the Stomach and Duodenum: Treatment with Self-Expanding Metallic Endoprostheses," *Radiology* 199(2): 335-338 (1996).
Cwikiel, W., et al., "Self-Expanding Stent in the Treatment of Benign Esophageal Strictures: Experimental Study in Pigs and Presentation of Clinical Cases," *Radiology*, 187(3): 667-671 (1993).
Feretis, C., et al., "Palliation of Malignant Gastric Outlet Obstruction with Self-Expanding Metal Stents," *Endoscopy* 28: 225-228 (1996).
Park, B.P., et al., "Malignant Obstruction of Gastric Outlet and Duodendum: Palliation with Flexible Covered Metallic Stents," *Radiology* 219(3) 679-683 (2001).
Dormann, A.J., et al., "Self-Expanding Metallic Stents for Continuous Dilatation of Benign Stenoses in Gastrointestinal tract- First Results of Long-Term Follow-Up in Interim Stent Application in Pyloric and Colonic Obstructions," *Z Gastroenteral* 39: 957-960 (2001).
Sandha, G.S., et al., "Expandable Metal Stents for Benign Esophageal Obstruction," *Gastrointestinal Endoscopy Clinics of North America*, 9: (3) 437-446 (1999).
Yates, III, M.R., et al., "Palliation of Malignant Gastric and Small Intestinal Strictures with Self-Expandable Metal Stents," *Endoscopy* 30: 266-272 (1998).
Pories, W.J., et al., "Etiology of Type II Diabetes Mellitus: Role of the Foregut," *World J. Surg.*, 25:527-531 (2001).
Pories, W.J., "Why Does the Gastric Bypass Control Type 2 Diabetes Mellitus?" *Obesity Surgery*, 2:303-313 (1992).
Rubino, F., et al., "Potential of Surgery for Curing Type 2 Diabetes Mellitus," *Annals of Surgery*, 236(5):554-559 (2002).
Dolan, K. et al., "Treating Diabetes in the Morbidly Obese by Laproscopic Gastric Banding," *Obesity Surgery* 13:439-443 (2003).
Song, H.Y., et al., "Covered Retrievable Expandable Nitinol Stents in Patients with Benign Esophageal Strictures: Initial Experience," *Radiology* 217:551-557 (2000).
Hwang, J.C., et al., "Covered Retrievable Tracheobronichial Hinged Stent: An Experimental Study in Dogs," *J. Vasc. Interv. Radiol.*, 12:1429-1436 (2001).
Yoon, C.J., et al., "Removal of Retrievable Esophageal and Gastrointestinal Stents: Experience in 113 Patients," *American J. of Roentgenology* 183:1437-1444 (2004).
Lee, S.H., "The Role of Oesophageal Stenting in the Non-Surgical Management of Oesophageal Strictures," *The British J. of Radiology* 74:891-900 (2001).
Irie, T., et al., "Relocatable Gianturco Expandable Metallic Stents," *Radiology* 178:575-578 (1991).
Lee, B.H., et al., "New Self-Expandable Spiral Metallic Stent: Preliminary clinical Evaluation in Malignant Biliary Obstruction," *J. Vasc Intery Radiol.*, 6(4):635-340 (1995).
Song, H.Y., et al., "Tracheobronchial Strictures: Treatment with a Polyurethane-Covered Retrievable Expandable Nitinol Stent-Initial Experience," *Radiology* 213:905-912 (1999).
Song, H.Y., et al., "Benign and Malignant Esophageal Strictures: Treatment with a Polyurethane-Covered Retrievable Expandable Metallic Stent," *Radiology* 203:747-752 (1997).
Shim, C.S., et al., "Fixation of a Modified Covered Esophageal Stent: Its Clinical Usefulness for Preventing Stent Migration," *Endoscopy* 33(10):843-848 (2001).
CHOOSTENT™, Covered Esophageal Stent, Instructions, Retrieved from the Internet (http://mitech.co.kr/uploads/images/282/use guide esophachoo_english.pdf) on Jul. 26, 2005.
International Search Report, International Application No. PCT/US2008/013540 (Mar. 26, 2009).
Written Opinion of the International Searching Authority, International Application No. PCT/US2008/013540 (Mar. 26, 2009).

* cited by examiner

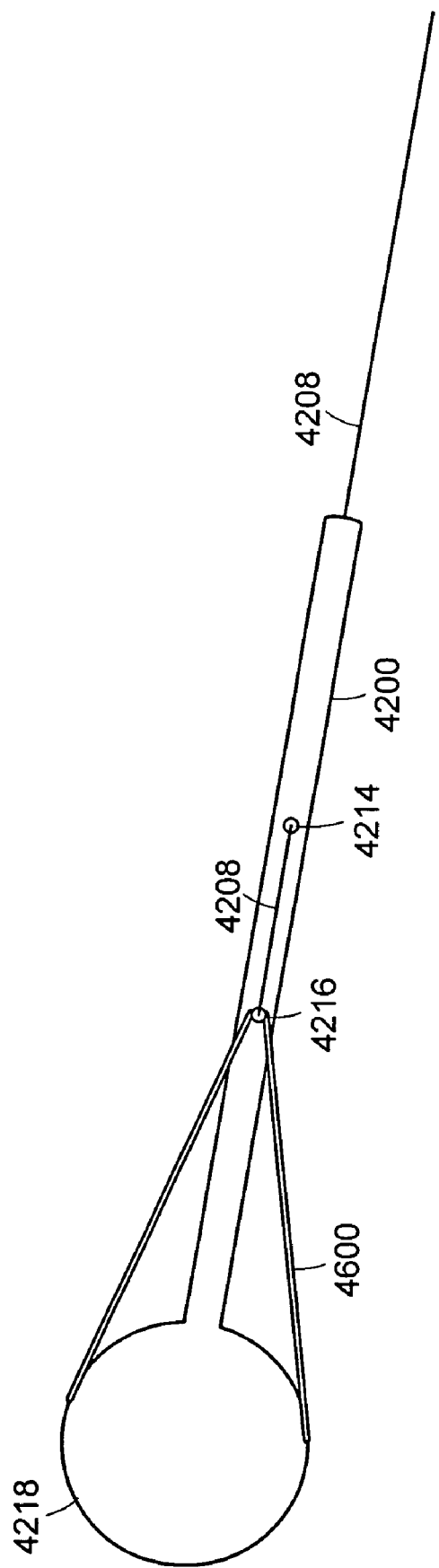

METHODS AND DEVICES FOR PLACING A GASTROINTESTINAL SLEEVE

RELATED APPLICATIONS

This application claims the benefit of U.S. Provisional Application No. 60/586,521, entitled "Methods and Articles for Placement and Removal of Gastrointestinal Sleeves" and filed on Jul. 9, 2004, and U.S. Provisional Application No. 60/610,614, entitled "Methods and Articles for Placement and Removal of Gastrointestinal Sleeves" and filed on Sep. 15, 2004. The teachings of these provisional applications are incorporated herein by reference.

BACKGROUND OF THE INVENTION

Obesity is an overwhelming health problem. According to the Center for Disease Control (CDC), over sixty percent of the United States population is overweight, and almost twenty percent are obese. This translates into about 40 million adults in the United States with a Body Mass Index (BMI) of 30 or above. The BMI is defined as a person's weight (in kilograms) divided by height (in meters), squared. To be considered clinically, morbidly obese, one must meet one of three criteria: a Body Mass Index of more than 35, one hundred pounds overweight, or 100% above ideal body weight. There is also a category for the super-obese for those weighing over 350 lbs.

Carrying this excess weight places enormous strain upon a person's body; organs are affected, as are the nervous and circulatory systems. In 2000, the National Institute of Diabetes, Digestive and Kidney Diseases (NIDDK) estimated that there were 280,000 deaths directly related to obesity. The NIDDK further estimated that the direct cost of healthcare in the US associated with obesity is $51 billion. In addition, Americans spend $33 billion per year on weight loss products. In spite of this economic cost and consumer commitment, the prevalence of obesity continues to rise at alarming rates. From 1991 to 2000, obesity rates in the US grew by 61% and worldwide obesity rates also increased dramatically.

One of the principle costs to the healthcare system stems from the co-morbidities associated with obesity. Incidence of Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple: over consumption of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon. Devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices have not been successfully implemented.

Recently, various gastrointestinal implants have been developed as potential solutions to these above problems. However, a need exists for methods and devices to place or position these implants within mammalian gastrointestinal tracts.

SUMMARY OF THE INVENTION

This invention is directed towards methods, devices, and systems for implanting or placing a gastrointestinal implant device (e.g., a gastrointestinal sleeve) into the gastrointestinal tract of a mammal (e.g., a human). The methods utilize, and the devices include, a container assembly and a gastrointestinal implant device having a proximal end that includes an anchor and a distal end that includes a sleeve.

This invention includes methods of placing a gastrointestinal implant device in a mammal. The gastrointestinal implant device includes an anchor and a flexible, floppy, thin, conformable, and/or collapsible sleeve sleeve. In some embodiments, the method comprises the steps of placing a gastrointestinal implant device in a container assembly, directing the container assembly into a mammalian gastrointestinal tract, removing the device from the container assembly, and securing the anchor to a location in the gastrointestinal tract. In some embodiments of the invention, the step of removing the device from the container assembly includes directing a portion of the sleeve to a location in the gastrointestinal tract that is distal relative to the assembly while the anchor is releasably secured in the container assembly.

In some embodiments, at least a portion of the sleeve is removed from the container assembly before the anchor is removed from the container. Optionally, the anchor is releasably secured in the container assembly while at least a portion of the sleeve is directed to a location in the gastrointestinal tract that is distal from the container assembly. The sleeve can be directed into the location by, for example, advancing a catheter having an atraumatic tip. In further embodiments, a distal portion of the catheter is less rigid than a proximal portion of the catheter.

In some embodiments of the invention, the container is directed to the duodenum of the gastrointestinal tract. In further embodiments, at least a portion of the sleeve is directed into the jejunum of the gastrointestinal tract. Optionally, the anchor is self-expanding and/or is secured in the duodenum of the gastrointestinal tract.

In some embodiments of the invention, the method further includes a step of directing a fluid (e.g., a gas and/or liquid) into the gastrointestinal tract. The fluid can be directed into the tract before and/or after the container assembly is directed into the duodenum. The fluid can be used, for example, to expand at least a portion of the gastrointestinal tract and/or to deploy or expand portions of the gastrointestinal implant device. Examples of suitable fluids include gasses (e.g., air, carbon dioxide, and/or nitrogen) and liquids (e.g., saline and mixtures of liquid saline and a contrast medium). In some embodiments, at least 60 milliliters of fluid are directed into the gastrointestinal tract.

In some embodiments of the invention, the container assembly includes a first chamber and the step of placing the device in the assembly includes storing the anchor in the first chamber. Optionally, the step of removing the device from the assembly includes directing at least a portion of the sleeve to a location in the gastrointestinal tract that is distal relative to the first chamber while the anchor is releasably secured in the first chamber. In further embodiments of the invention, the container assembly further includes a second chamber and the step of placing the device in the assembly includes storing at least a portion of the sleeve in the second chamber. Optionally, the step of removing the device from the assembly includes directing the second chamber to a location in the gastrointestinal tract that is distal relative to the first chamber while the anchor is releasably secured in the first chamber and the sleeve is releasably secured in the second chamber.

This invention also includes delivery systems for placing a gastrointestinal implant device in a mammalian gastrointestinal tract. In some embodiments of the invention, the delivery systems comprise a container assembly and a gastrointestinal implant device. The implant device includes a proximal end and a distal end, and the proximal end includes an anchor and the distal end includes a sleeve. The proximal end and the distal end are stored within the container assembly.

In further embodiments, the systems include an anchor locking mechanism located within the assembly. The anchor locking mechanism can include an anchor locking wire that extends through a portion of the device. The system can further include a means for displacing an anchor from the container assembly (e.g., an anchor plunger). Optionally, the anchor is self-expanding. The exterior portion of the container assembly can include a visible marker for positioning the assembly within the gastrointestinal tract of a mammal.

In additional embodiments, the systems further include a catheter releasably secured to the distal end of the device. For example, the catheter can be releasably secured to the distal end of the sleeve. The catheter can include an atraumatic tip (e.g., a releasable ball) and/or a distal portion of the catheter can be less rigid than a proximal portion of the catheter.

In some embodiments, wherein the assembly includes a first chamber and a second chamber, the first chamber storing at least a portion of the proximal end and the second chamber storing at least a portion of the distal end. In further embodiments, at least a portion of the second chamber is stored in the first chamber.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 4A-4L illustrate additional embodiments of the invention that include a gastrointestinal implant delivery catheter system and a method of use.

FIGS. 7A-7C illustrate embodiments for attaching a releasable atraumatic element to the distal end of a delivery catheter.

DETAILED DESCRIPTION OF THE INVENTION

A description of preferred embodiments of the invention follows. While this invention has been particularly shown and described with references to preferred embodiments thereof, it will be understood by those skilled in the art that various changes in form and details may be made therein without departing from the scope of the invention encompassed by the appended claims.

This invention features devices and methods for implanting or placing gastrointestinal implant devices (e.g., intestinal sleeves) into mammals (e.g., a human). Several gastrointestinal implant devices (e.g., intestinal sleeves) have been developed and are suitable for implementation or placement within a gastrointestinal tract using the methods and devices of this invention. Some examples of such devices are described in U.S. patent application Ser. No. 10/339,786, filed Jan. 9, 2003, and entitled "Bariatric Sleeve;" U.S. patent application Ser. No. 10/726,011, filed Dec. 2, 2003, and entitled "Anti-Obesity Devices;" U.S. patent application Ser. No. 10/810,317, filed Mar. 26, 2004, and entitled "Enzyme Sleeve;" U.S. patent application Ser. No. 10/811,293, filed Mar. 26, 2004, and entitled "Anti-Obesity Devices;" U.S. patent application Ser. No. 10/858,852, filed Jun. 1, 2004, and entitled "Methods and Apparatus for Anchoring Within the Gastrointestinal Tract;" U.S. Provisional Application No. 60/544,527, filed Feb. 13, 2004, and entitled "Methods and Apparatus for Using a Sleeve Within the Gastrointestinal Tract;" U.S. patent application Ser. No. 10/858,851, filed Jun. 1, 2004, and entitled "Intestinal Sleeve;" U.S. Patent Application No. 60/611,038, filed Sep. 17, 2004, and entitled "Multi-Wave Anchor;" U.S. Provisional Application No. 60/645,296, filed on Jan. 19, 2005, and entitled "Gastrointestinal Sleeve;" and U.S. Provisional Application No. 60/645,287, filed Jan. 19, 2005, entitled "Anchoring Devices." The teachings of each of these applications are incorporated herein by reference.

Figure 1A:
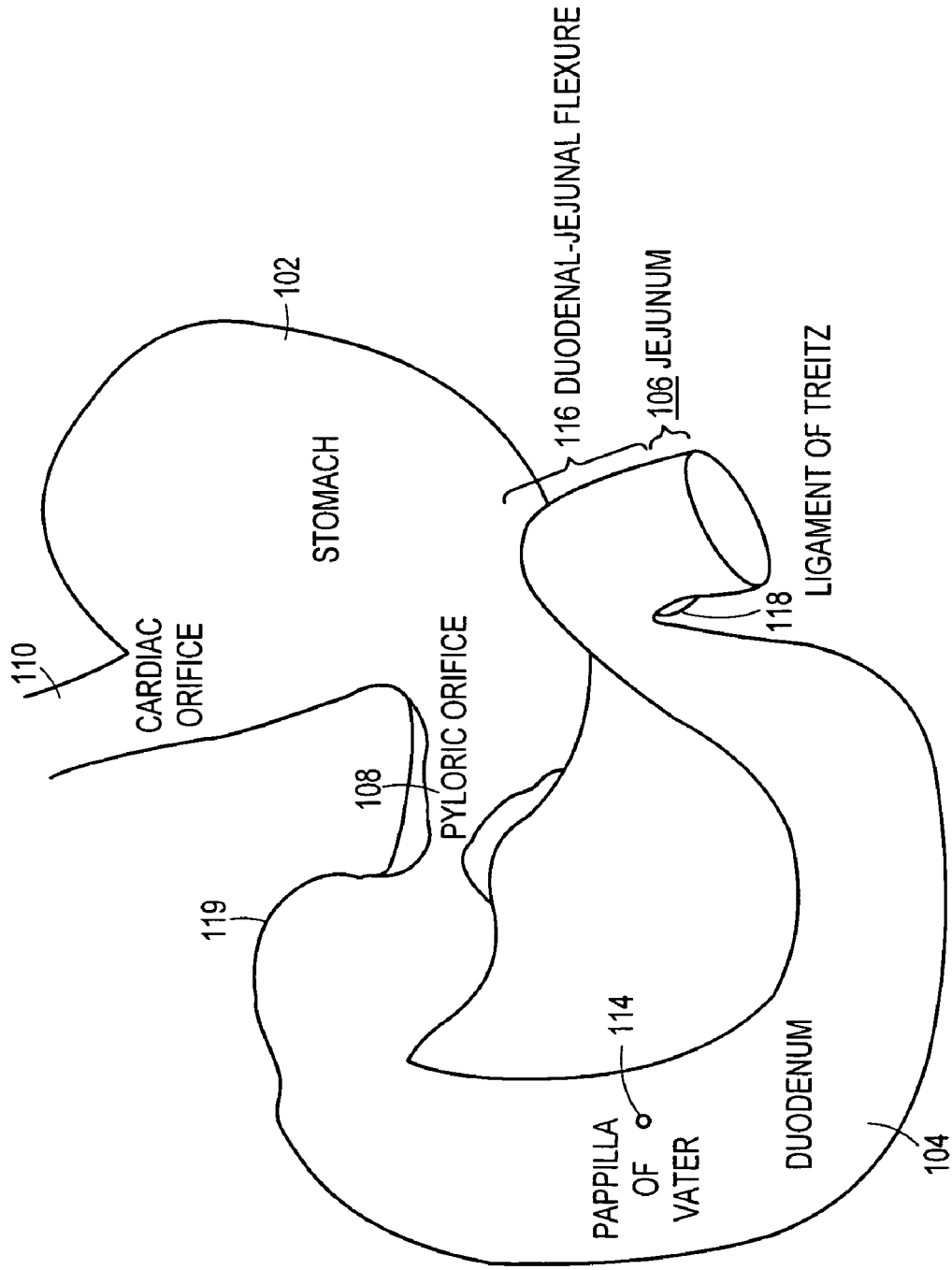
FIG. 1A is a sectional view of a portion of the digestive tract in a mammalian body.

FIG. 1A is a sectional view of a portion of the digestive tract in a mammalian body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice or pylorus 108 and enters the small intestine.

The pylorus 108 is a distal aperture of the stomach 102 surrounded by a strong band of circular muscle. The small intestine, about 15-20 feet in length, is a convoluted tube, extending from the pylorus 108 to the ileo-caecal valve where it terminates in the large intestine. The small intestine has three sections, the duodenum 104, jejunum 106 and the ileum (not shown in FIG. 1). The duodenum 104 makes up the first 10-12 inch section of the small intestine and tends to be the shortest, widest, and most fixed part of the small intestine.

The duodenum 104 has four sections which typically form a U shape: superior, descending, transverse, and ascending. The superior section is about two inches long and ends at the neck of the gall bladder. The superior section also defines a feature referred to as the duodenal bulb 119 that begins just distal to the pylorus 108 and extends for about 1 to 1.5 inches in an adult human. The duodenal bulb 119 defines a lumen therein that is slightly larger than the distal duodenum 104. Advantageously, the duodenal bulb 119 exhibits less motion than the pylorus 108 and even distal portions of the duodenum 104. Notably, the motion is substantially limited to contractions without having a significant linear component (i.e., no movement along the central axis of the intestine). The tissue of the intestinal wall of the pylorus 108, and to some extent that of the duodenal bulb 119, tends to be thicker than that of other portions of the small intestine, but the tissue thins as one moves away from the pylorus 108.

The descending section of the duodenum 104 is about three to four inches long and includes a nipple shaped structure, the papilla of Vater 114, through which pancreatic juice from the pancreas and bile produced by the liver and stored by the gall bladder enter the duodenum from the pancreatic and bile ducts. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body," by Henry Gray) and "Human Physiology," Vander, $3^{rd}$ ed, McGraw Hill, 1980, the contents of which are incorporated herein by reference in their entirety.

This invention includes methods and devices for placing or implanting a gastrointestinal implant device in a mammal. For example, this invention includes methods and devices for implanting a gastrointestinal sleeve. In some embodiments, the gastrointestinal sleeve includes an anchor portion and a floppy, flexible, thin, conformable, and/or collapsible sleeve portion.

Figure 1B:
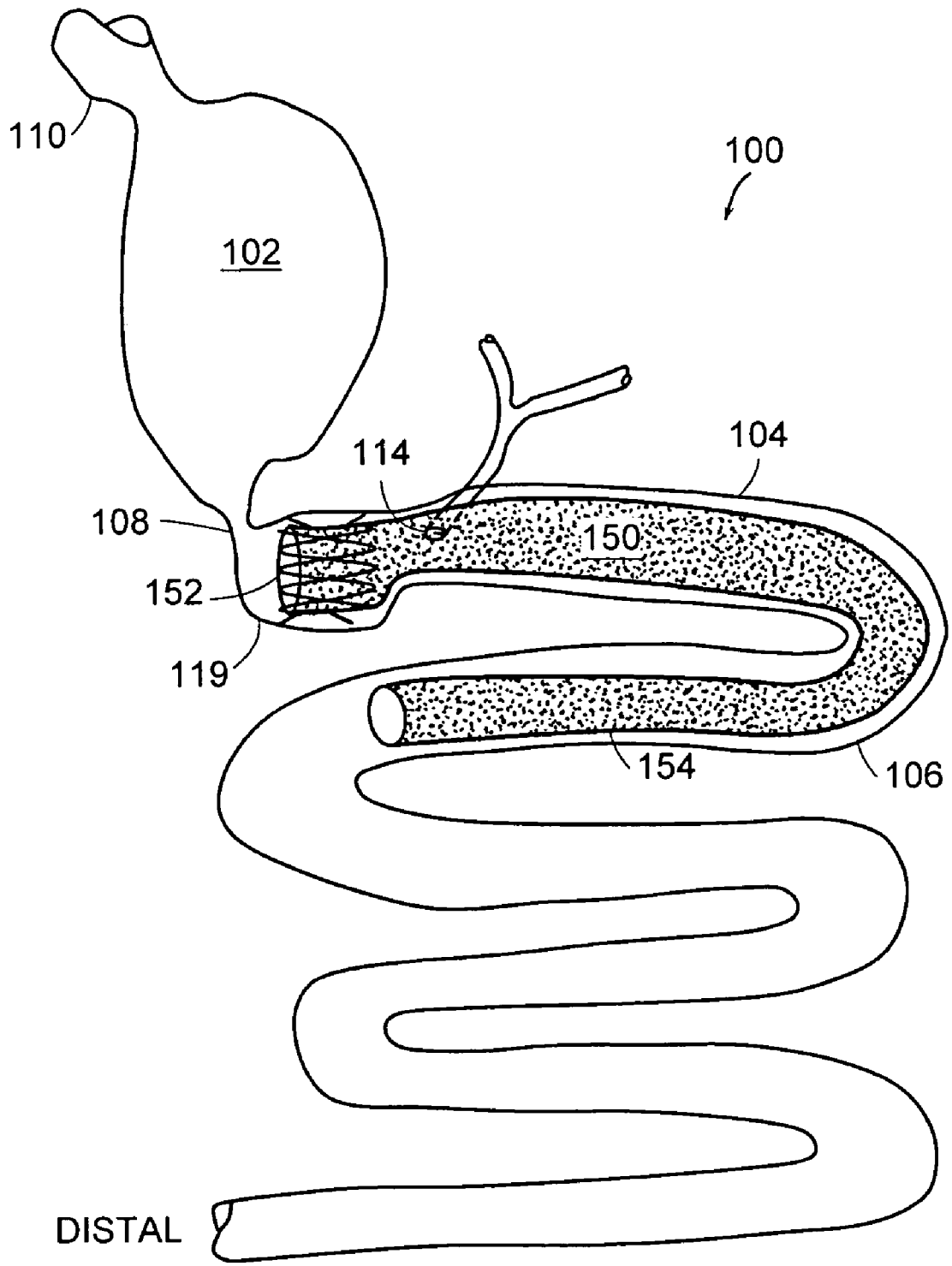
FIG. 1B illustrates a gastrointestinal implant device after it has been implanted into the gastrointestinal tract of a mammal.

FIG. 1B illustrates gastrointestinal implant device 150 after it has been implanted into the gastrointestinal tract of a mammal using embodiments of the methods and devices of this invention. Gastrointestinal implant device comprises a proximal portion or end that includes anchor 152 and a distal portion or end that includes a barrier or sleeve 154. When implanted, as shown in FIG. 1B, the central axis of anchor 152 is substantially aligned with the central axis of the duodenum, allowing chyme to pass through device 150. Additionally, anchor 152 minimizes trauma to the tissue by providing sufficient flexibility and compliance, minimizes the likelihood of tissue erosion, and provides a solid anchoring point to the tissue.

Anchor 152 can be removably attached within the body using the methods described herein, including the use of barbs attached to, and/or formed on, the anchor itself. In some embodiments, the anchor is attached or secured within the gastrointestinal tract without the use of barbs. When implanted, anchor 152 allows sleeve 154 to be securely implanted within the duodenum, preferably providing a fluid seal at the proximal end.

In some embodiments, the device is anchored in the bulbous duodenum. For purposes of anchoring a gastrointestinal device, the bulbous duodenum offers several advantages over other areas in of gastrointestinal tract. First, the duodenal bulb is proportionally sized to capture an anchor. That is, it provides a cavity having a relatively large diameter bounded by anatomies having smaller diameters in both the proximal and distal directions. Thus, the duodenal bulb is naturally configured to retain a suitably shaped anchor. Additionally, the duodenal bulb is relatively less active than either the pylorus or the distal portions of the duodenum. Movement of the surrounding tissue can act to dislodge an anchor over time. The duodenal bulb, at least in part, acts as a holding area for chyme received from the stomach. Thus, the duodenal bulb provides a more stable anchoring platform as there is relatively less movement than at other portions of the gastrointestinal tract. Still further, the tissue of at least the proximal portion of the duodenal bulb is thicker than the tissue of the distal duodenum, thus, the duodenal bulb provides a better anchoring platform as it is adapted to retain fasteners (e.g., barbs).

Figure 2A:
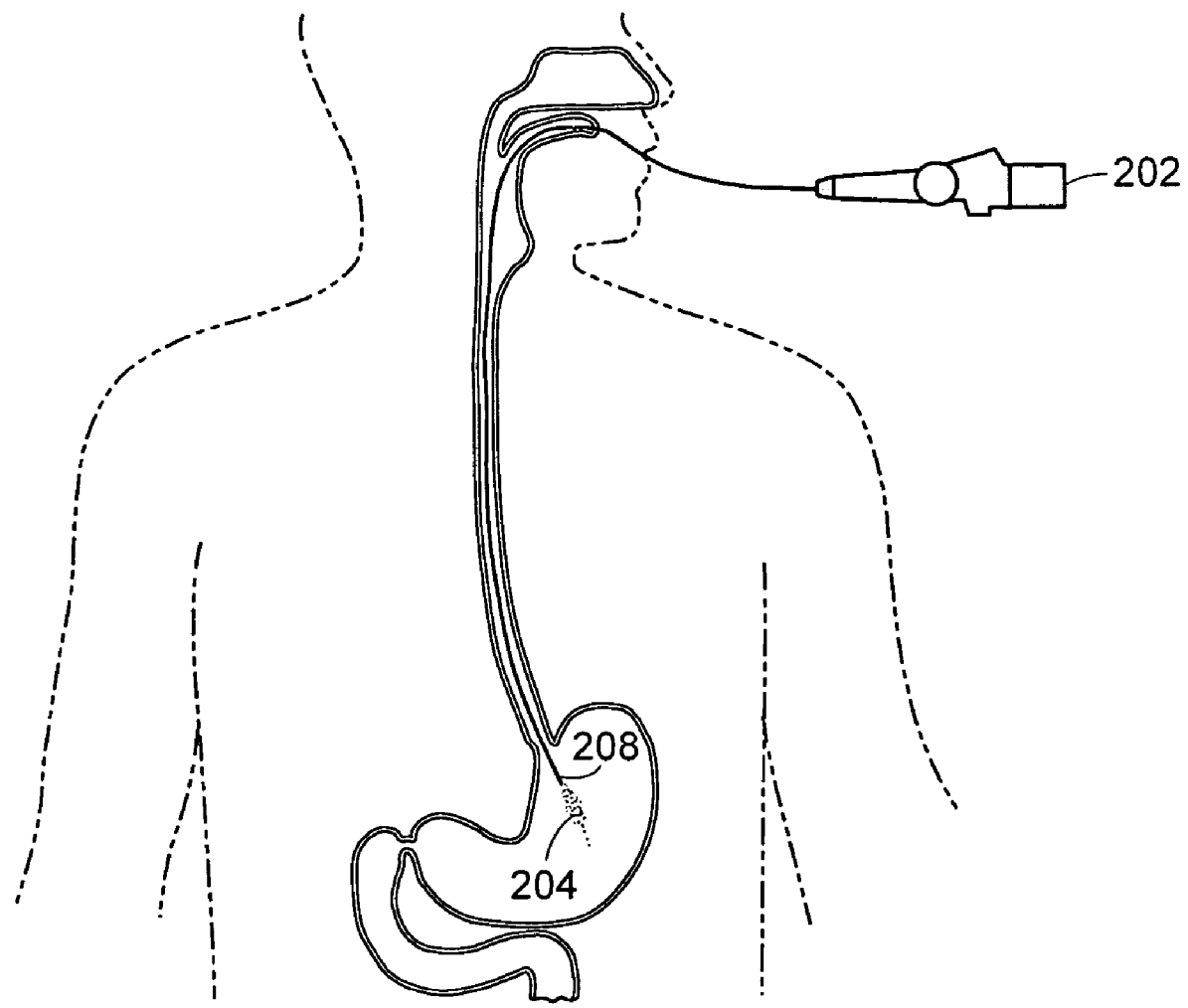
FIGS. 2A-2Y are a series of sequential diagrams illustrating multiple embodiments of methods of the invention.
Figure 2B:
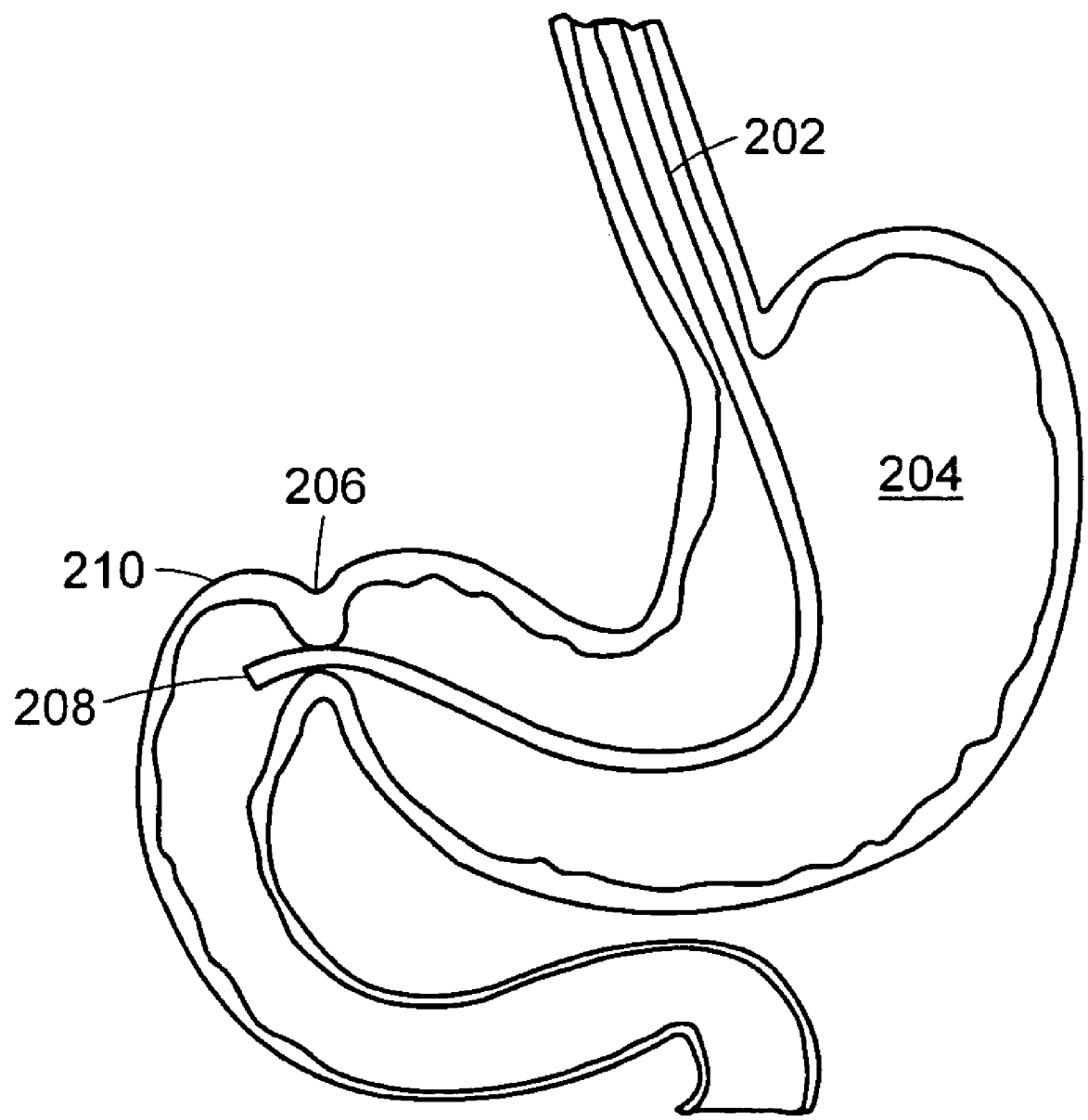
Figure 2C:
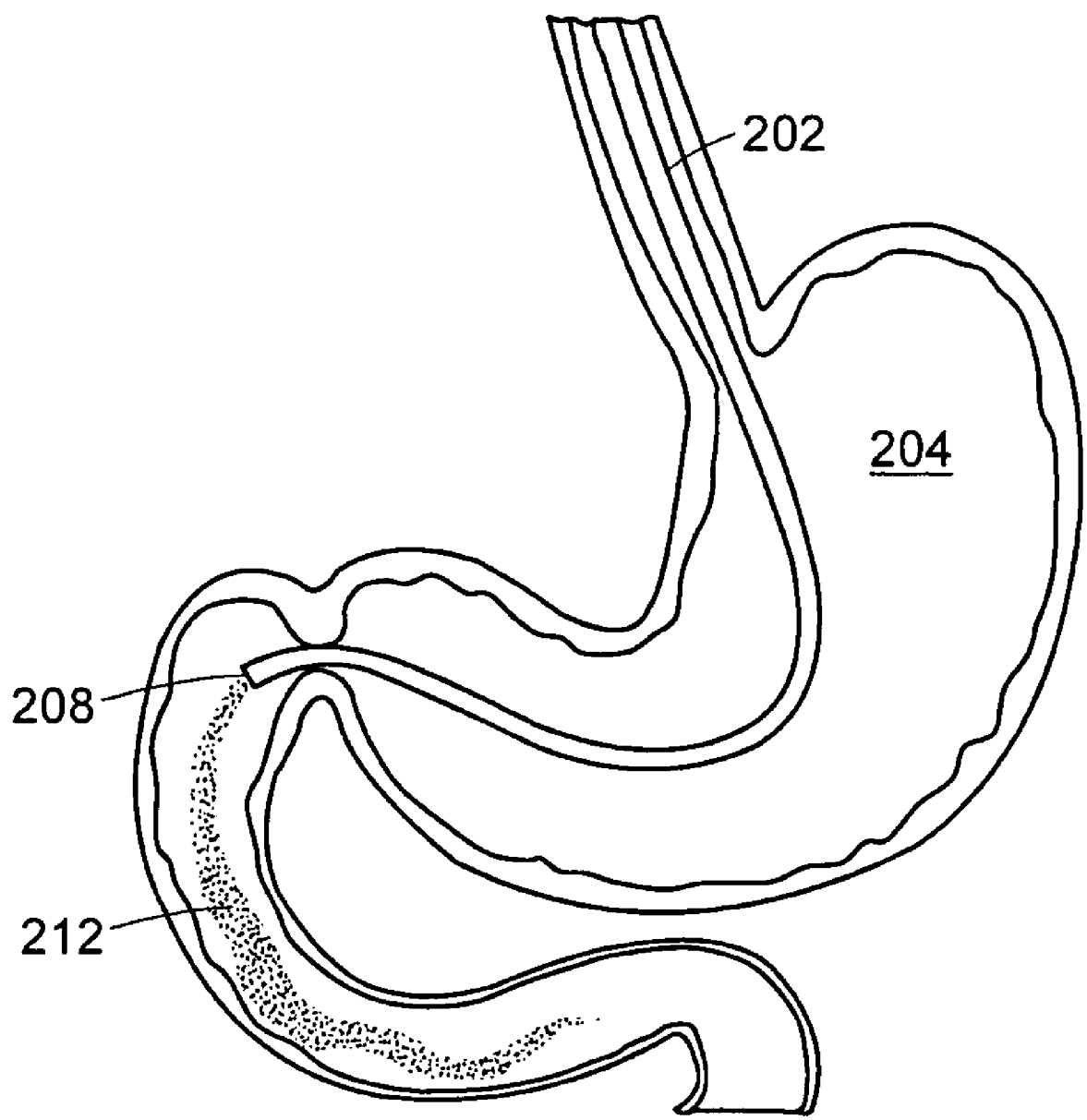
Figure 2D:
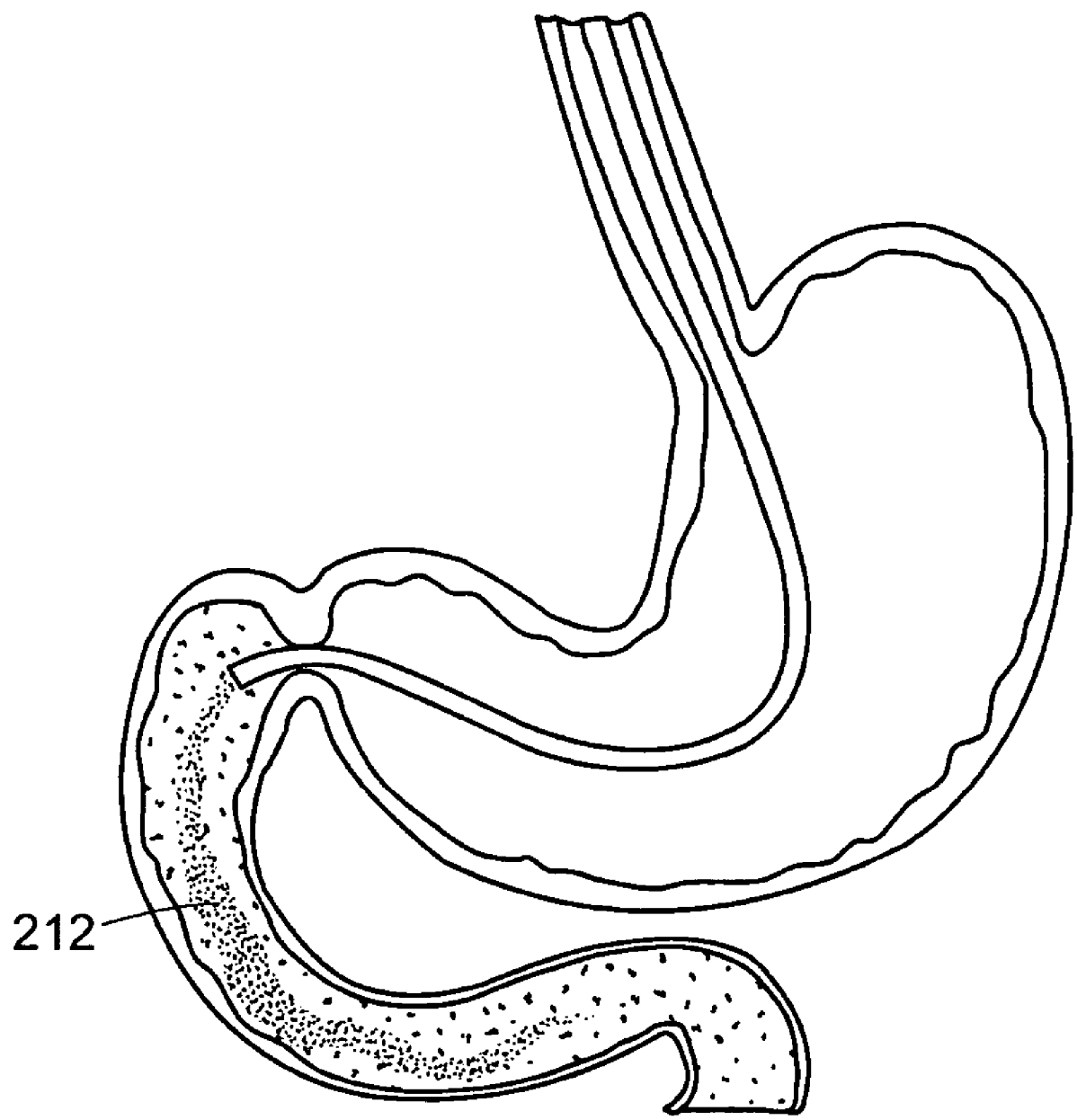
Figure 2E:
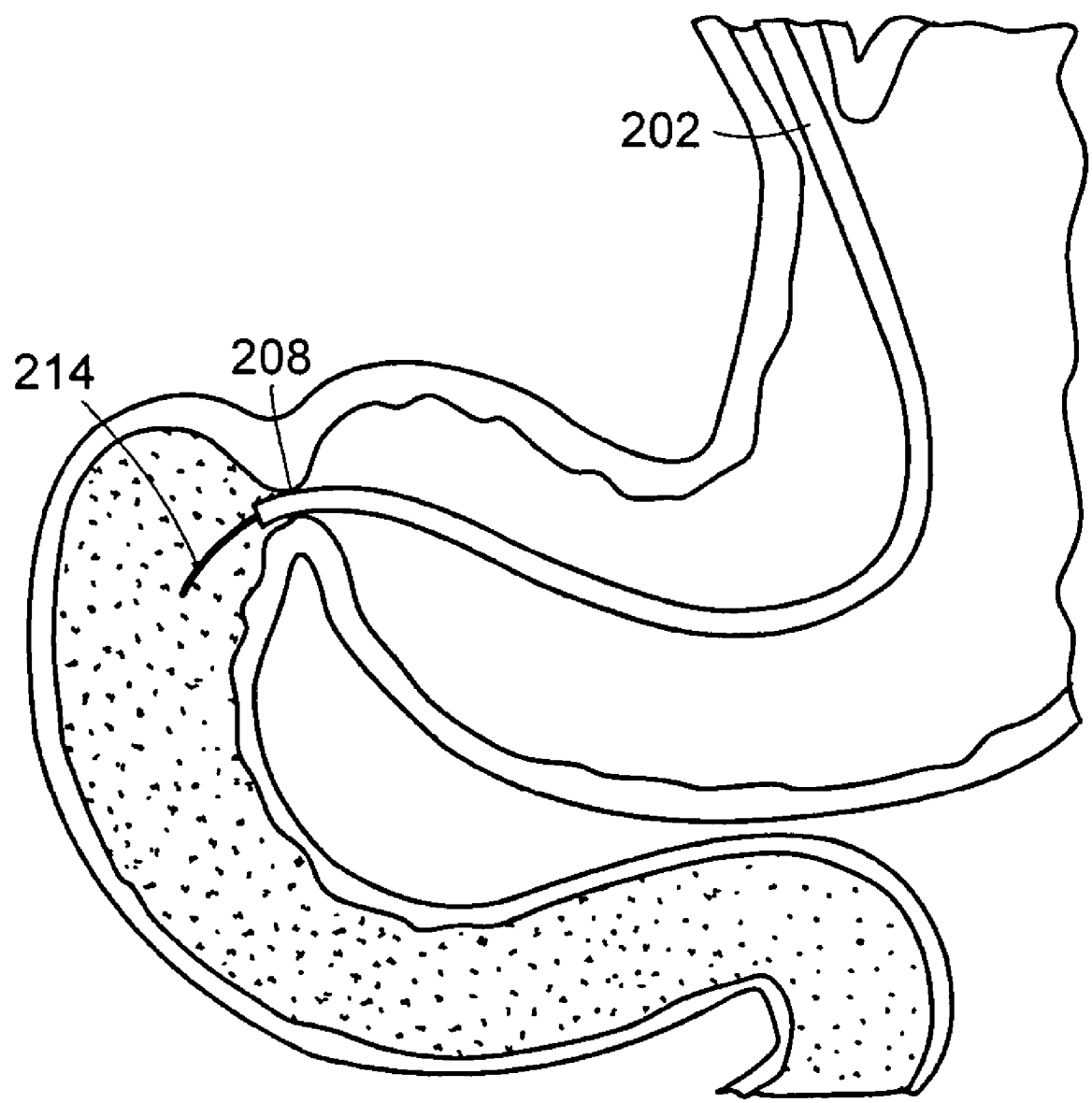
Figure 2F:
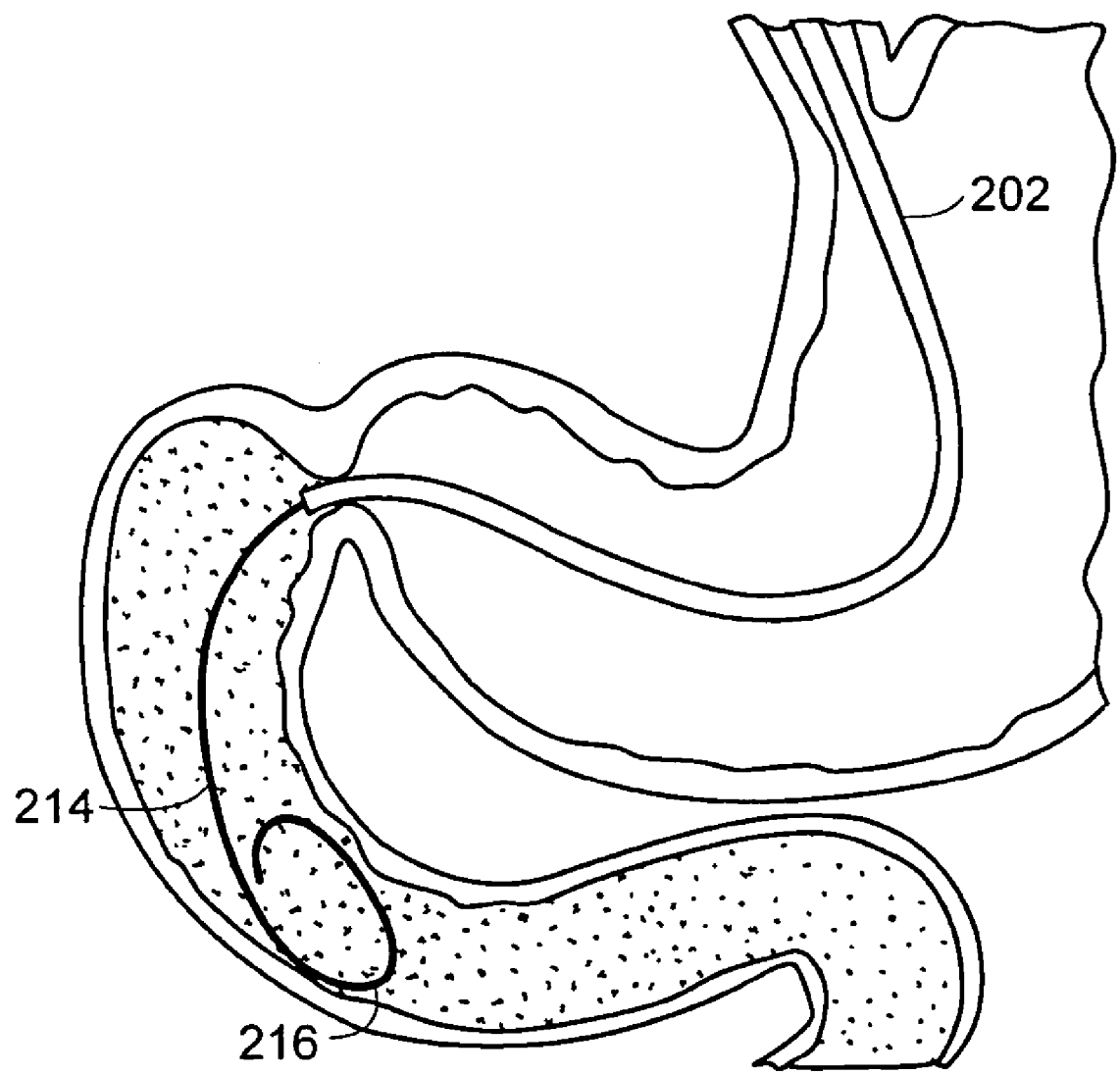
Figure 2G:
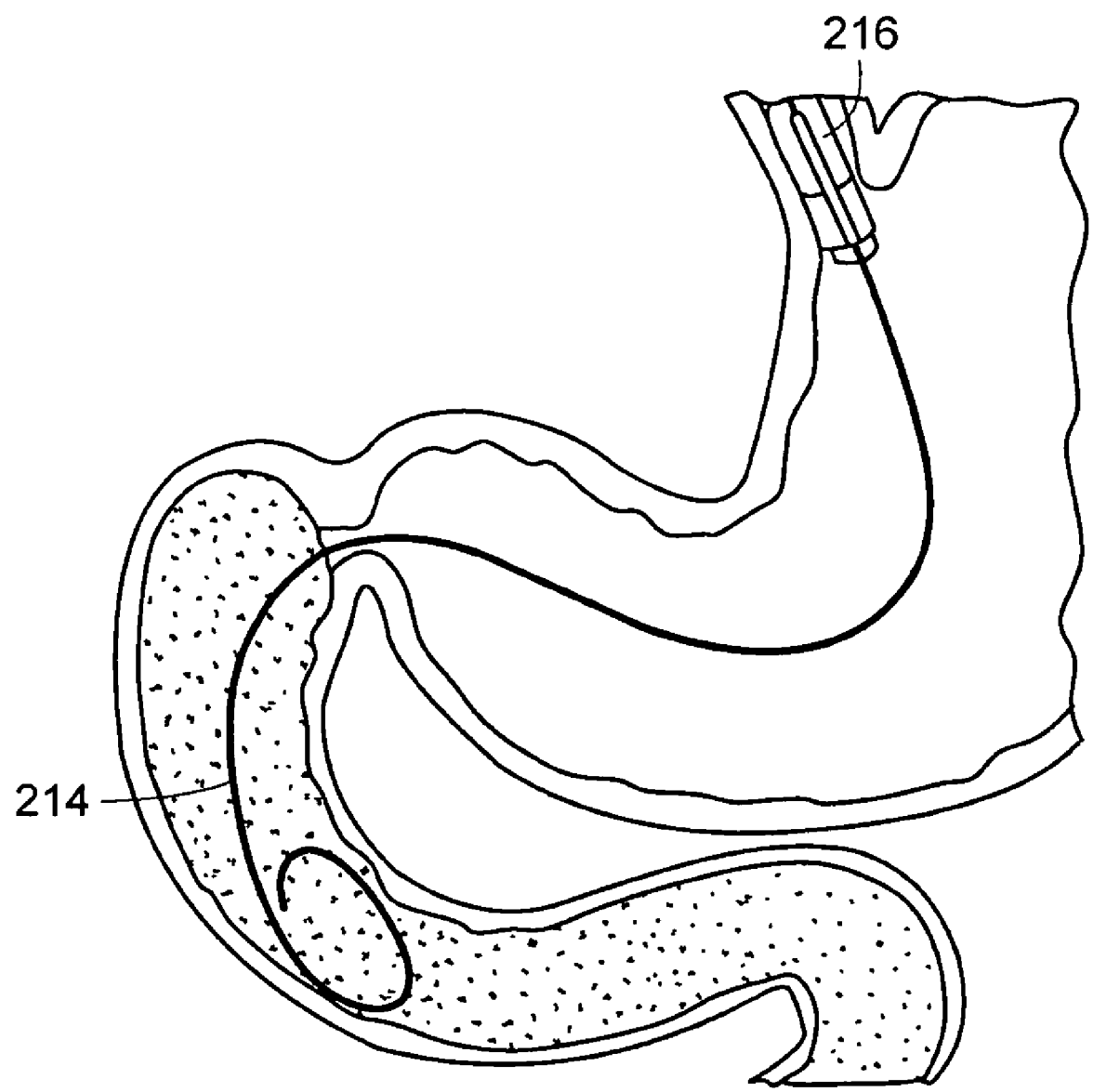
Figure 2H:
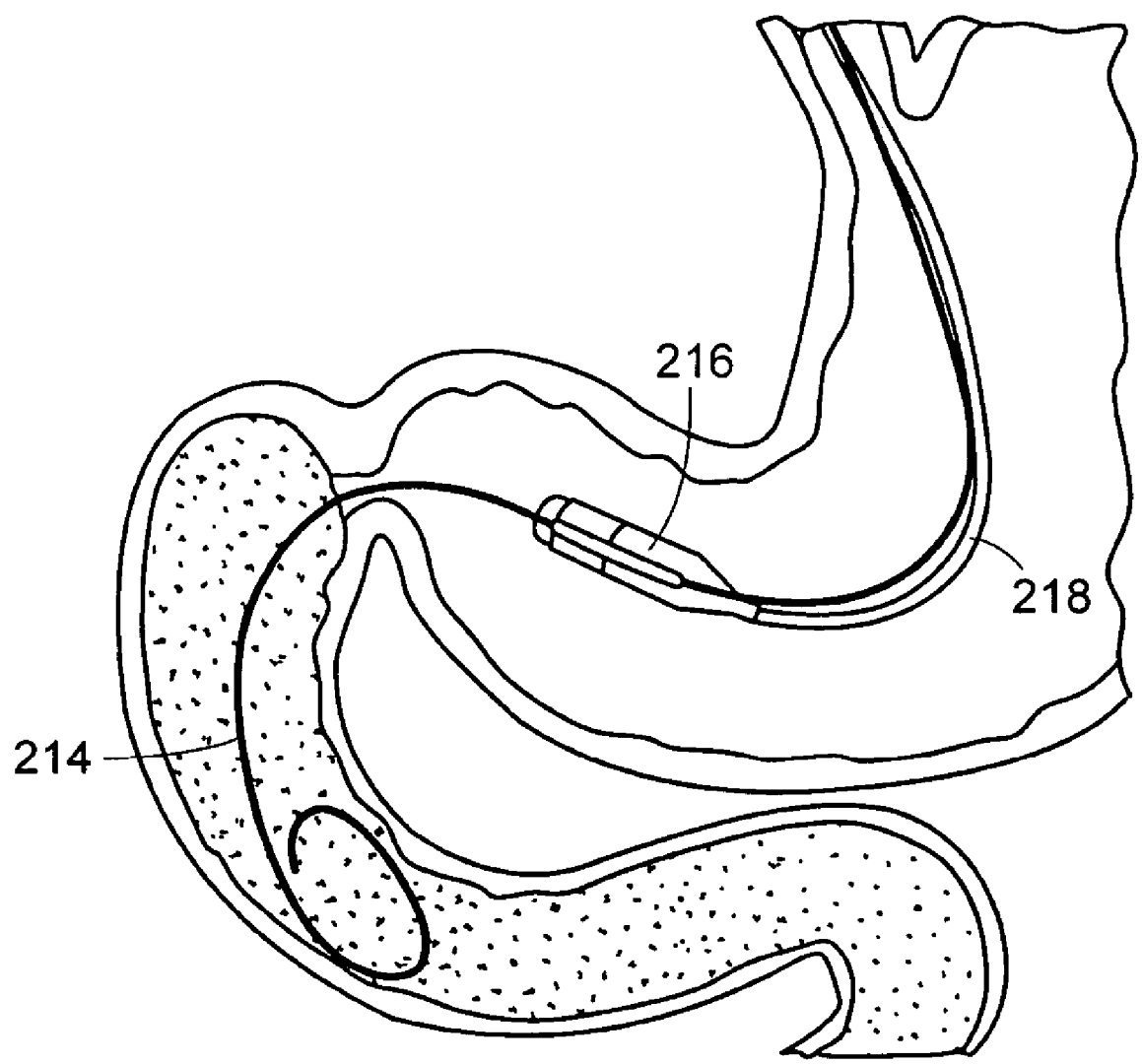
Figure 2I:
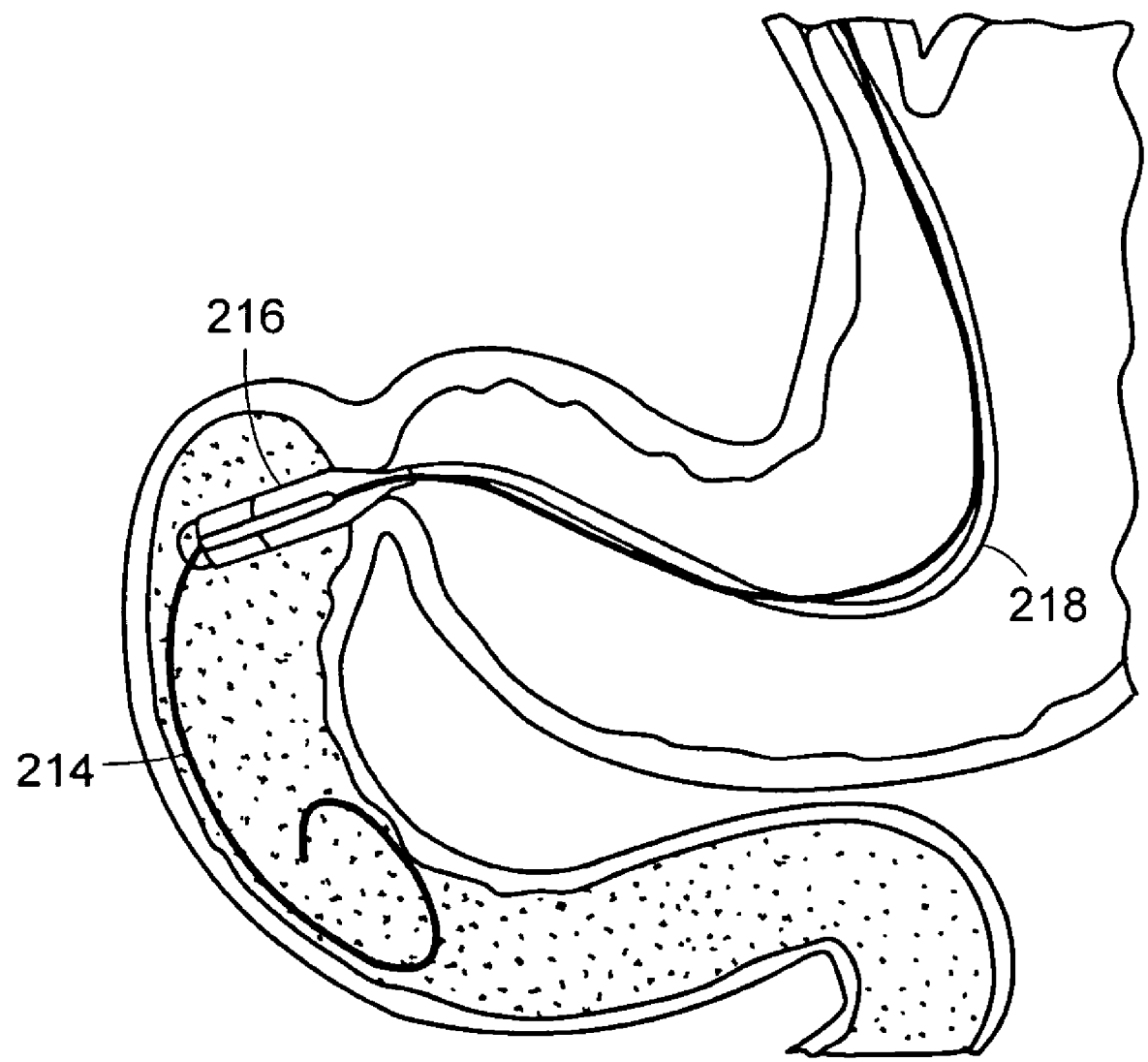
Figure 2J:
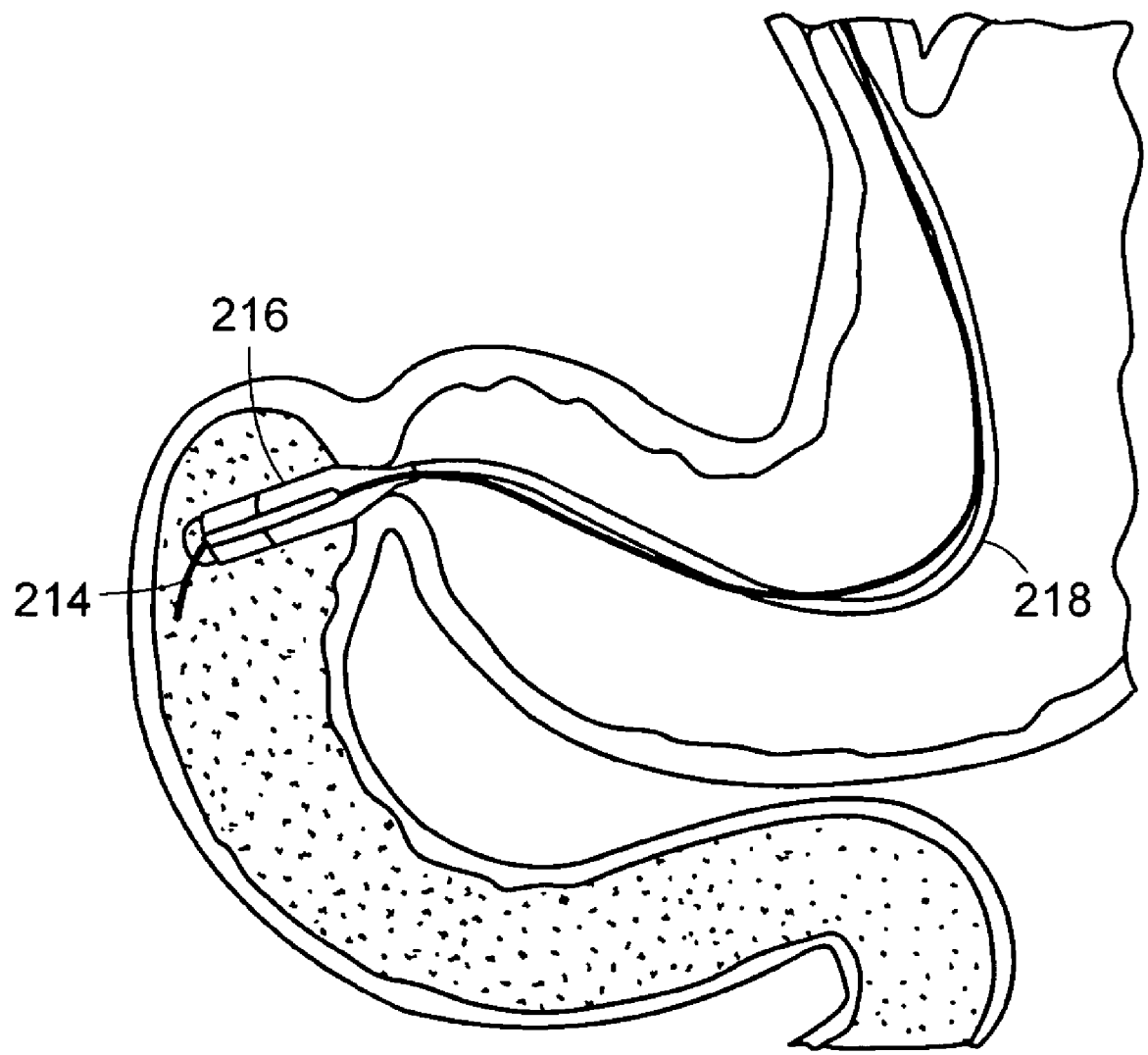
Figure 2K:
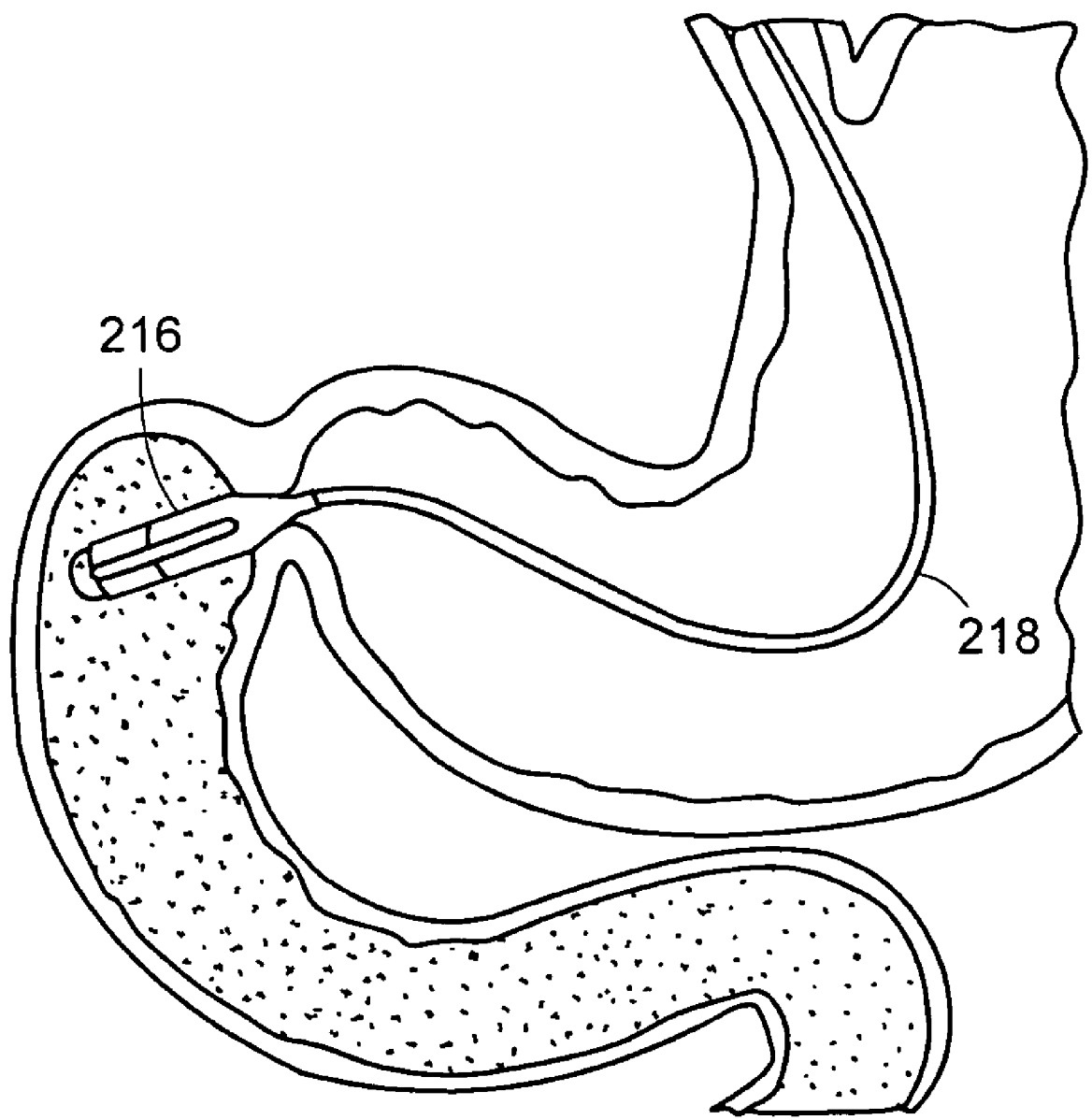
Figure 2L:
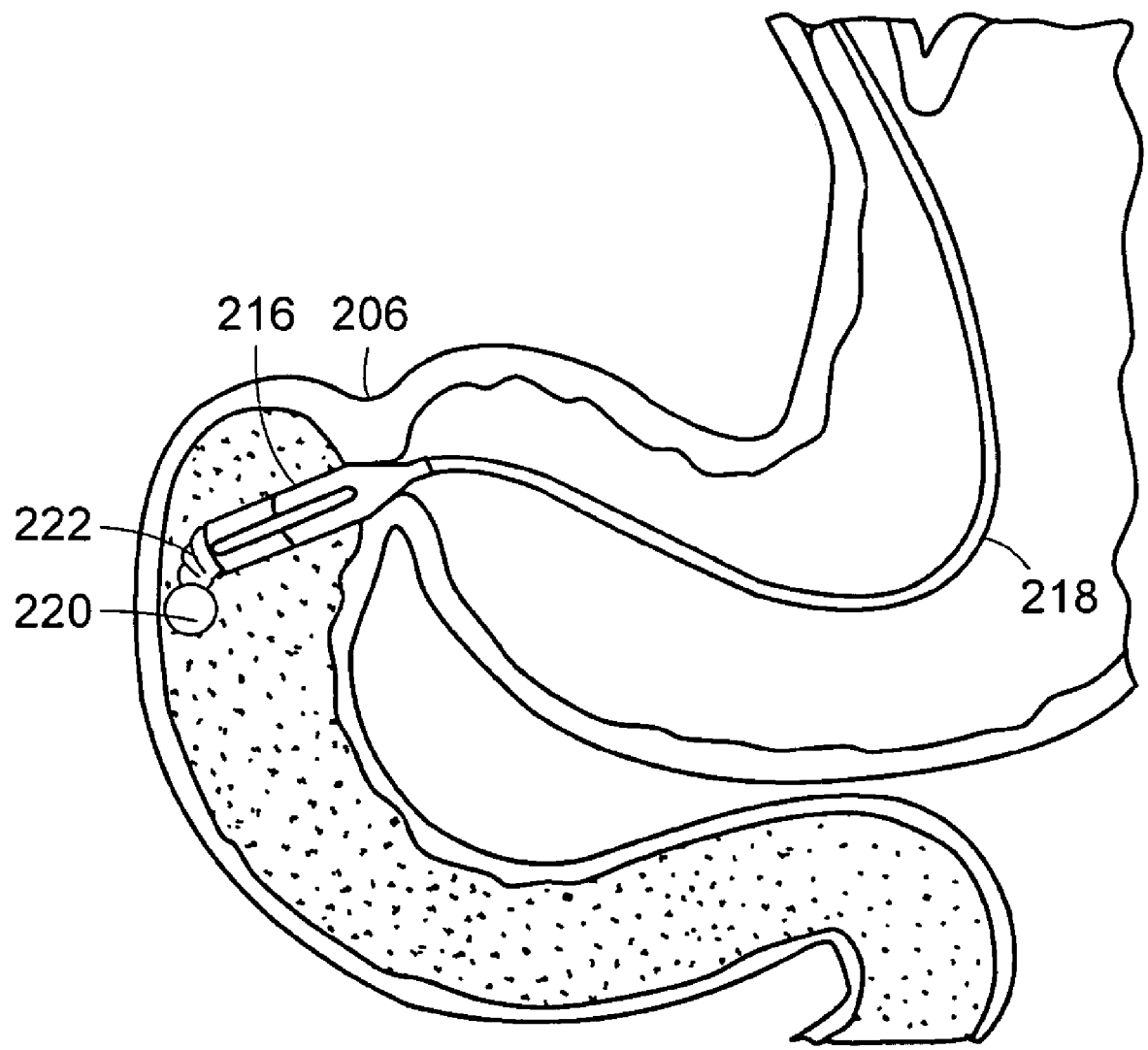
Figure 2M:
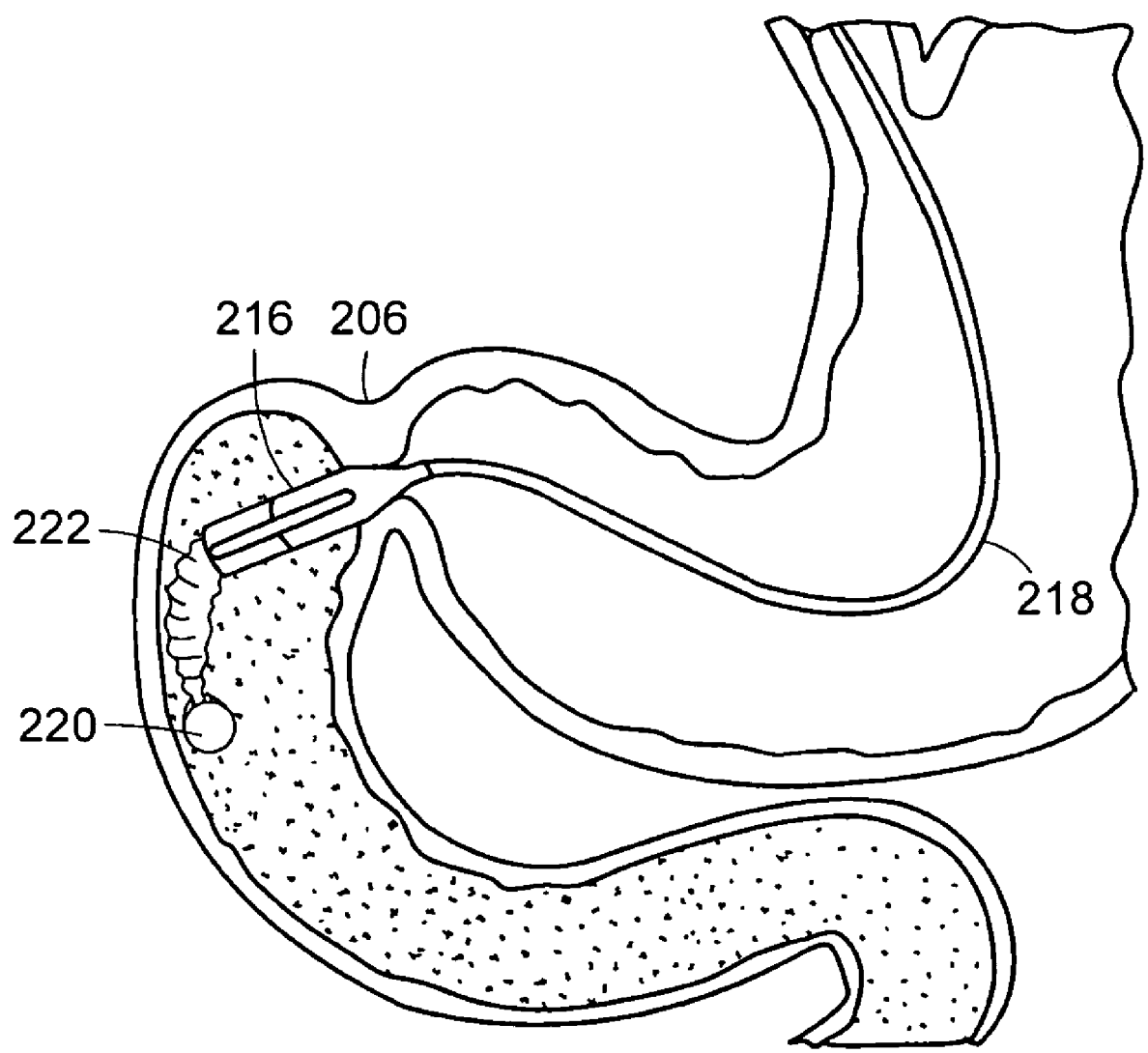
Figure 2N:
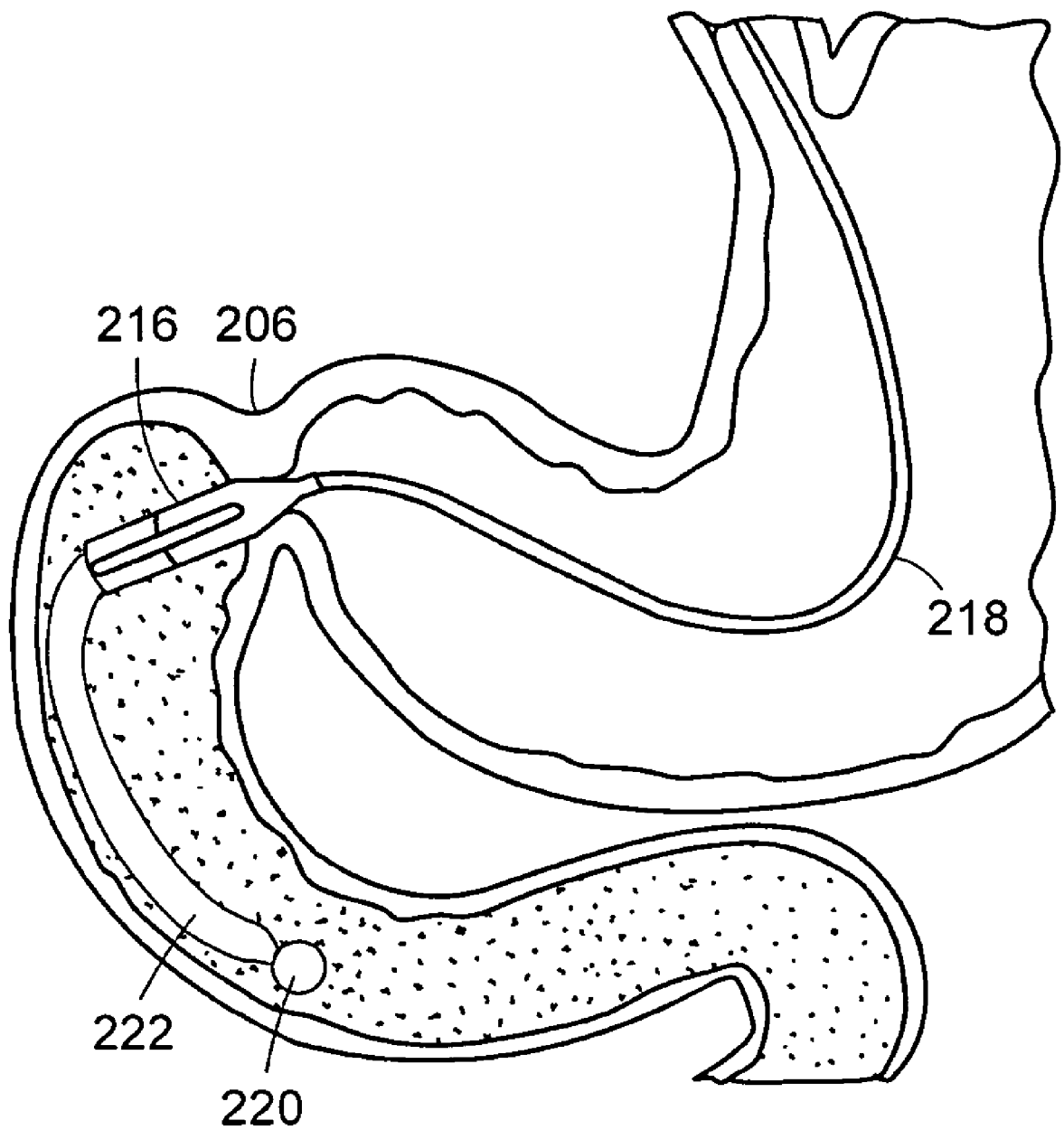
Figure 2O:
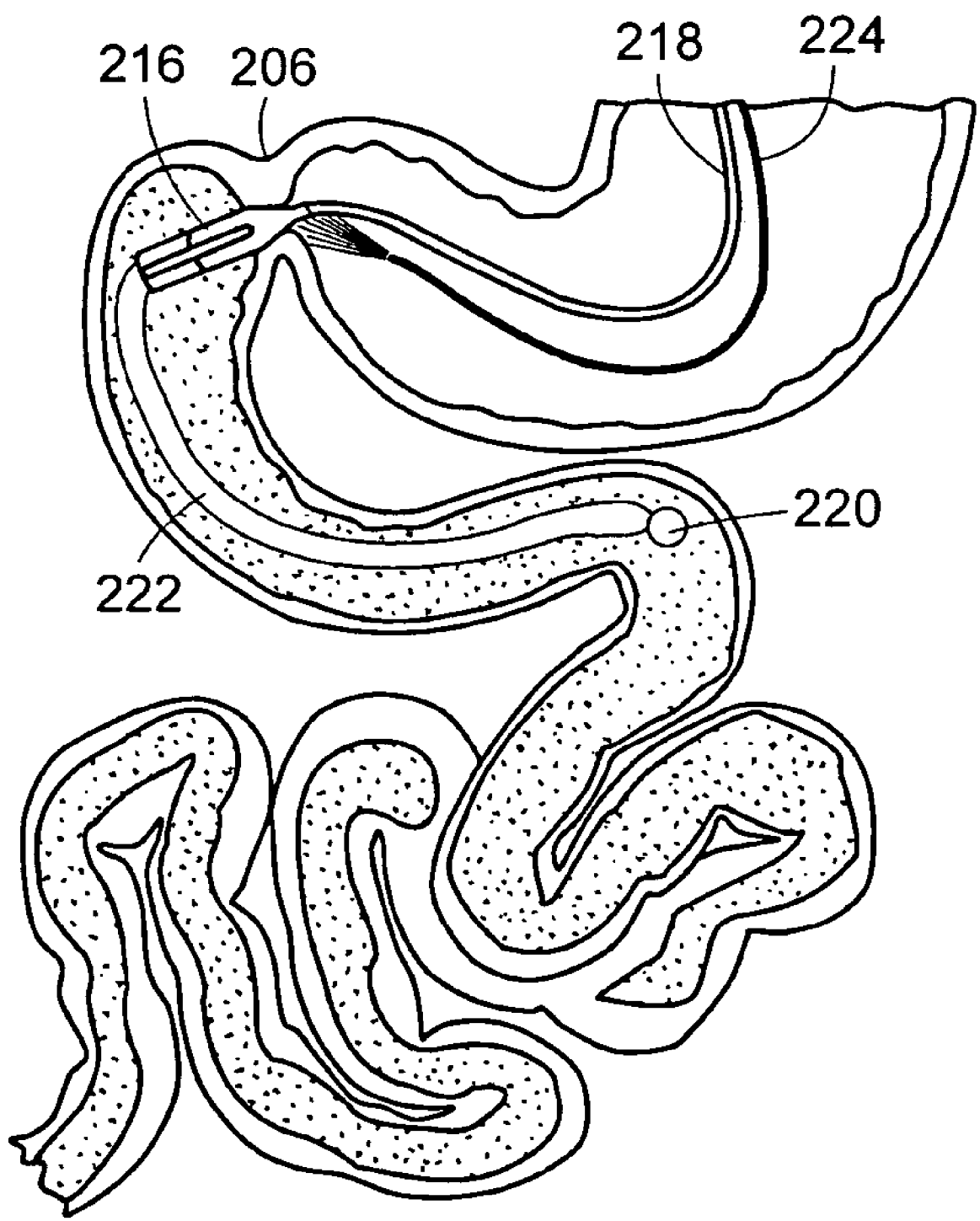
Figure 2P:
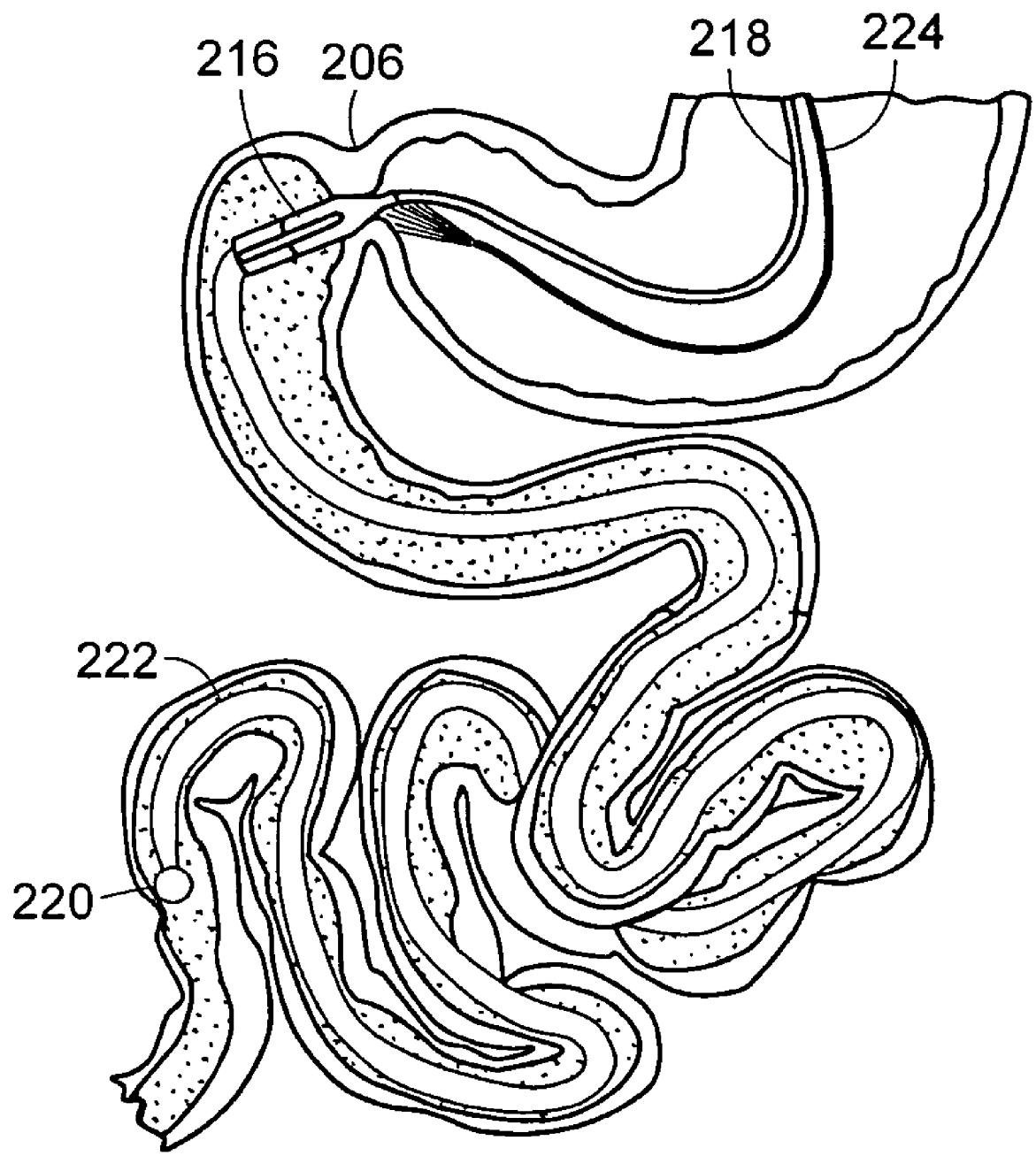
Figure 2Q:
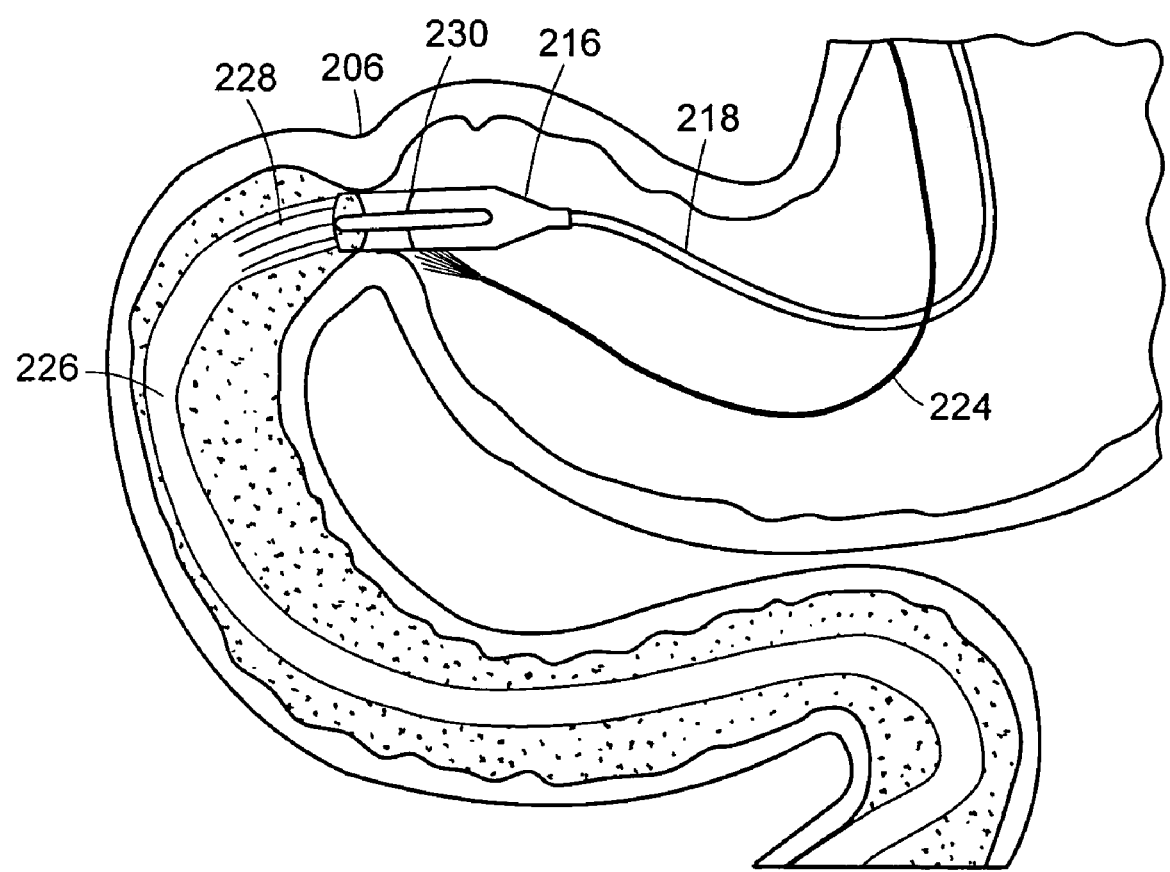
Figure 2R:
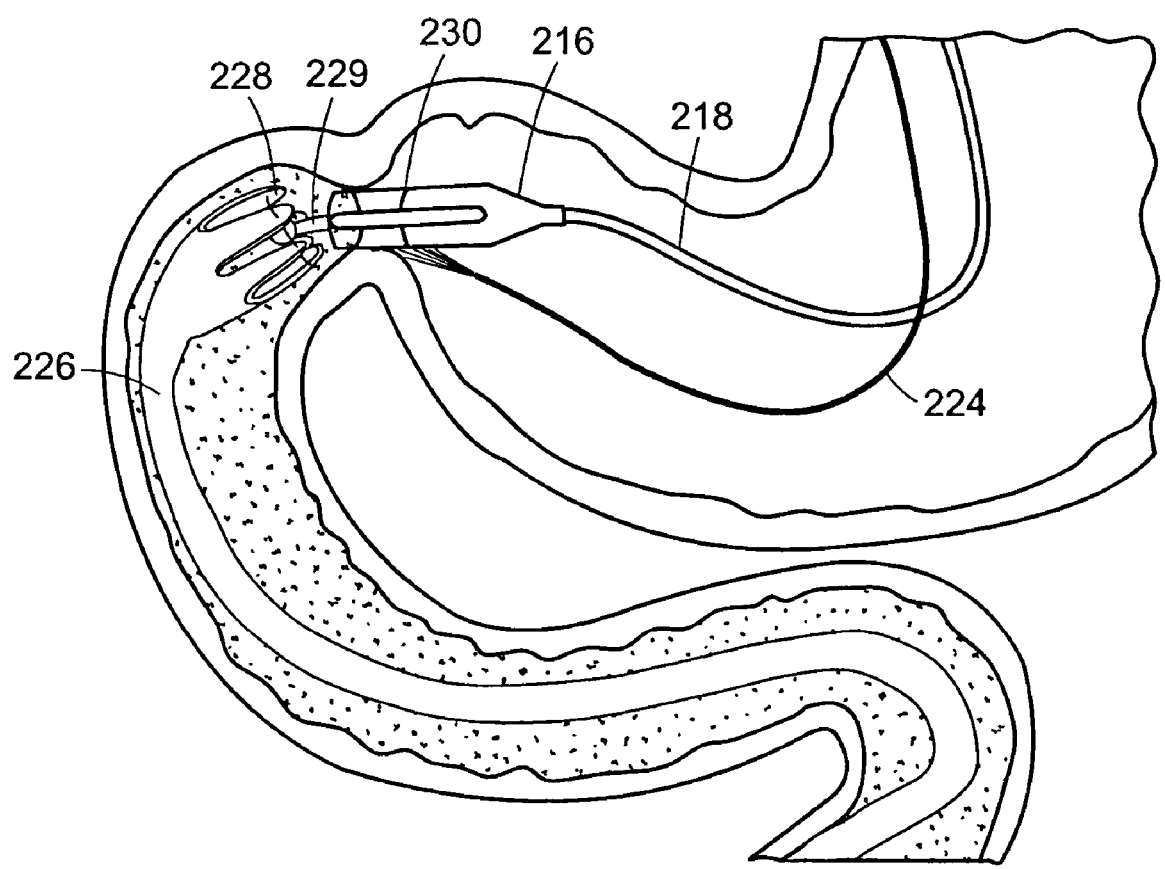
Figure 2S:
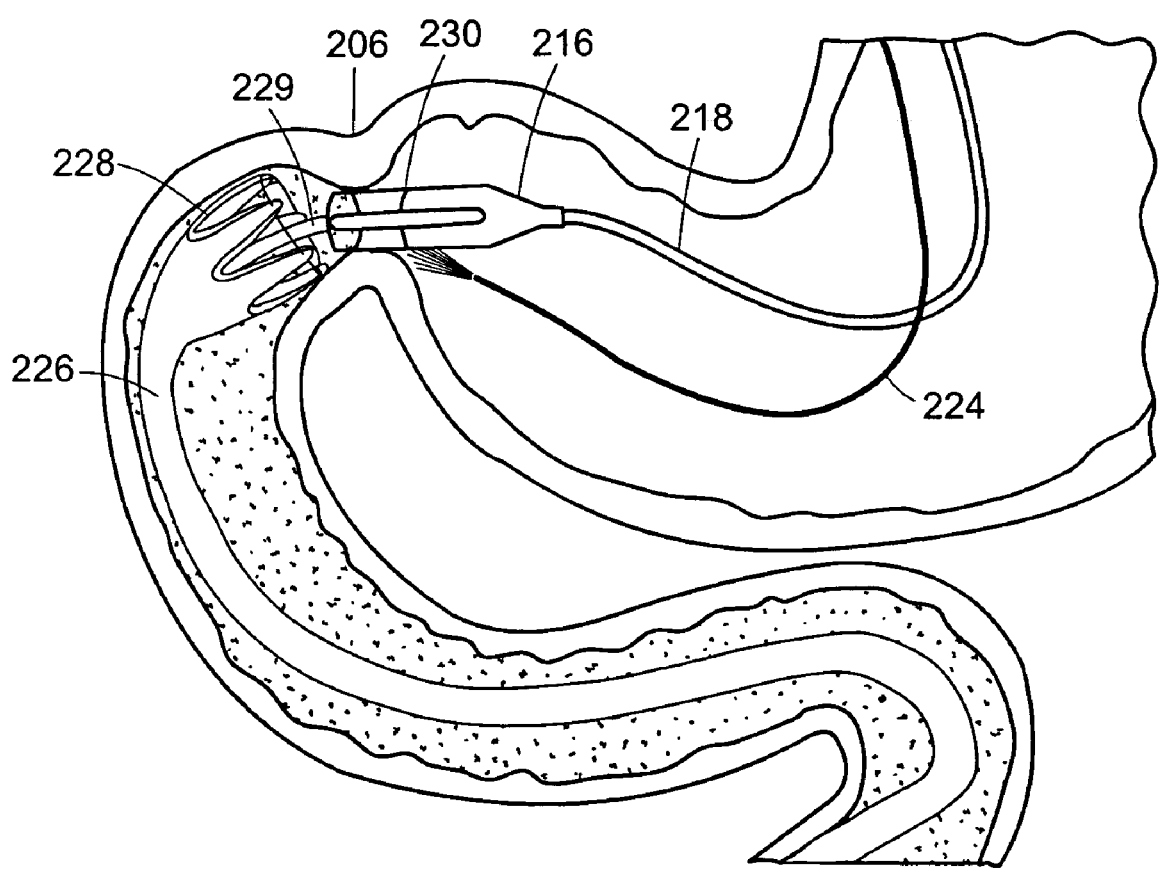
Figure 2T:
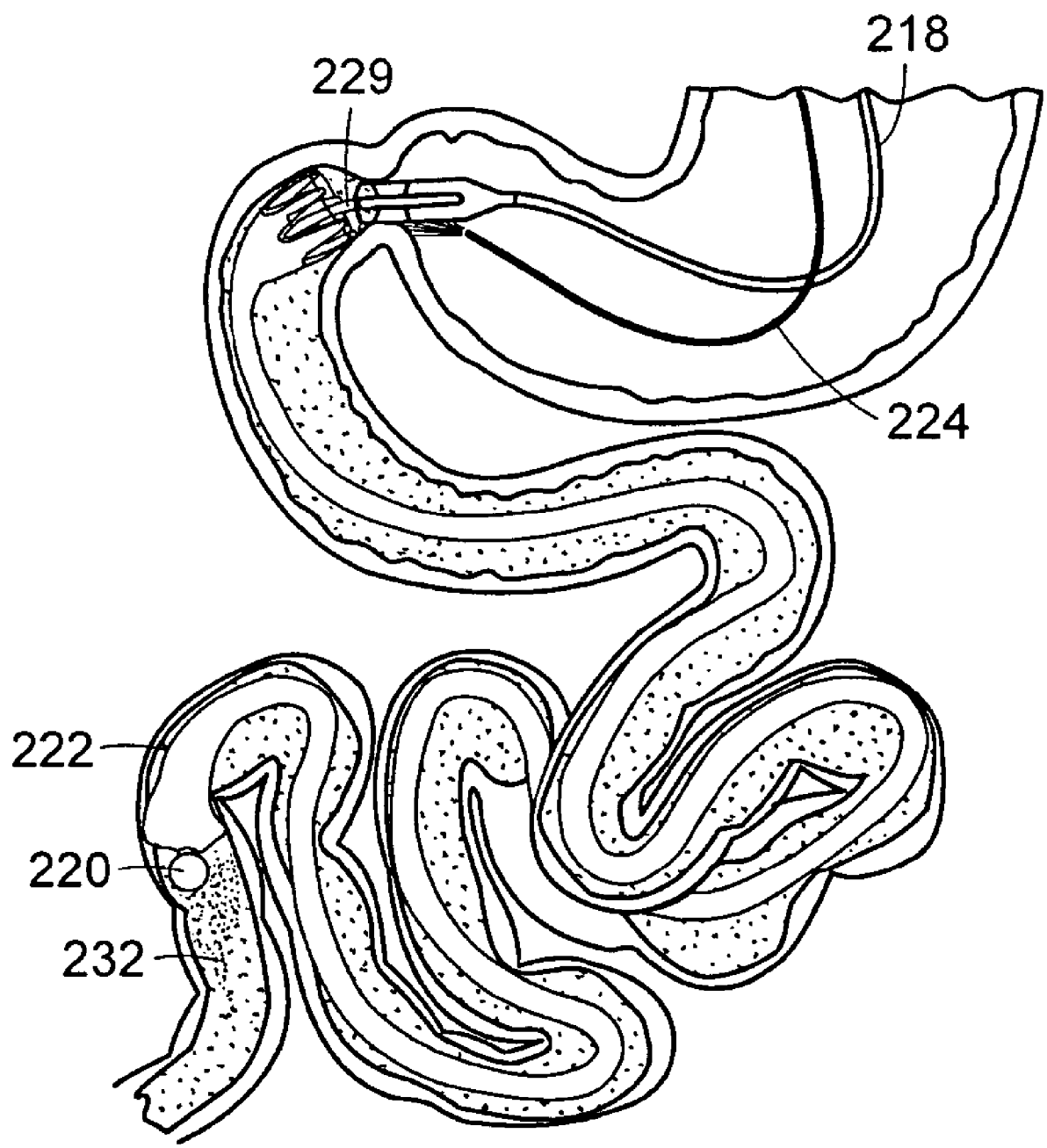
Figure 2U:
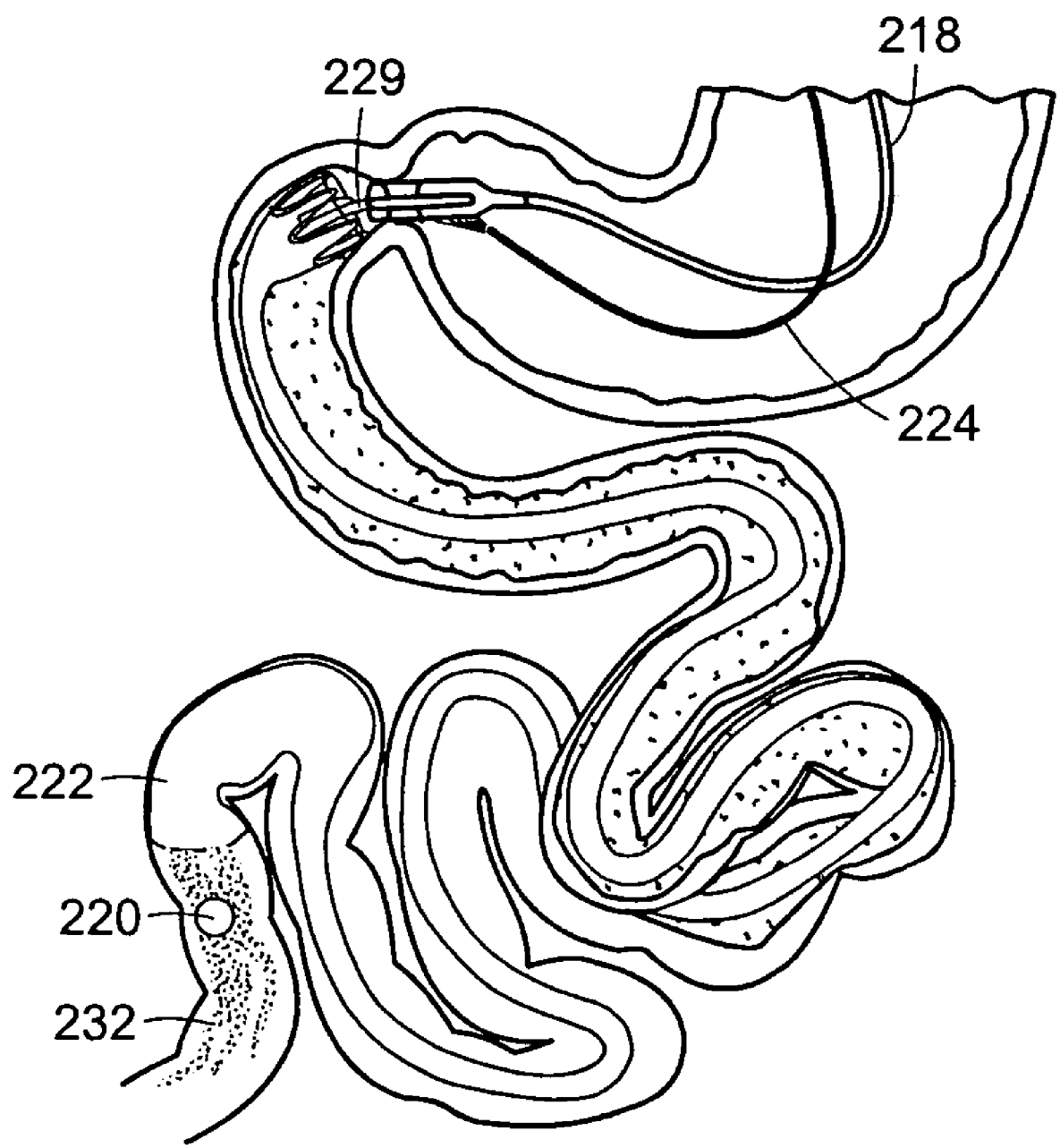
Figure 2V:
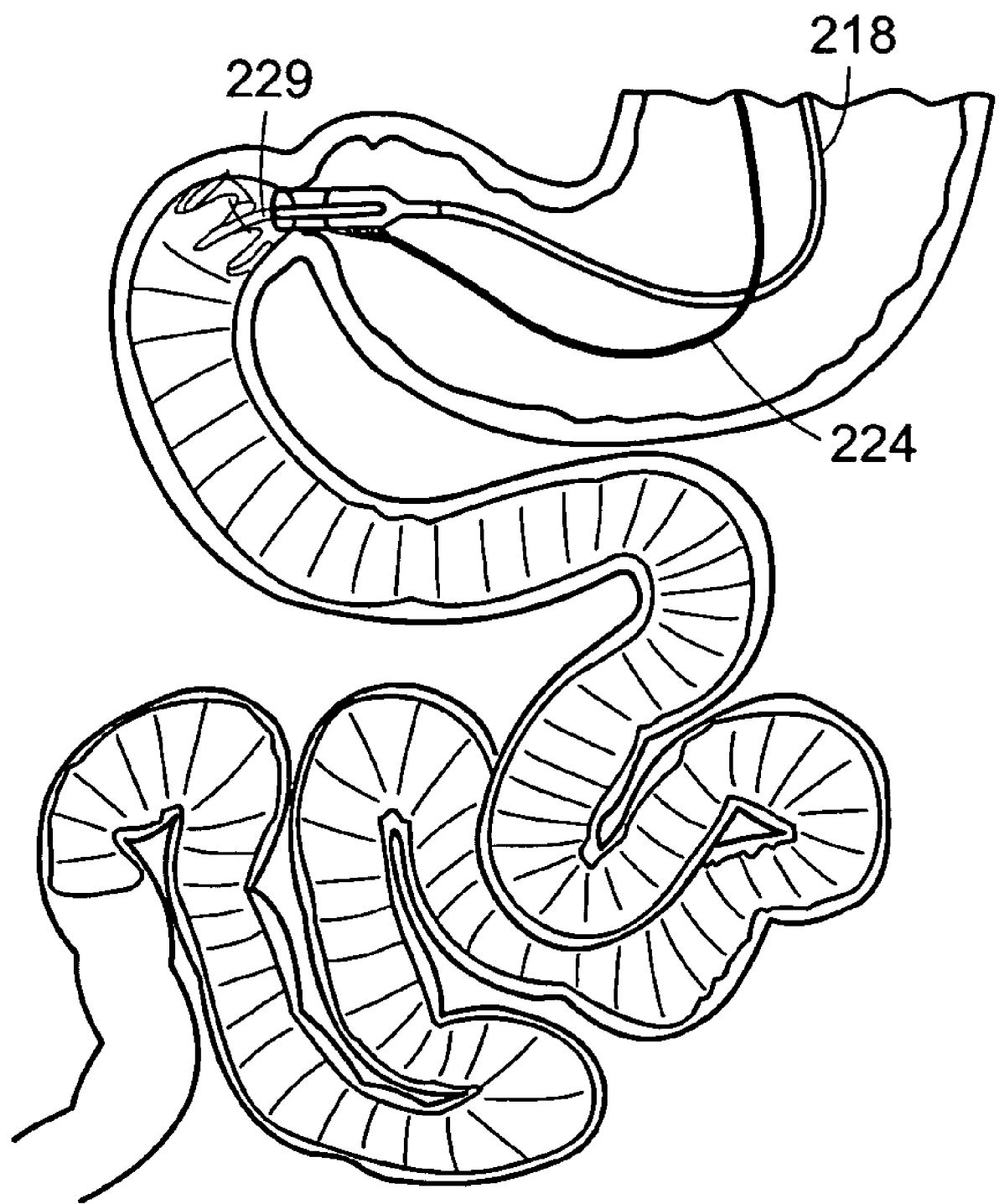
Figure 2W:
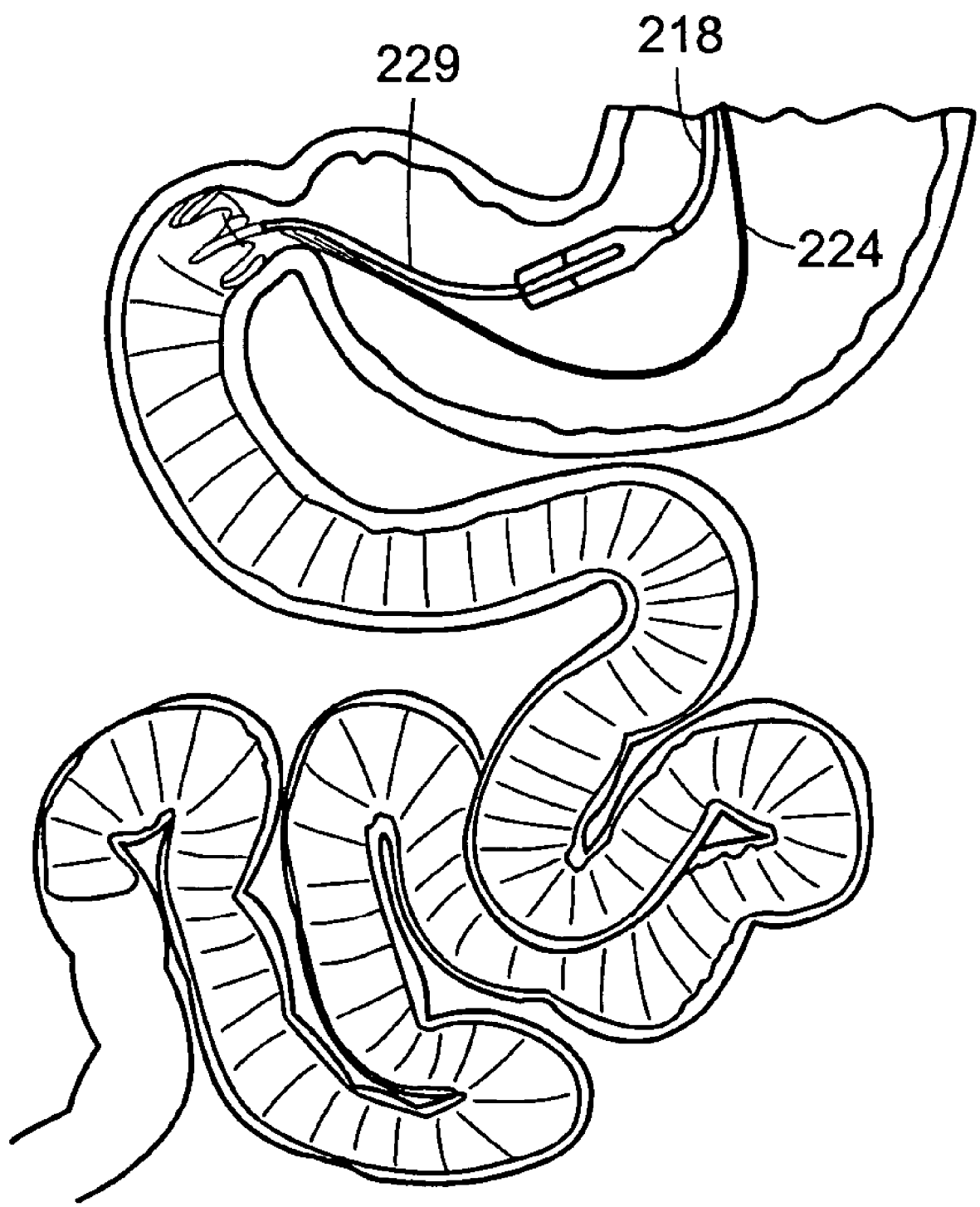
Figure 2X:
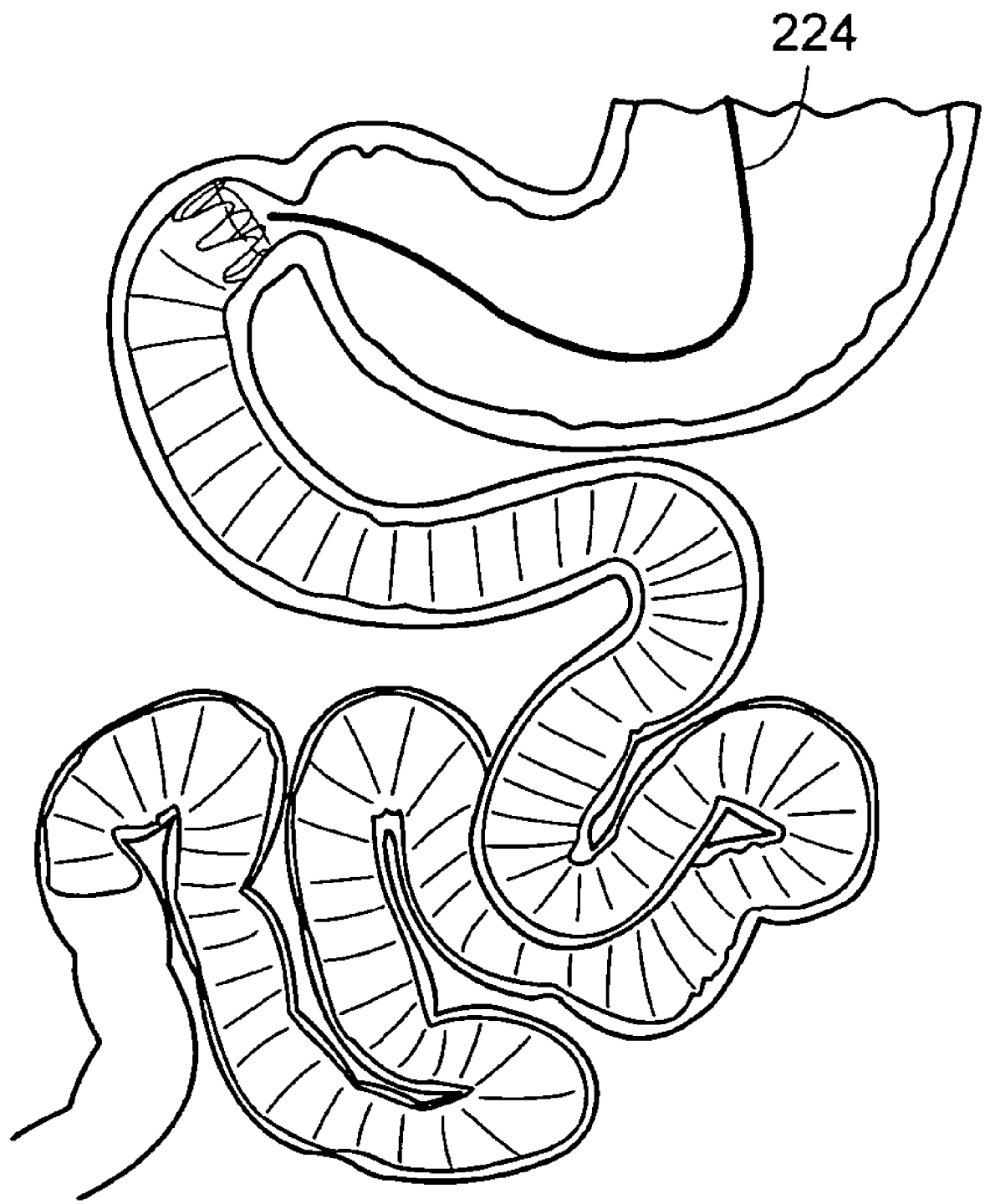
Figure 2Y:
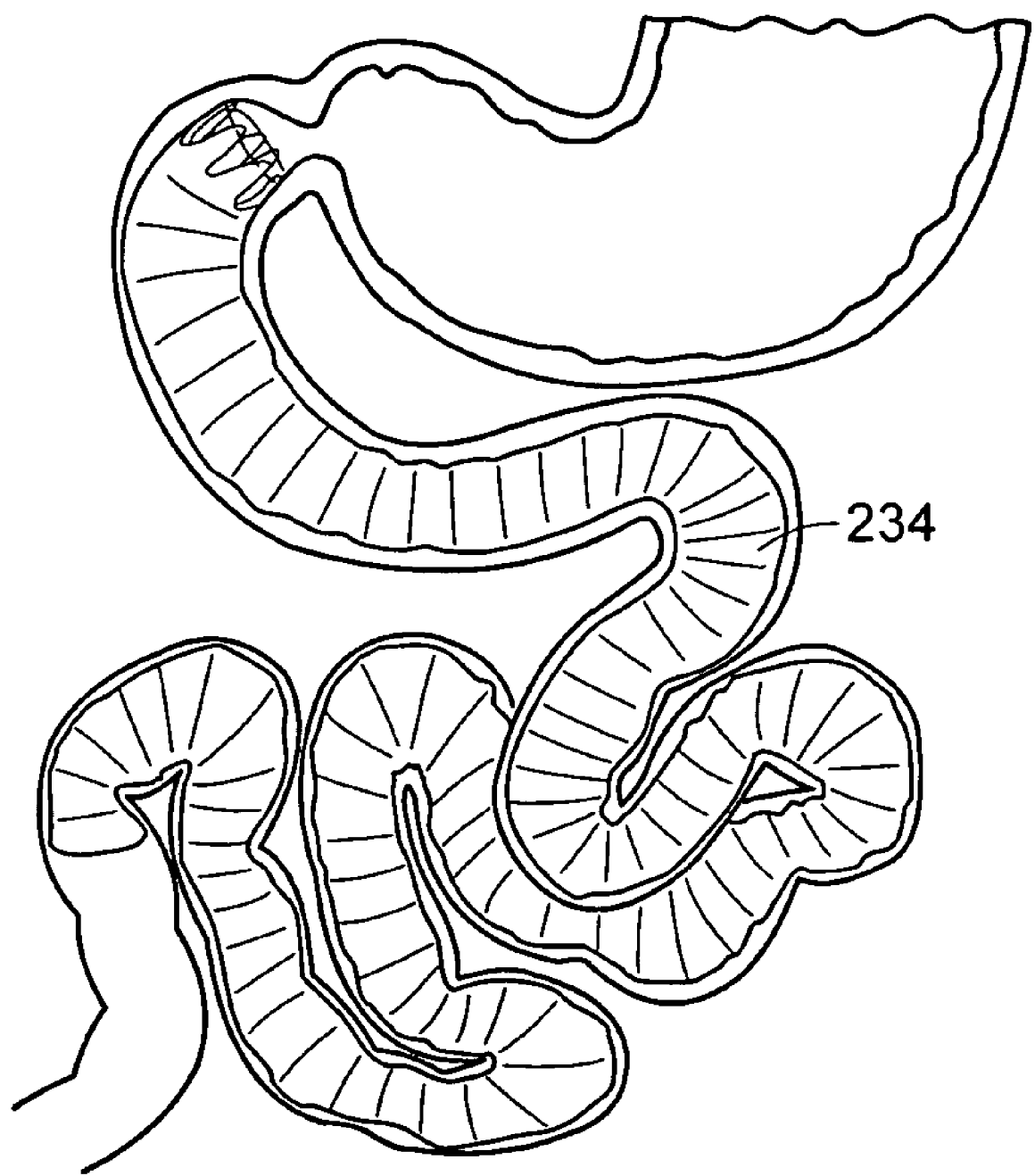

FIGS. 2A-2Y are a series of sequential diagrams illustrating multiple embodiments of methods of the invention. In FIG. 2A, gastro-scope 202 (e.g., a 9.8 millimeter endoscope) is directed through the mouth of a patient, and into stomach 204. Distal end 208 of gastro-scope 202 is directed through pyloric orifice 206 and into proximal duodenum 210, as illustrated in FIG. 2B.

Optionally, a proximal portion of the small intestine (e.g., the duodenum) is expanded in order to create a working space for the practitioner. One method of expanding a proximal portion of the small intestine is to direct a fluid into the duodenum via a working channel in the gastro-scope. Examples of suitable fluids include gases (e.g., air, nitrogen, and/or carbon dioxide) or liquids (e.g., water and/or saline). In some embodiments, the fluid is a liquid mixture of saline and a contrast medium. Examples of suitable contrast mediums include a fluorescent material, a radiopaque material, or a contrast medium commonly used for intravenous urography (e.g., preparations of diatrizoate sodium and diatrizoate meglumine). In still further embodiments, the liquid is a mixture of about 75% saline and about 25% Renografin™ (available from Bracco Diagnostics, Inc. Corporation, East Princeton, N.J.).

The exact amount of fluid needed to sufficiently expand the duodenum will depend on variables such as the size of the patient's gastrointestinal tract, the preferences of the practitioner, and/or the length of the gastrointestinal device to be delivered. In some embodiments, at least 60 milliliters of a fluid are used to expand the duodenum. In further embodiments, at least 200 milliliters of a fluid are used to expand the duodenum. 200 milliliters of a fluid would be useful for delivering, for example, a gastrointestinal sleeve that is about two feet in length. In further embodiments, at least 500 milliliters of a fluid are used to expand the duodenum. In still further embodiments, about 600 milliliters of a fluid are used to expand the duodenum which would be useful for delivering, for example, a gastrointestinal sleeve that is about 4 feet in length.

FIGS. 2C illustrates fluid 212 as it leaves distal end of 208 of gastro-scope 202. Optionally, the intestinal expansion process is monitored using fluoroscopy to ensure that the fluid is filling the intestines and not flowing proximally into the stomach. FIG. 2D illustrates the duodenum after it has been expanded to a desired extent with fluid 212.

After the small intestine has been expanded to the desired extent, a length of guidewire 214 is directed through the working channel of gastro-scope 202, out of the distal end 208, and into the proximal portion of the duodenum, as illustrated in FIG. 2E. An example of a suitable guidewire is about a 13-foot length of super-stiff 0.035 inch guidewire. Guidewire 214 is directed through gastro-scope 202 until the distal end of guidewire 214 forms loop 216 in the duodenum, as shown in FIG. 2F. Optionally, the presence and/or location of the loop is confirmed under fluoroscopy. Once a sufficient length of guidewire 214 is in the desired location, gastro-scope 202 can be removed while guidewire 214 is held in position.

Once the guidewire is in the desired location and the gastro-scope has been removed, a delivery catheter is directed into the duodenum, as illustrated in FIGS. 2G-2I. The leading or distal end of outer catheter 218 is attached, assembled to, or comprises a capsule or container assembly that includes capsule or container 216. Container 216 defines a guidewire lumen along its side. The proximal end of guidewire 214 is directed through the guidewire lumen, and catheter 218 is advanced or directed along guidewire 214 to a point distal from the pylorus and into a desired position in the gastrointestinal tract (e.g., a position distal to the pylorus in the proximal duodenum). Optionally, the location of capsule 216 is confirmed using fluoroscopy.

Alternatively, in some embodiments of the invention, the container assembly is advanced into the stomach and the guidewire is removed. A gastro-scope is used to direct the container assembly partially or entirely through the pylorus and into the small intestine.

Once container 216 is at the desired location in the duodenum, guidewire 214 can be removed from the gastrointestinal tract, as illustrated in FIGS. 2J and 2K. Optionally, prior to insertion, a lubricating jelly is applied to the surface of those portions of catheter 218 that are inserted into the gastrointestinal tract (e.g., container 216 and the distal portion of outer catheter 218).

The container holds or houses parts or all of a gastrointestinal implant device (e.g., a gastrointestinal sleeve). The gastrointestinal implant device includes a distal portion and a proximal portion. The distal portion includes a gastrointestinal sleeve and the proximal portion of the device includes an anchor for securing the device within the gastrointestinal tract (e.g., in the proximal duodenum). In some embodiments, the container holds or houses the proximal portion of the gastrointestinal device. In other embodiments, the container holds or houses both the distal and proximal portions. In still further embodiments, the container holds or houses the entire gastrointestinal device. Some or all of the sleeve portion can be folded and stored in the container with the anchor.

After container 216 is at the desired location in the proximal duodenum, a distal portion 222 of the sleeve is removed from the container and directed into a location in the gastrointestinal tract that is distal from the container, as illustrated in FIGS. 2L-2P. Outer catheter 218 defines an inner catheter lumen (not illustrated in FIGS. 2L-2P) and an inner catheter (not illustrated in FIGS. 2L-2P), to which ball 220 is releasably attached, is directed through the inner catheter lumen and into locations of the gastrointestinal tract that are distal from container 216 and pylorus 206.

Distal portion 222 of the sleeve is releasably secured to the leading or distal portion of the inner catheter so that as the inner catheter is advanced through the distal intestine, distal portion 222 is also advanced. In this manner, distal portion 222 is directed to locations in the gastrointestinal tract that are distal from container 216 and into the distal intestines (e.g., into the jejunum).

As the inner catheter is advanced through the inner catheter lumen and into the distal intestine, the proximal portion (not illustrated in FIGS. 2L-2P) of outer catheter 218 is held in place to ensure that capsule 216 remains in the duodenum and does not move proximally into the stomach. The proximal portion of the gastrointestinal sleeve (not illustrated in FIGS. 2L-2P) is releasably secured or attached to container 216 by a locking means (e.g., by an anchor locking wire) to ensure that the anchor does not emerge from container 216 and deploy before the distal portion 222 of the sleeve is extended to a desired location in the distal intestines.

The distal end of the inner catheter includes or is attached to an atraumatic tip (e.g., atraumatic ball 220), which minimizes or eliminates tissue trauma as the inner catheter is advanced into the distal intestines. The exact location to which distal portion 222 is advanced into the distal intestines will vary with the needs of the patient and the demands of the given procedure. The inner catheter also includes a stiffening wire that provides sufficient linear or column strength to the inner catheter to facilitates navigation of the distal intestines. Optionally, fluoroscopy is used to track the progress of the advancement.

After the desired length of sleeve has been delivered, endoscope 224 is optionally directed into the stomach to visually inspect the proximal end of delivery capsule 216 to ensure that it is in the desired position and/or to monitor the subsequent anchor deployment process, as illustrated in FIGS. 2O and 2P. Optionally, the inner catheter includes markings which are useful for monitoring the advancement of the inner catheter. For example, the outer wall of the inner catheter can include a series of indicia which the practitioner can view as he slides portions of the inner catheter into and out of the outer catheter. In addition or alternatively, the inner catheter can include one or more radiopaque markings that can be viewed on an x-ray image or one or more markings that are visible via fluoroscopy.

After the distal portion of the sleeve is advanced to a desired location in the distal intestines, the anchor is deployed from the container and secured to a desired position within the gastrointestinal tract, as illustrated in FIGS. 2Q-2S. The anchor locking means (not illustrated in FIGS. 2Q-2S) is released to allow the anchor to be subsequently removed from container 216. For example, the anchor locking means can include a locking wire that releasably secures the anchor within container 216 and pulling the locking wire proximally detaches the anchor so that the anchor can be removed from the container at some subsequent time.

Container 216 includes visual marker 230 (e.g., a black ring) that can be used to determine if the capsule is in a desired location before anchor 228 is fully removed from container 216 and secured at a desired location in the gastrointestinal tract. For example, delivery catheter 218 is pulled proximally until visual marker 230 is proximal to pylorus 206 and visible in the stomach to endoscope 224. In this manner, the practitioner can ensure that the anchor will deploy at the desired anchoring position when it is removed from container 216.

Once container 216 is in the desired location, outer catheter 218 is held in position and the inner catheter is advanced further distally to pull the sleeve and anchor 228 from container 216. Optionally, the anchor is pushed out of the container using a means for displacing an anchor from the container assembly (e.g., an anchor plunger).

As shown in FIGS. 2Q-2S, anchor 228 is removed from container 216 and deployed, thereby securing the proximal portion of the device in the gastrointestinal tract (e.g., at the duodenal bulb). For example, anchor 228 can secure the device with the use of barbs which extend into the muscle tissue of the proximal duodenum.

After anchor 228 is deployed and the device secured within the gastrointestinal tract, endoscope 224 is optionally removed and/or the stiffening wire is pulled proximally through a main stiffening wire lumen defined by inner catheter 229 and removed from the gastrointestinal tract. After the stiffening wire has been removed, the sleeve is optionally expanded or inflated by directing fluid through the main stiffening wire lumen defined by inner catheter 229, as illustrated in FIG. 2T. The fluid causes a distal portion 222 of sleeve to expand and separate or disengage the distal portion of inner catheter 229, as illustrated in FIG. 2U. Suitable fluids include those discussed previously for use in expanding the duodenum. For example, the sleeve can be inflated by directing at least 180 milliliters of a saline solution or a dilute Renografin™/saline solution. Atraumatic ball 220 and distal portion 222 are released from the inner catheter by pulling the locking wire (not illustrated in FIGS. 2Q-2S) proximally until a release mark on the wire is visible at the proximal end of outer catheter 218.

Inner catheter 229 and outer catheter 218 are removed, as illustrated in FIGS. 2V and 2W. Optionally, the position of the device can be monitored with fluoroscopy while inner catheter 229 and outer catheter 218 are removed from the gastrointestinal tract. Atraumatic ball 220 is moved distally via natural peristalsis and is excreted from the gastrointestinal tract.

Optionally, the endoscope is positioned across the pylorus and a fluid (e.g., a gas or liquid, such as air, nitrogen, carbon dioxide, saline, or dilute Renografin™) is directed into the duodenum to confirm patency of the sleeve, as illustrated in FIG. 2X. The endoscope is subsequently removed. FIG. 2Y illustrates gastrointestinal device 234 placed in the gastrointestinal tract.

Figure 3A:
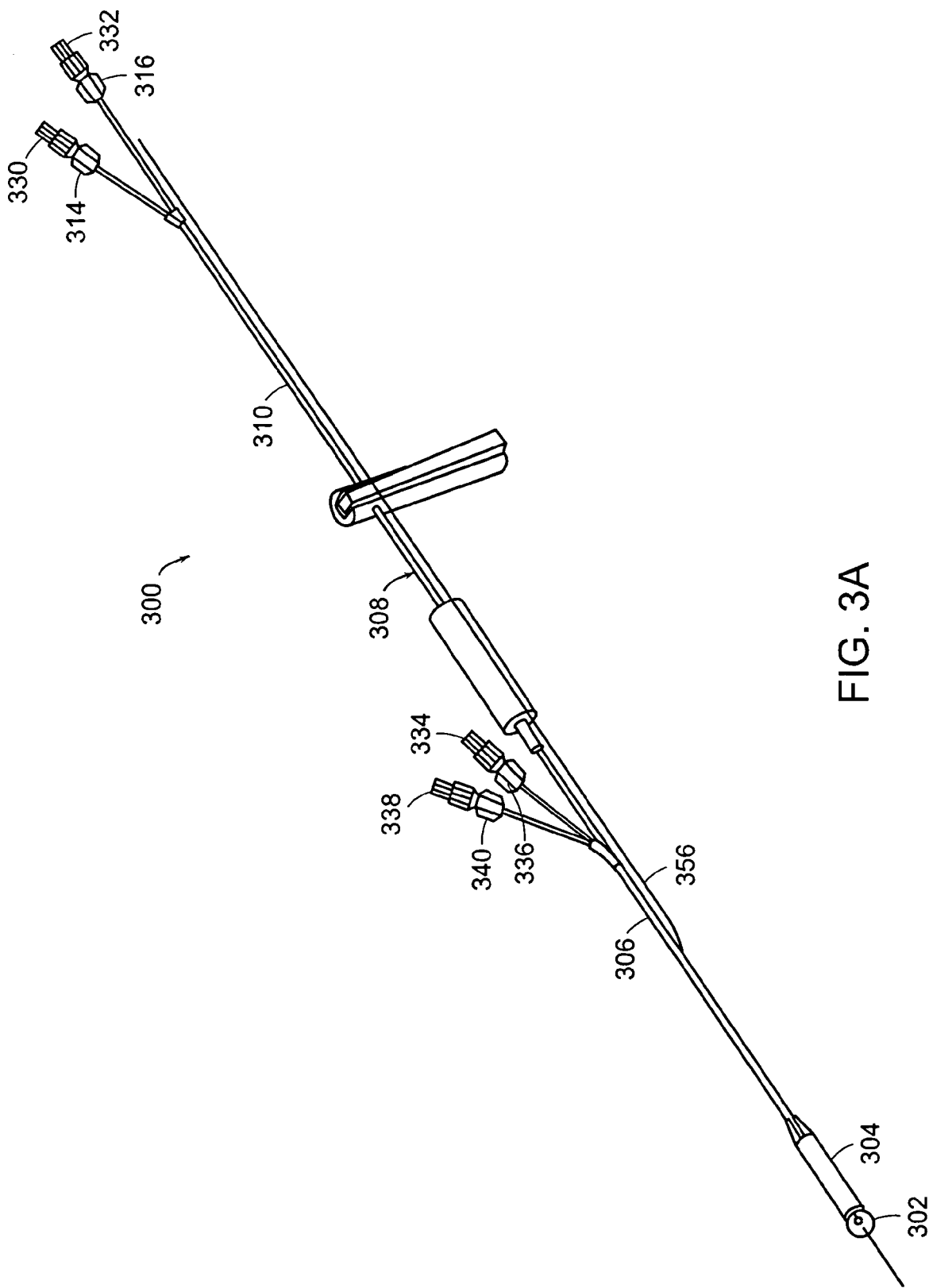
FIGS. 3A-3H illustrates multiple embodiment of this invention that includes a schematic view of assembled delivery catheter systems for delivery of gastrointestinal implant devices (e.g., gastrointestinal sleeves).

In some embodiments of the invention, the gastrointestinal implant devices are implanted via catheter-based placements methods (e.g., within endoluminal catheter). FIGS. 3A-3H illustrates multiple embodiments of this invention that include schematic views of various aspects of assembled delivery catheter system 300 for delivery of a gastrointestinal implant device (e.g., a gastrointestinal sleeve). As shown in FIG. 3A, delivery catheter system 300 includes an atraumatic tip comprising atraumatic ball 302, a container assembly that includes capsule or container 304, outer catheter 306, inner catheter pusher 308, and inner catheter 310.

Inner and outer catheters 310, 306 and container 304 are made from materials commonly used to form catheters. For example, inner catheter 310 can be made of a polyether block amide (e.g., Pebax® 7233, available from Arkema Group, Paris, France). In some embodiments, outer catheter 306 is made of high density polyethylene and/or container 304 is made of hard plastic (e.g., acetal or polycarbonate). Preferably, catheters 310, 306 are made from materials having frictional properties that facilitate the movement of catheter 310 relative to catheter 306 and facilitate the movement of inner catheter 310 and container 304 in the gastrointestinal tract.

Figure 3B:
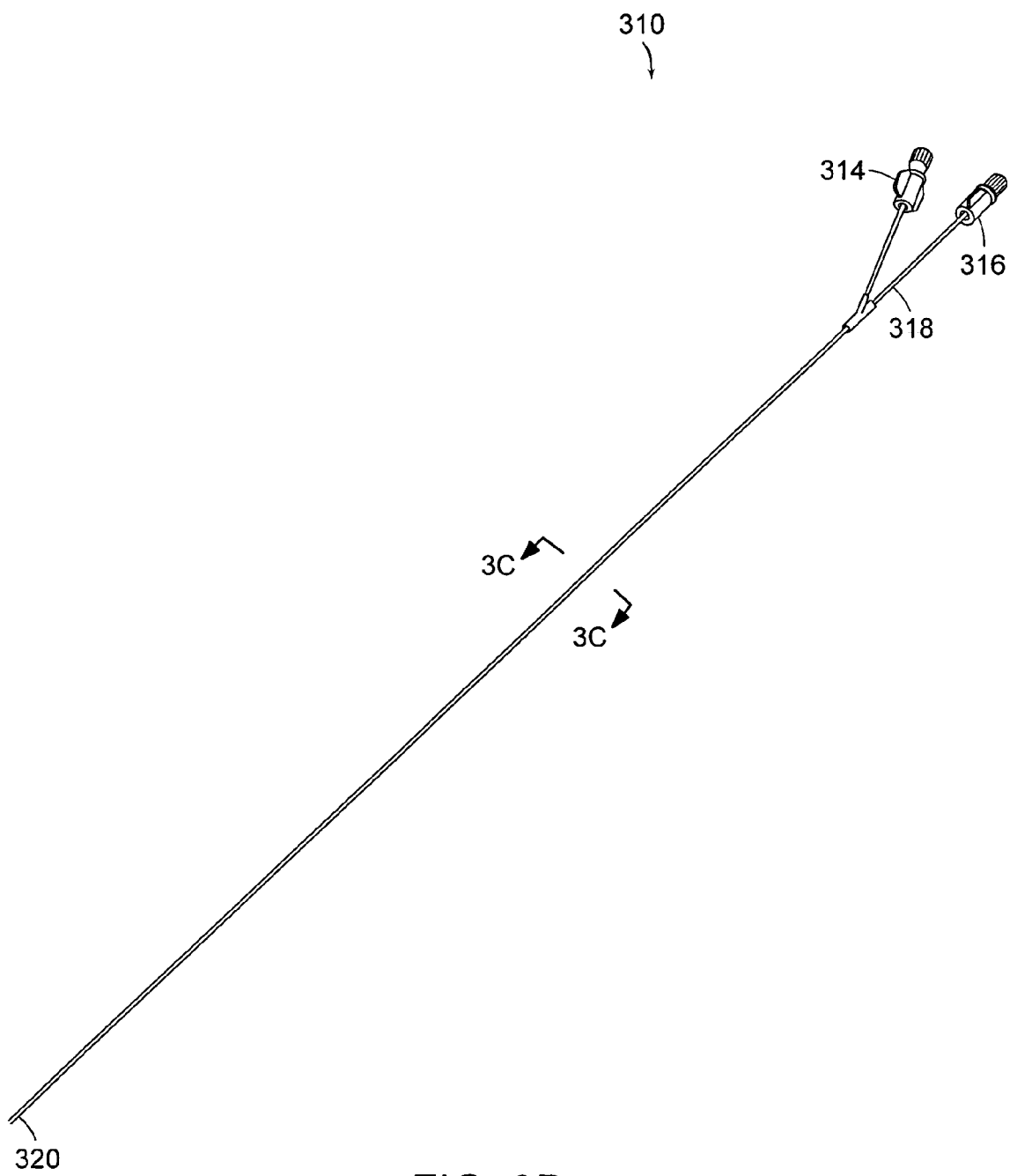
Figure 3C:
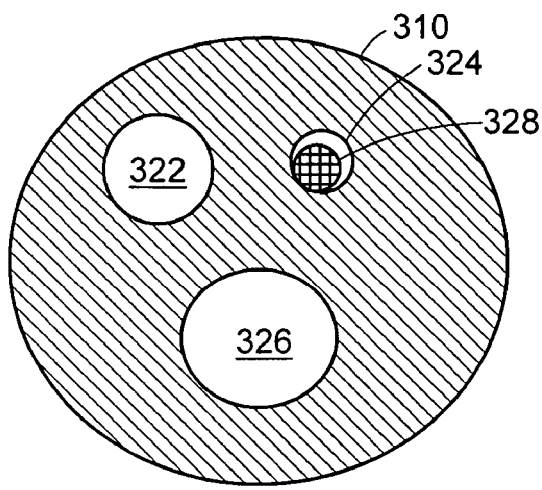

FIG. 3B illustrates a schematic diagram of inner catheter 310. Inner catheter 310 includes atraumatic ball locking wire port 314 and stiffening wire port 316 at proximal end 318. FIG. 3C illustrates a cross-sectional view taken along lines A-A of FIG. 3B through one section of inner catheter 310 that is between proximal end 318 and distal end 320. Inner catheter 310 defines ball locking wire lumen 322, tension wire lumen 324, and stiffening wire lumen 326. Locking wire lumen 322 and stiffening wire lumen 326 extend along the length of, and within, inner catheter 310. Locking wire lumen 322 extends from ball locking wire port 314 to distal end 320. Stiffening wire lumen 326 extends along the length of, and within, inner catheter 310, from stiffening wire port 316 to distal end 320. Tension wire 328 is located within tension wire lumen 324. The distal and proximal ends of tension wire 328 are attached to the inner walls of tension wire lumen 324, thereby securing tension wire 328 within inner catheter 310. For example, tension wire 328 can be attached to the inner walls of tension wire lumen 324 with adhesives, heat setting, or via coextruding inner catheter 310 and tension wire 328. Tension wire 328 provides structural support to inner catheter 310. For examples, tension wire 328 can prevent catheter 310 from undergoing undesired stretching or elongating.

Turning back to FIG. 3A, system 300 includes ball locking wire knob 330 and stiffening wire knob 332. Ball locking wire knob 330 extends from ball locking wire port 314 to distal end 302 via ball locking wire lumen 322 (illustrated in FIG. 3C) defined by inner catheter 310. Stiffening wire knob 332 extends from stiffening wire port 316 to distal end 302 via stiffening wire lumen 326 (illustrated in FIG. 3C) defined by inner catheter 310.

Figure 3E:
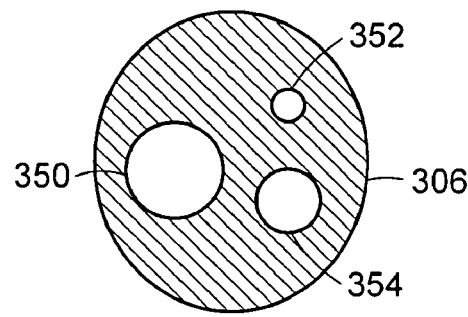
Figure 3H:
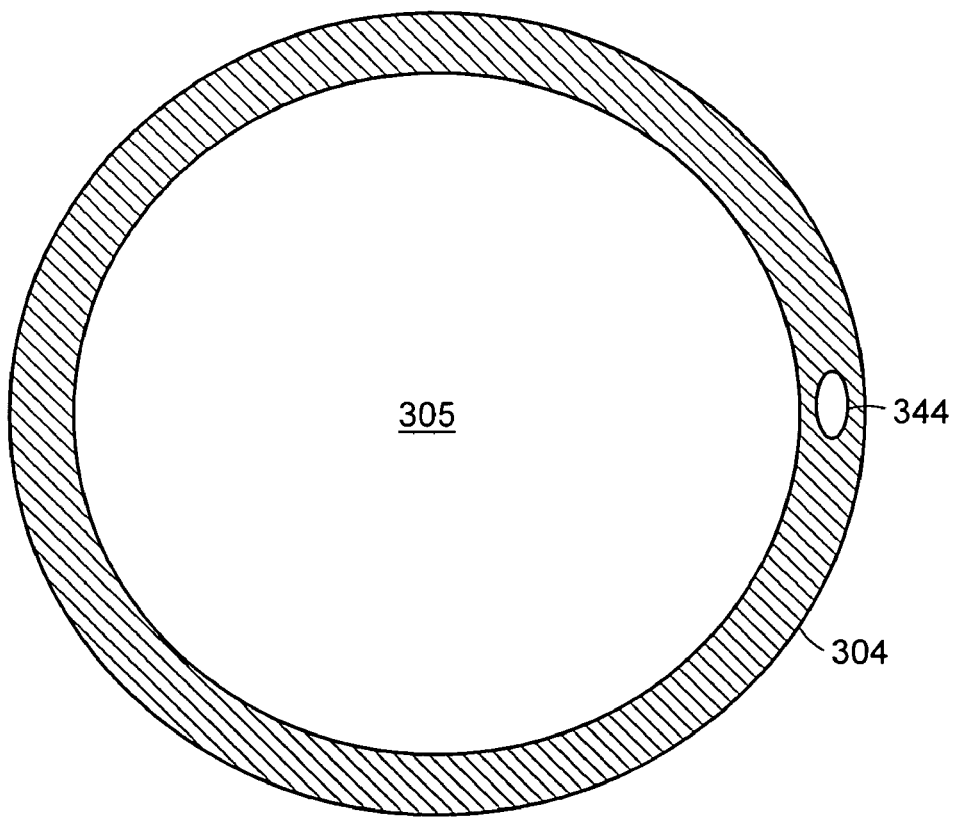
Figure 3D:
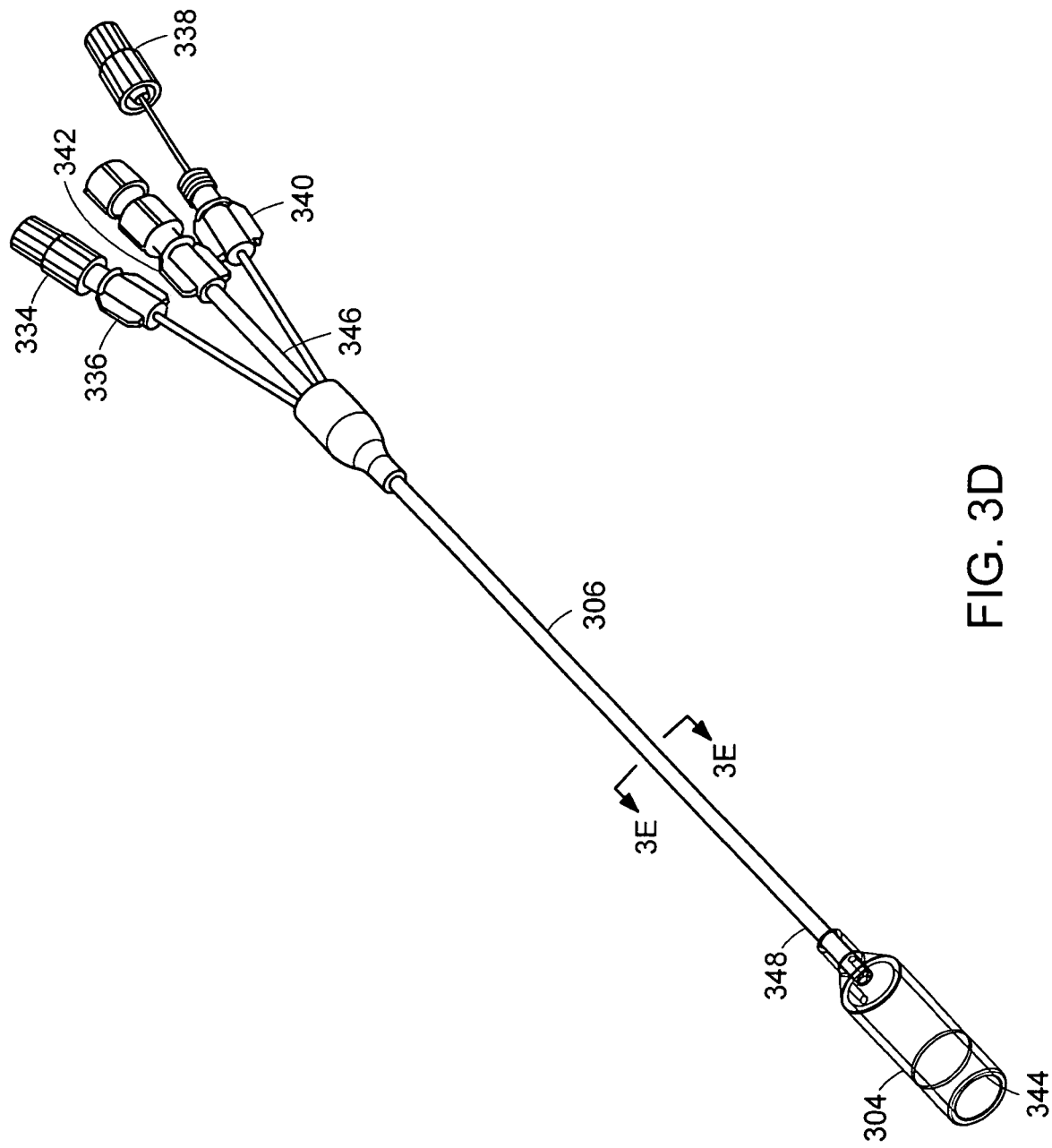

FIG. 3D illustrates a schematic diagram of outer catheter 306 and container 304. Container 304 defines guidewire lumen 344. Guidewire 356 (illustrated in FIG. 3A) extends along inner and outer catheters 310, 306 and through container 304 via guidewire lumen 344.

Outer catheter 306 includes anchor locking wire port 336, anchor plunger port 340, and attachment port 342 at proximal end 346. FIG. 3E illustrates a cross-sectional view taken along lines B-B of FIG. 3D through one section of outer catheter 306 that is between proximal end 346 and distal end 348. Outer catheter 306 defines inner catheter lumen 350, anchor locking wire lumen 352, and anchor plunger lumen 354. Anchor locking wire lumen 352 extends along, and within, outer catheter 306, from anchor locking wire port 336 to distal end 348. Anchor plunger lumen 354 extends along, and within, outer catheter 306, from anchor plunger port 340 to distal end 348.

Turning back to FIG. 3A, system 300 includes anchor locking wire 334, a means for displacing an anchor from the container assembly that includes anchor plunger 338, and guidewire 356. Anchor locking wire 334 extends from anchor locking wire port 336 to container 304 via anchor locking wire lumen 352 (illustrated in FIG. 3E) defined by outer catheter 306. Anchor plunger 338 extends from anchor plunger port 340 to container 304 via anchor plunger lumen 354 (illustrated in FIG. 3E) defined by outer catheter 306.

Figure 3F:
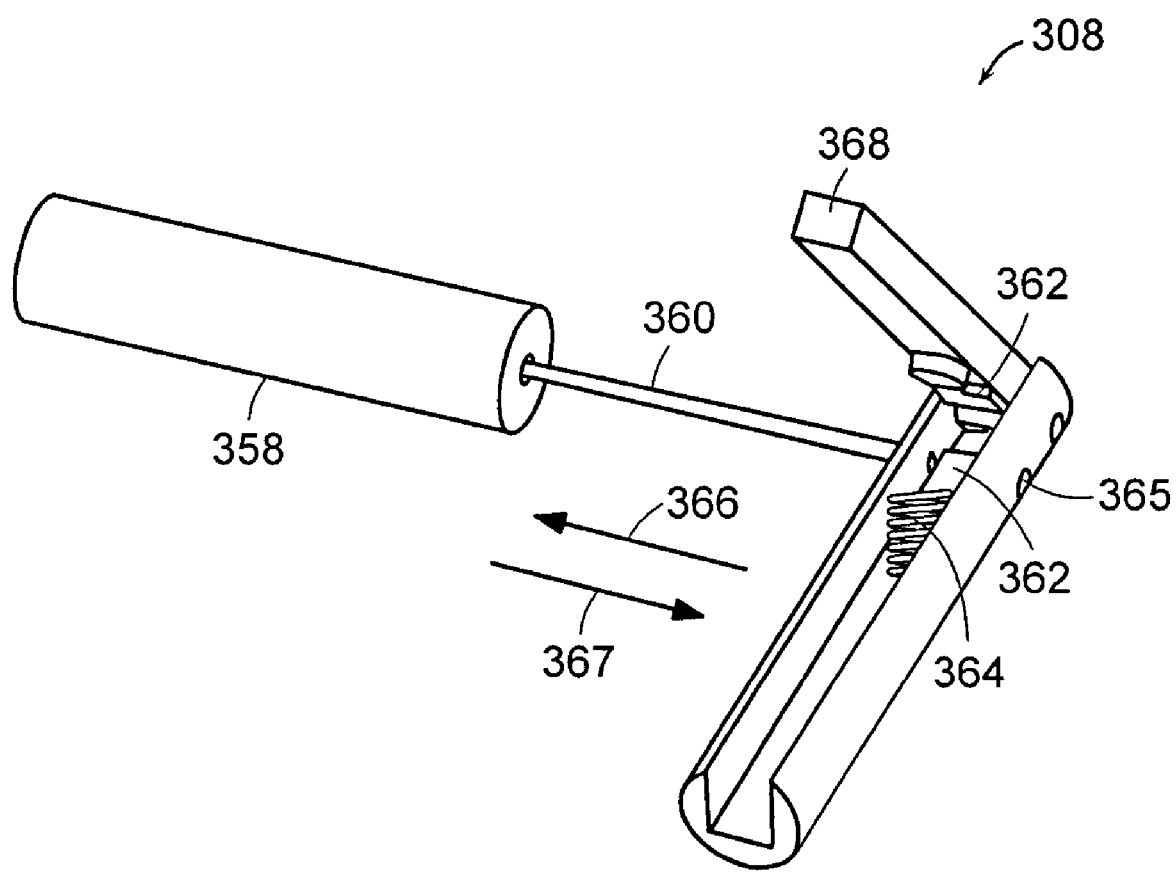

System 300 includes inner catheter pusher 308. Inner catheter pusher 308 is assembled or attached to outer catheter 306. FIG. 3F illustrates a schematic view of inner catheter pusher 308. Pusher 308 includes pusher handle 358, slide tube 360, and locking handle 368. Pusher handle 358 assembles or attaches pusher 308 to outer catheter 306 (as illustrated in FIG. 3A), thereby connecting pusher 308 to outer catheter 306. Pusher 308 defines inner catheter orifice 365, and a slide tube lumen that extends through handle 358, slide tube 360, and locking handle 368. Locking handle 368 is attached to slide tube 360 and includes inner catheter locking pads 362 and handle return spring 364. When assembled in system 300, inner catheter 310 extends through slide tube 360 and handle 368 via orifice 365 and the slide tube lumen.

In operation, depressing locking handle 368 causes locking pads 362 to securely grip a portion of inner catheter 310 relative to handle 368 and slide tube 360. Applying force in direction 366 while handle 368 is depressed moves handle 368, tube 360, and inner catheter 310 relative to handle 358, thereby directing a length of inner catheter 310 into the inner catheter lumen defined by the outer catheter. After pressure is released from handle 368, handle return spring 364 causes locking pads 362 to disengage from inner catheter 310. Once disengaged from inner catheter 310, handle 368 is moved along direction 367, and the process can then be repeated. In this manner, inner catheter 310 can be advanced distally through inner catheter lumen 350 defined by outer catheter 306. Slide tube 360 provides rigid support to inner catheter 310 to prevent inner catheter 310 from kinking during advancement.

Figure 3G:
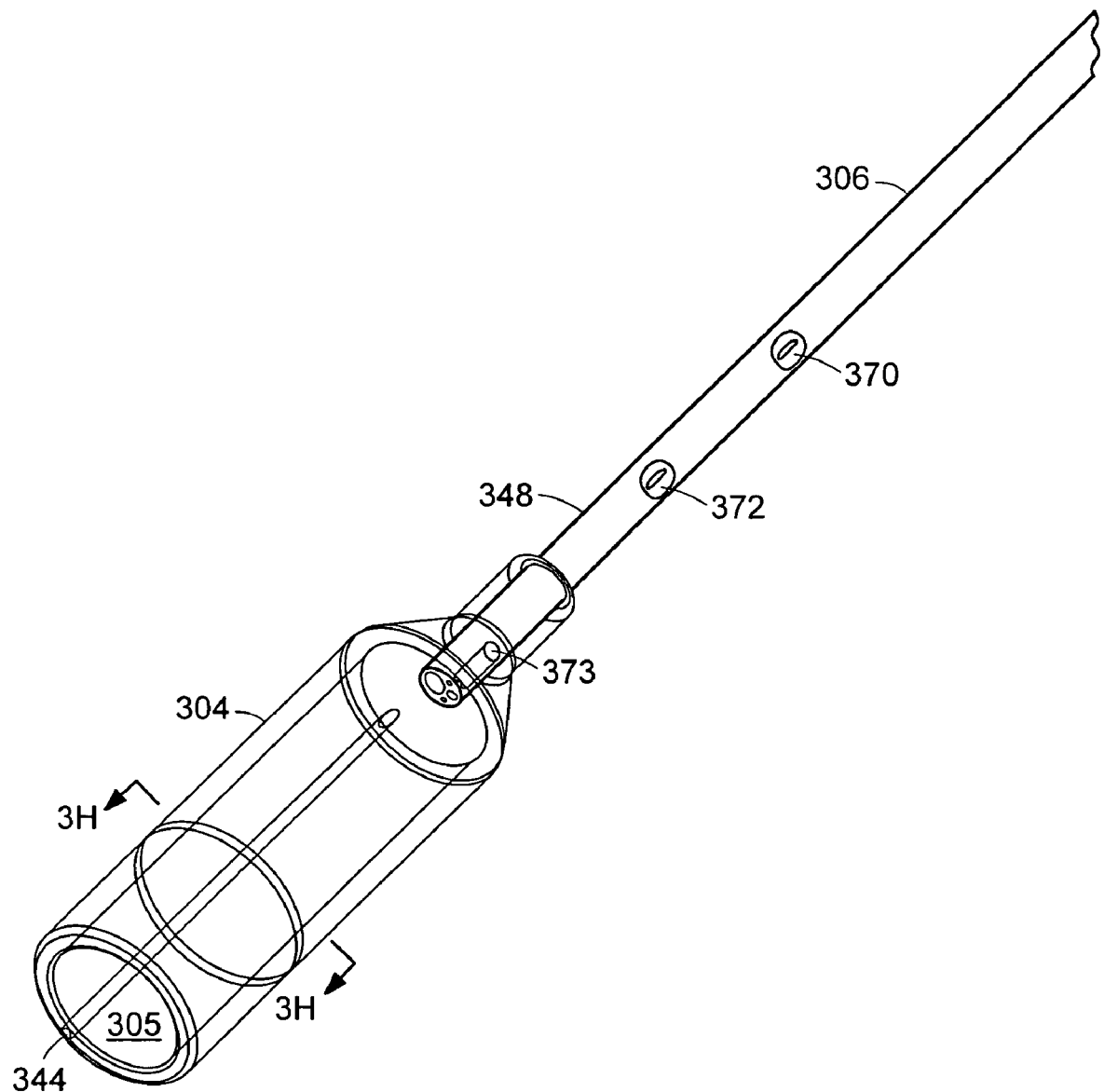

FIG. 3G illustrates a schematic diagram of a portion of system 300 that includes outer catheter 306 and container 304. Container 304 defines guidewire lumen 344 and is assembled or attached to distal end 348 of outer catheter 306. Container 304 also defines anchor locking wire port 373. Catheter 306 defines anchor locking wire ports 370 and 372 which intersect with anchor locking wire lumen 350 (not illustrated in FIG. 3G for clarity) defines by outer catheter 306. Optionally, interior walls of container 304 are lined with metal (e.g., with a steel liner). FIG. 3H illustrates a cross-sectional view taken along lines C-C of FIG. 3G through one section of container 304. Container 304 defines guidewire lumen 344 as well as inner chamber 305.

FIGS. 4A-4L illustrate additional embodiments of the present invention that include gastrointestinal implant delivery catheter system 400 and a method of use. For purposes of clarity, FIGS. 4A-4L do not illustrate the various parts and portions of a mammalian gastrointestinal tract.

System 400 includes an atraumatic tip comprising atraumatic ball 402, a container assembly that includes capsule or container 404, outer catheter 406, inner catheter pusher 408, inner catheter 410, and guidewire 412.

In some embodiments of this invention, system 400 is used to place or install a gastrointestinal implant device (e.g., a gastrointestinal sleeve) into the digestive tract of a mammal. Briefly, a gastrointestinal sleeve is releasably secured to the distal end of inner catheter 410 with a locking wire and then the sleeve and an anchor portion is placed or stored within container 404 of a container assembly. Guidewire 412 is directed into a desired location within a gastrointestinal tract of a mammal (e.g., in a proximal portion of the small intestine). After guidewire 412 is in the desired location, container 404 is directed along the guidewire into a desired location within the mammal's gastrointestinal tract (e.g., the duodenum). The distal end of inner catheter 410, along with the secured portion of the gastrointestinal sleeve, is advanced within the gastrointestinal tract to a location that is distal from container 404, thereby extending or unfurling at least a portion of the gastrointestinal sleeve. During some or all of the unfurling portion of the procedure, the anchor and the proximal portion of the sleeve is releasably secured within the container assembly with a locking wire. Once the sleeve has been extended to the desired extent (e.g., into the jejunum), the anchor portion is unlocked from the container assembly and removed from the container. The anchor can be removed from container 404 by, for example, again advancing inner catheter 410 and the releasably secured distal end of the sleeve, thereby pulling the unlocked anchor from container 404. Optionally, the anchor is removed from container 404 with the use of a means for displacing an anchor from the container assembly that includes anchor plunger 411. The anchor is secured at desired location within the gastrointestinal tract of the mammal (e.g., in the duodenum). Any portion of the gastrointestinal implant device that is still secured to system 400 is detached, and the system is removed from the mammal.

Figure 4A:
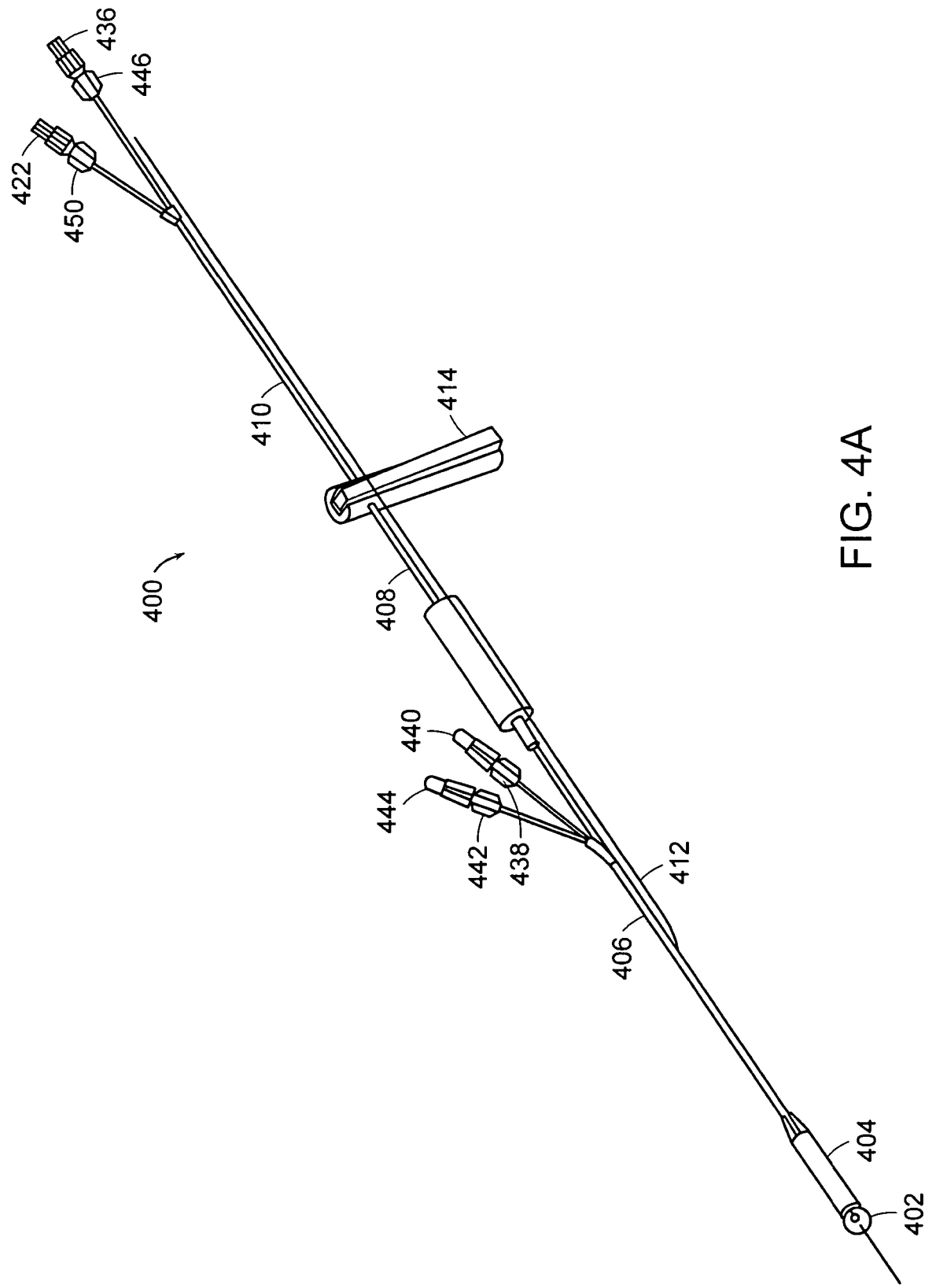

FIG. 4A illustrates system 400 with a gastrointestinal sleeve (not visible in FIG. 4A) stored within a container assembly that includes container 404. The sleeve includes a distal portion and a proximal portion. The proximal portion of the sleeve includes an anchoring device for securing the sleeve to a location within the gastrointestinal tract of a mammal. The anchor is placed or stored within a chamber defined by container 404. Some or all of the sleeve is folded and stored within the chamber as well. The distal portion of the sleeve is releasable secured to the distal end of inner catheter 410, and the anchor is releasably secured to container 404.

After the distal end of guidewire 412 is directed to a desired location within the gastrointestinal tract of a mammal, the proximal end of guidewire 412 is directed through a guidewire lumen defined by container 404. Once assembled to guidewire 412, outer catheter 406 is advanced to direct container 404 along guidewire 412 and to a desired location within the gastrointestinal tract of the mammal. After container 404 has been advanced to the desired location, guidewire 412 is removed from the gastrointestinal tract of the mammal. FIGS. 2E-2K illustrate advancement of a container along a guidewire and into the gastrointestinal tract of a mammal.

Figure 4B:
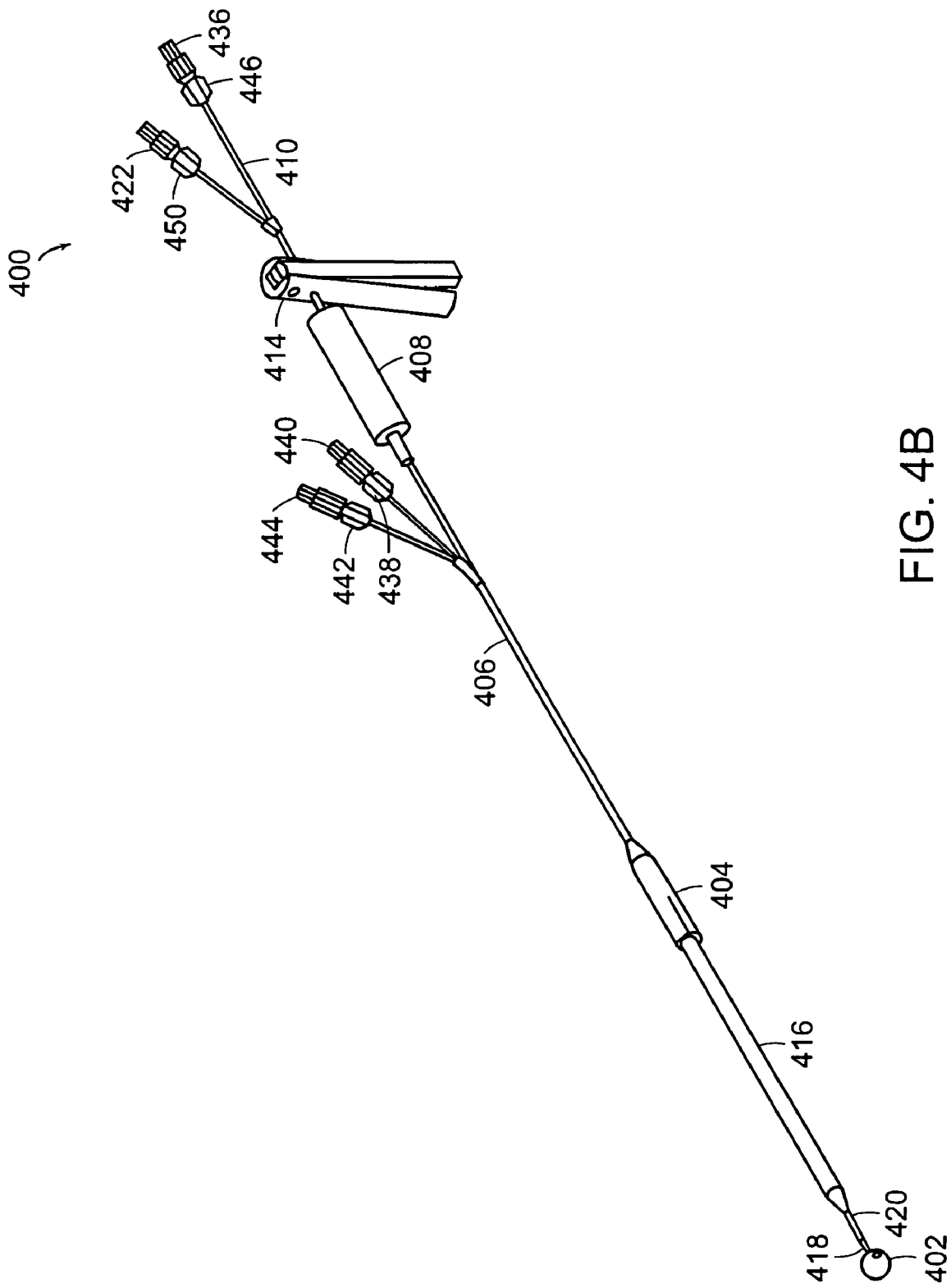

Inner catheter pusher 408 is used to direct a distal end of inner catheter 410 into a desired location in the gastrointestinal tract that is distal to container 404. Locking handle 414 is depressed, thereby causing the pads (not illustrated in FIG. 4A) of pusher 408 to securely grip inner catheter 410. Handle 414 is slid distally, thereby directing a length of inner catheter 410 into the inner catheter lumen (not illustrated in FIG. 4A) defined by outer catheter 406 and causing the distal end 418 of inner catheter 410 to emerge from the distal end of container 404, as shown in FIG. 4B. Distal portion 420 of sleeve 416 is attached to distal end 418 of inner catheter 410 and is advanced with the inner catheter (FIGS. 2L-2P illustrate advancement of an inner catheter and a distal portion of a sleeve). Locking handle 414 is released and the process repeated until a desired length of inner catheter 410 and intestinal sleeve 416 has been advanced. FIG. 4B illustrates system 400 after a length of sleeve 416 has been advanced.

In some embodiments, the inner catheter includes an atraumatic tip (e.g., a releasable or deflatable atraumatic ball tip) which facilitates the advancement of the inner catheter through the gastrointestinal tract (e.g., through the proximal intestines). The atraumatic tip allows the inner catheter to be advanced through a gastrointestinal tract, while reducing or eliminating damage or irritation to tissue. The atraumatic tip guides the inner catheter through the distal intestines. The atraumatic ball is in the range of between about 5 millimeters and about 20 millimeters. Preferably, the ball tip is in the range of between about 6.4 millimeters and about 19.2 millimeters in diameter. Most preferably, the atraumatic ball is about 12.7 millimeters in diameter.

Figure 4C:
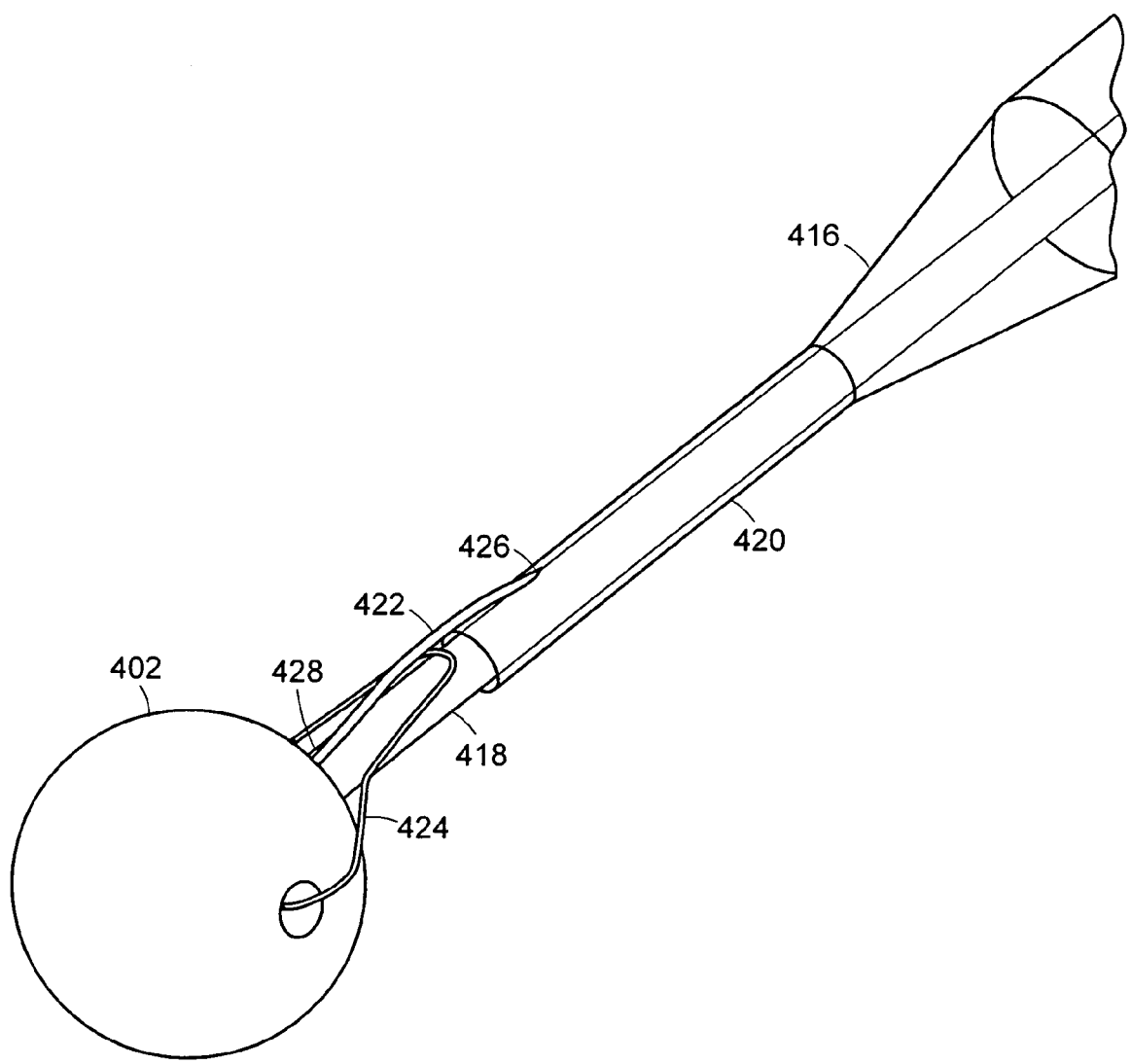

FIG. 4C shows a schematic diagram of the advanced atraumatic tip and distal end 418 of system 400 illustrated in FIG. 4B. Atraumatic ball 402 is secured to ball retaining wire 424. Ball locking wire 422 emerges from a locking wire lumen defined by inner catheter 410 at ball locking wire port 426, extends across a length of inner catheter 410, and passes into the locking wire lumen through ball locking wire port 428. The portion of locking wire 422 that extends between locking wire ports 426 and 428 passes through one or more perforations in distal portion 420 of sleeve 416 as well as through ball retaining wire 424, thereby removably securing both distal portion 420 and atraumatic ball 402 to distal end 418 of inner catheter 410.

Figure 4D:
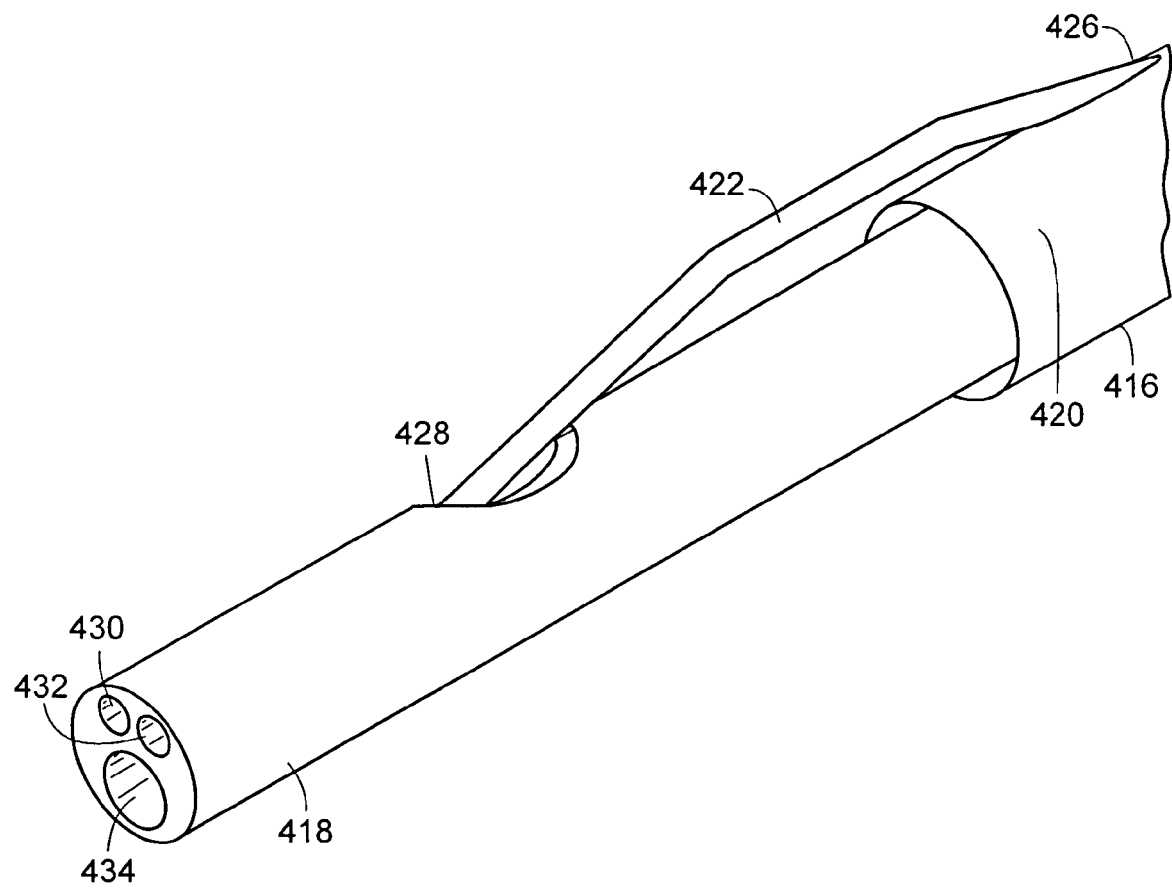

FIG. 4D illustrates a schematic view of distal end 418 of inner catheter 410 of system 400 with atraumatic ball 402 and retaining wire 424 omitted for clarity. Inner catheter 410 defines ball locking wire lumen 430, stiffening wire lumen 434, and tension wire lumen 432. Ball locking wire 422 exits ball locking wire lumen via locking wire port 426, extends through distal portion 420 of sleeve 416, and passes back into ball locking wire lumen 430 through locking wire port 428.

Figure 4E:
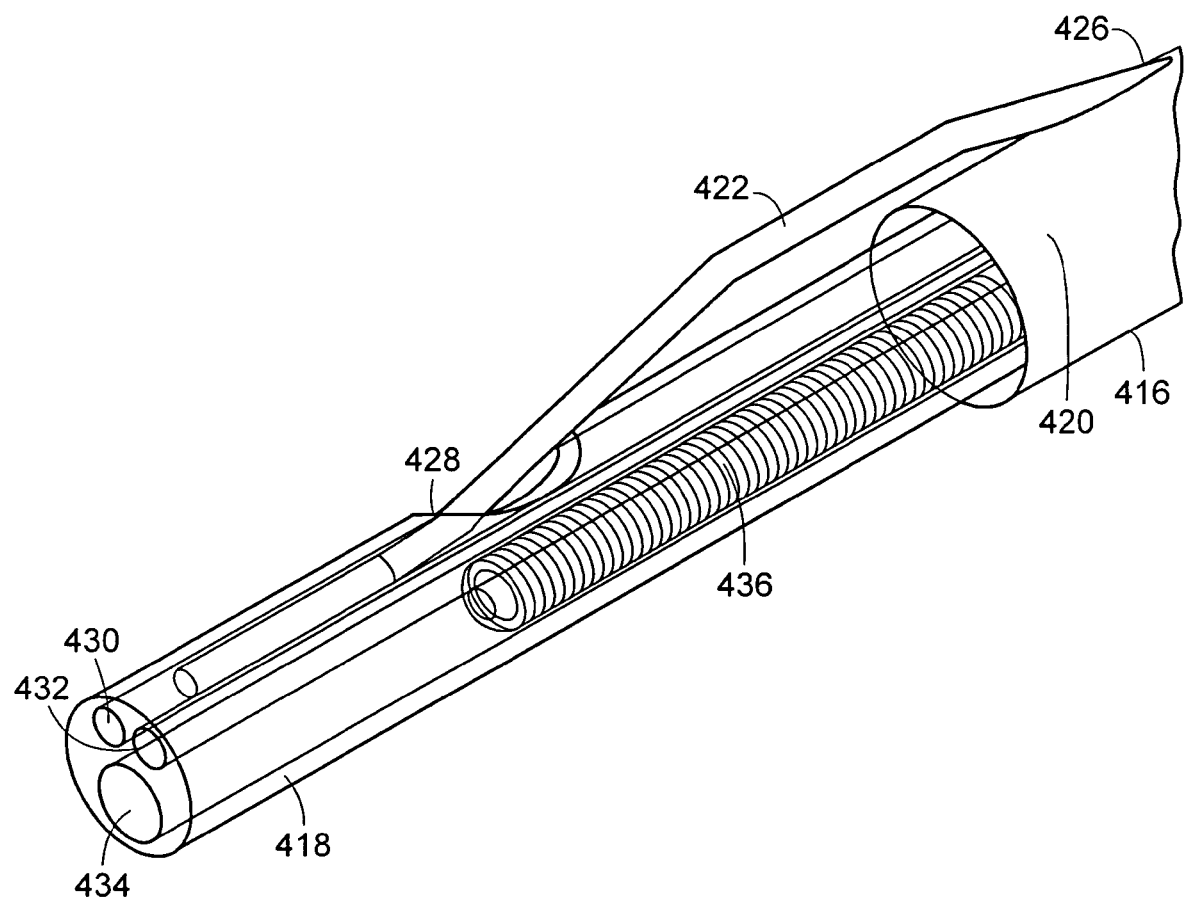

FIG. 4E illustrates a cut-away view of the schematic shown in FIG. 4D. Stiffening wire 436 lies within stiffening wire lumen 434. Stiffening wire 436 facilitates the advancement of the inner catheter through the gastrointestinal tract (e.g., through the proximal intestines) by, for example, providing a desirable amount of rigidity to the inner catheter so that it can negotiate the gastrointestinal tract. In further embodiments, the stiffening wire includes a distal portion that is less rigid than other, more proximal, portions. Inclusion of such a stiffening wire provides an inner catheter that has a distal portion that is less rigid than other, more proximal, portions. In some embodiments of the invention, the stiffening wire is used to eject the releasable ball from the end of the inner catheter by advancing the stiffening wire distally relative to the inner catheter. Optionally, the practitioner of the invention can remove the stiffening wire prior to removal of the inner and/or outer catheters, thereby reducing the rigidity of the inner catheter.

Inner catheter 410 defines tension wire lumen 432. The tension wire provides structural support to inner catheter 410 to prevent unwanted deformations of catheter 410 during insertion or maneuverings within a gastrointestinal tract. For example, the tension wire can be included to prevent inner catheter 410 from elongating or stretching. Such elongating or stretching can cause locking wire 422 to emerge from port 428 prematurely, thereby releasing distal ball 402 and distal portion 420 from distal end 418 at undesirable portions of a placement procedure.

Figure 4F:
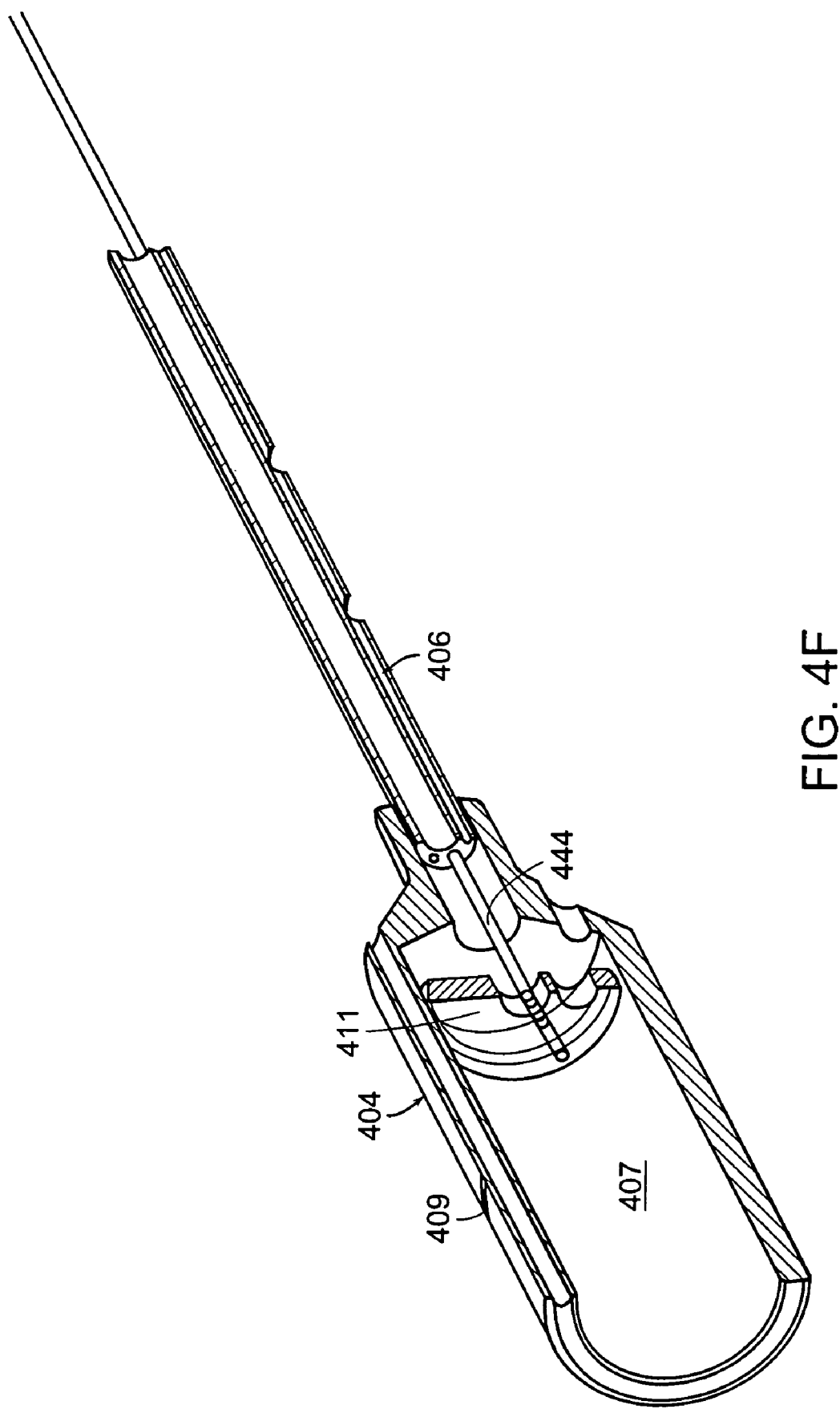

FIGS. 4F-5H illustrate additional embodiments of the invention that include cross sectional views of a portion of container 404. As illustrated in FIG. 4F, container 404 defines storage chamber 407. Container 404 includes visual marker 409 which can be used to determine if container 404 is in a desired location before an anchor is fully expelled from container 404. (FIGS. 2Q-2S illustrate how a practitioner of the invention uses a visual marker to determine if the container is in a desired location before an anchor is fully removed from the container.)

Figure 4G:
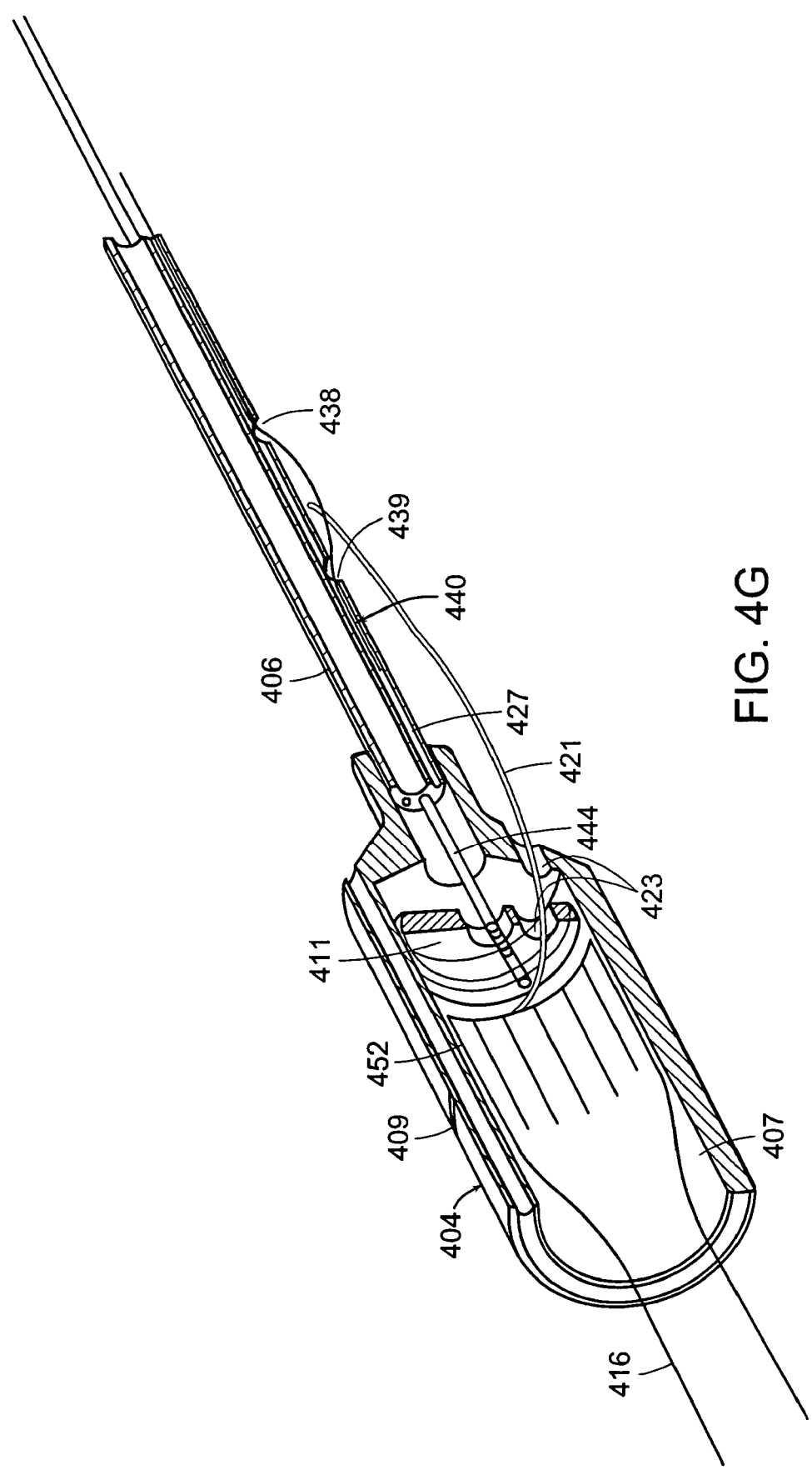
Figure 4H:
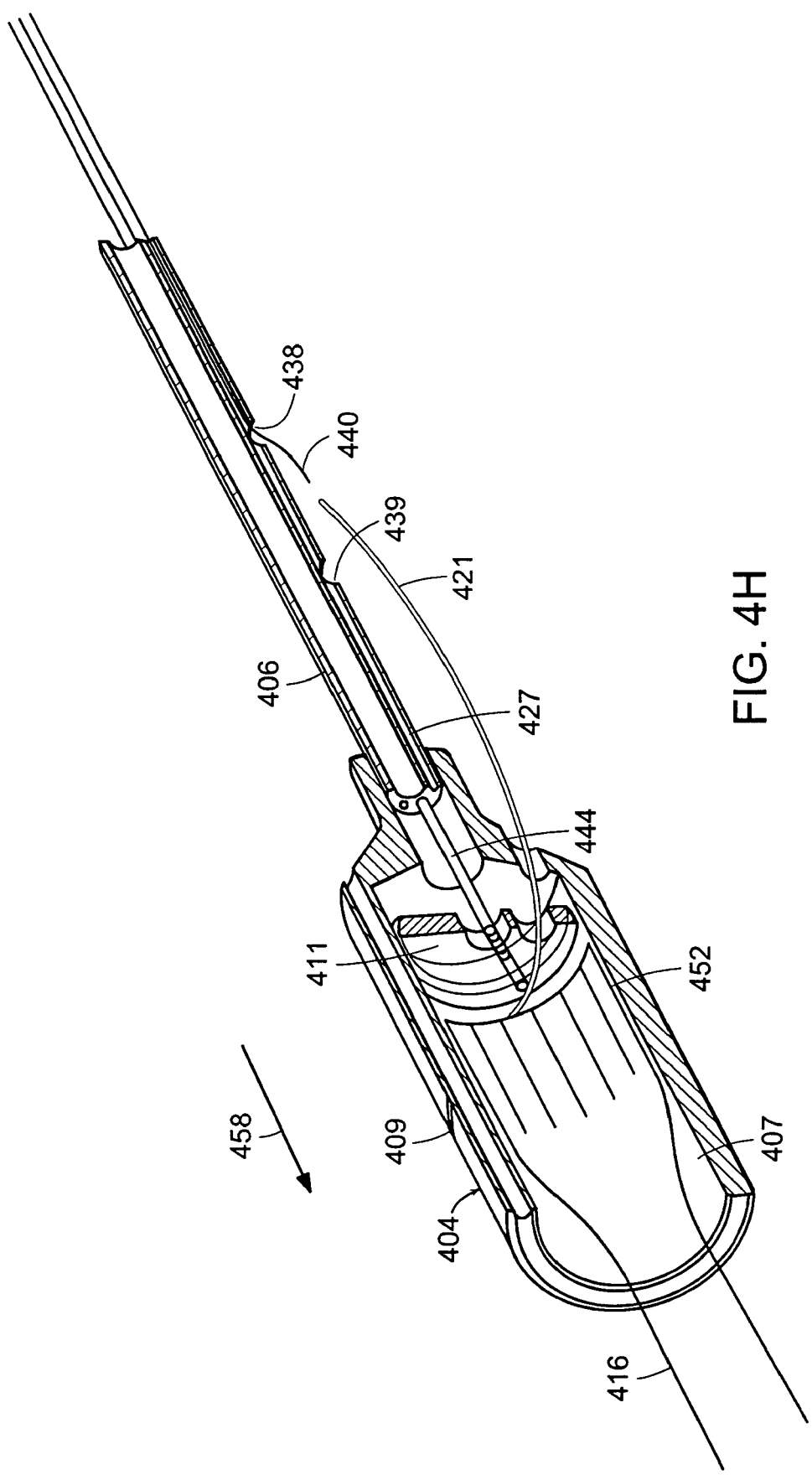
Figure 41:
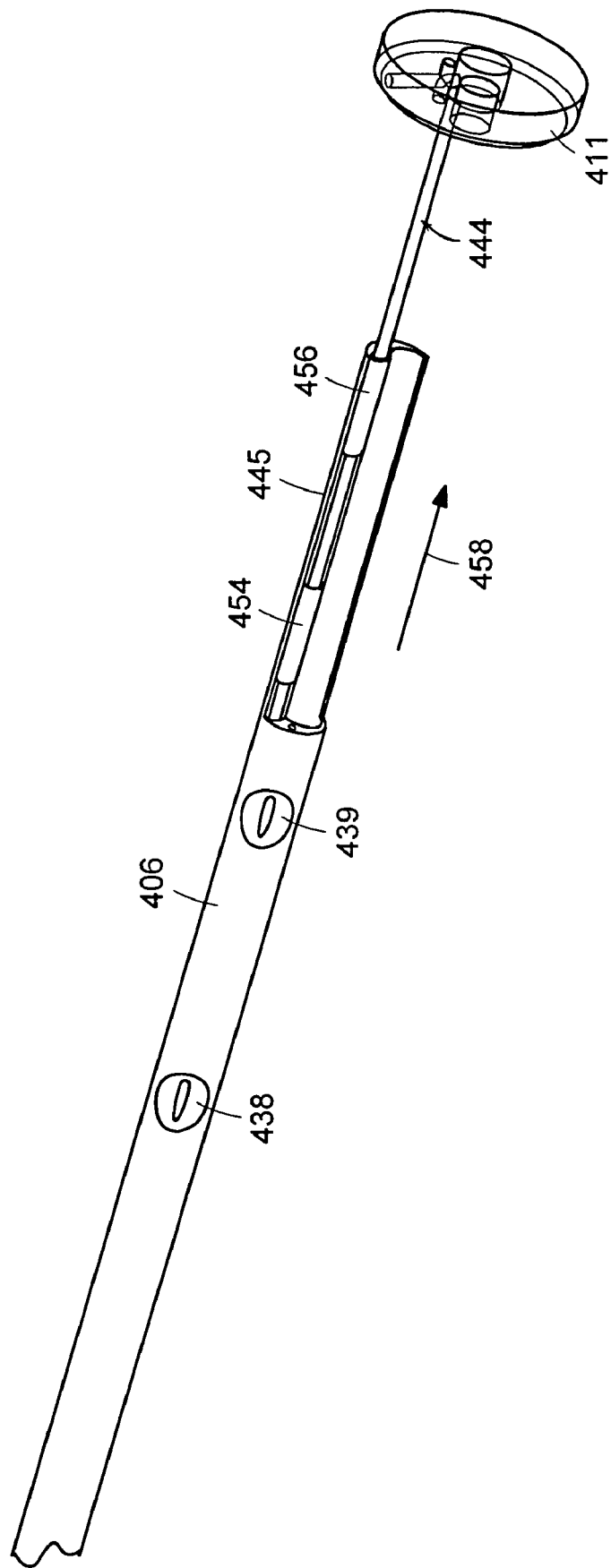

Container 404 is attached or assembled to outer catheter 406 (a portion of which is omitted from FIGS. 4F-4H for clarity). Anchor pusher wire 444 extends through an anchor pusher wire lumen which is defined by outer catheter 406. The distal end of anchor pusher wire 444 is attached or assembled to anchor pusher plate 411.

FIG. 4G illustrate container 404 and a stored portion of a gastrointestinal device that includes anchor 452 and a proximal portion of sleeve 416. Anchor 452 is collapsed or contracted and stored within chamber 407. In some embodiments, the anchor stored within the chamber(s) defined by a container assembly is a self-expanding anchor. Anchor 452 is contained or stored in container 404 during portions of a placement method that include directing the container assembly and portions of the gastrointestinal device to various locations within a gastrointestinal tract of a mammal. (FIGS. 2H-2P illustrate portions of a placement method that include directing a container assembly and portions of a gastrointestinal device to various locations within a gastrointestinal tract of a mammal.)

The proximal end of the gastrointestinal device includes one or more drawstrings which are attached to the proximal end of the device via perforations in the sleeve material. In some embodiments, one or more of these drawstrings are used to releasably secure or lock anchor 452 within container 404. For example, anchor retaining wire 421 extends out of the proximal end of container 404 via anchor retaining wire port 423 defined by anchor pusher plate 411 and container 404. Anchor locking wire 440 extends through anchor locking wire lumen 427 which is defined by outer catheter 406. Wire 440 emerges from lumen 427 via anchor locking wire port 438, extends through drawstring 421, and extends back into lumen 427 via anchor locking wire port 439.

After sleeve 416 has been deployed to a desired extent and container 404 is in the desired location, anchor 452 and the proximal portion of sleeve 416 can be released from container 404. FIG. 4H illustrates the release of anchor 452 from container 404. Anchor locking wire 440 is pulled proximally at anchor locking wire port 438 on the proximal end of outer catheter 406 (not illustrated in FIG. 4H), thereby pulling the distal portion of wire 440 from anchor locking wire port 439 and disengaging wire 440 from anchor retaining wire 421.

Once anchor 452 has been released from anchor locking wire 440, anchor 452 and proximal portion of sleeve 416 are expelled from container 404. To expel anchor 452 and the proximal portion of sleeve 416, a practitioner pushes anchor pusher wire 444 distally, thereby directing plate 411 along a direction parallel to direction 458 and forcing anchor 452 from the distal end of container 404. Optionally, or in addition, inner catheter 410 is advanced further, thereby causing distal portion 420 of sleeve 416 and the attached anchor 452 to advance distally relative to container 404 until anchor 452 emerges from container 404. In some embodiments, one or more of the chambers of the container assembly is lined with a layer of metal or metal alloy, thereby preventing portions of the anchor from adhering to the inner container walls and facilitating removal of the anchor from the container assembly. FIGS. 2Q-2R illustrate an anchor emerging from a container assembly.

FIG. 4I illustrates another view of pusher plate 411, omitting container 404 and portions of outer catheter 406 for clarity. Pusher plate wire 444 and pusher plate wire lumen 445 includes a mechanism to prevent a practitioner of the invention from directing plate 411 distally to such an extent that plate 411 emerges from the distal end of container 404. The mechanism includes moving stop 454 and static stop 456 which have dissimilar diameters. The dissimilar diameters prevent moving stop 454 from translating past static stop 456, thereby preventing excess distal translation of wire 444 relative to outer catheter 406.

Moving stop 454 is attached to, or formed by a portion of, wire 444 and has an outer diameter that is greater than the outer diameter of the portions of wire 444 that are distal from stop 454. Moving stop 454 moves or translates with wire 444 relative to outer catheter 406 along a direction that is parallel to direction 458.

Static stop 456 is attached to, or formed by a portion of, outer catheter 406. Stop 456 remains stationary with respect to catheter 406 as wire 444 is translated distally. Static stop 456 defines an inner diameter that is less than the diameter of moving stop 454 but greater than the diameter of the portion of wire 444 that is distal to moving stop 454. Hence, when wire 444 is sufficiently translated distally along a direction parallel to direction 458, moving stop 454 contacts static stop 456, thereby preventing further distal translation of wire 444 along a direction parallel to direction 458. In this manner, the mechanism allows a practitioner of the invention to sufficiently translate plate 411 distally so as to expel a gastrointestinal implant device from a container while simultaneously preventing plate 411 from emerging form the distal end of the container.

Figure 4J:
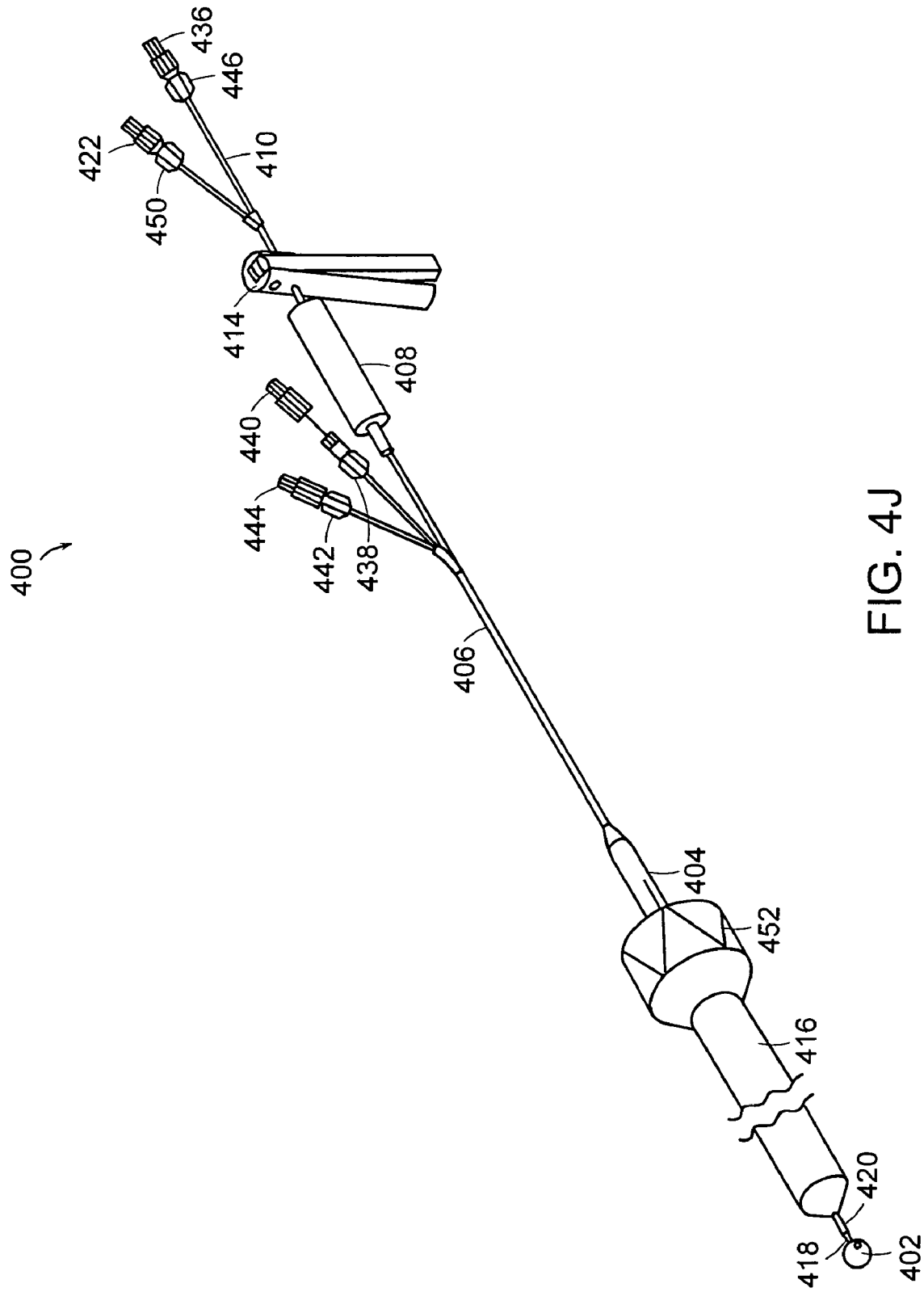

After anchor 452 is free of container 405, anchor 452 expands and is secured to a desired location within the gastrointestinal tract. FIG. 4J illustrates system 400 after anchor portion 452 has been expelled from container assembly 404. Anchor locking wire 440 has been pulled proximally and away from anchor locking wire port 438 and anchor 452 has expanded after leaving container 404. Anchor 452 secures the gastrointestinal device at a desired location within the gastrointestinal tract of a mammal.

Figure 4K:
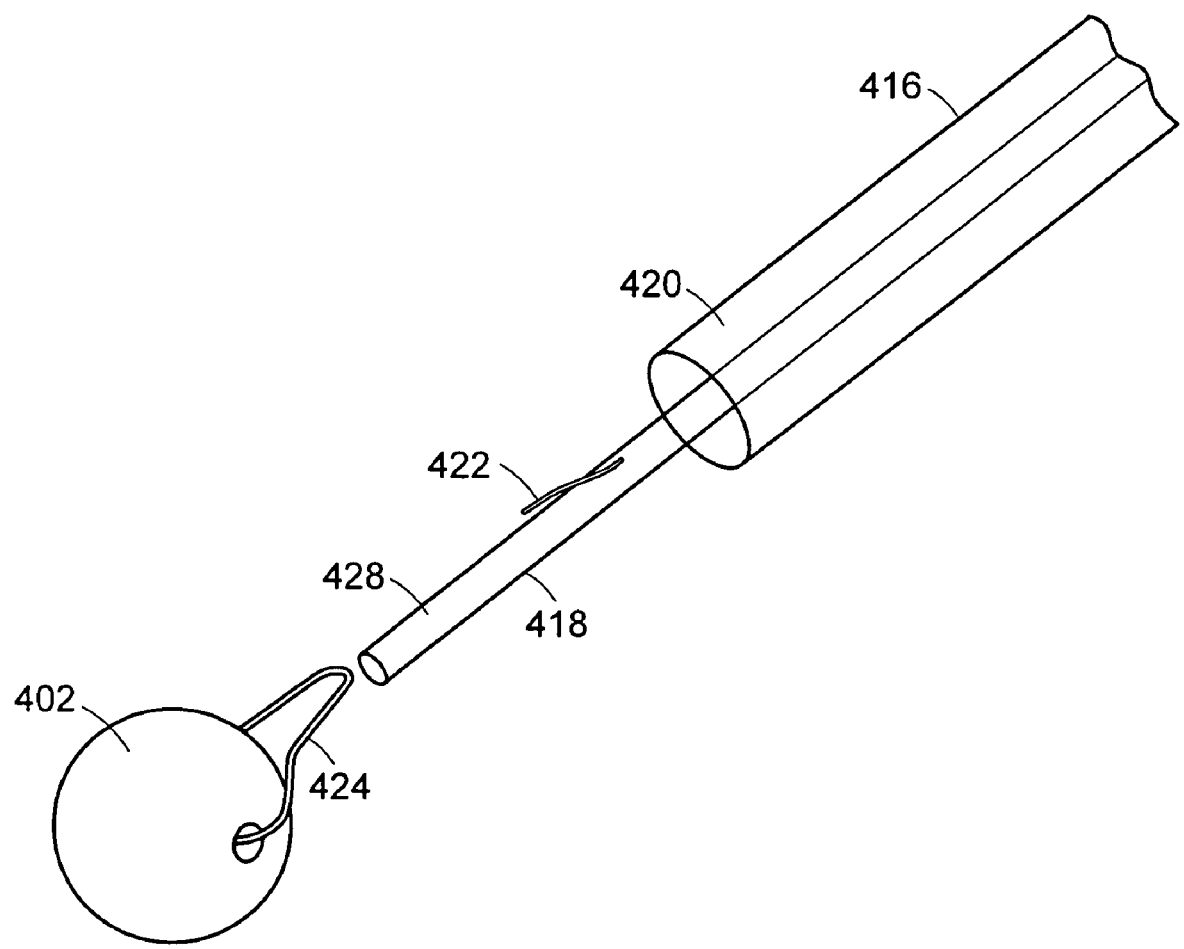

After anchor 452 has been deployed, distal portion 420 of sleeve 416 and ball 402 can be released from distal end 418 of inner catheter 410. FIG. 4K illustrates the release of ball 402 and distal portion 420 of sleeve 416. Ball locking wire 422 is pulled proximally at ball locking wire port 450, thereby pulling the distal portion of ball locking wire 422 from ball locking wire port 428 and disengaging ball locking wire 422 from ball retaining wire 424 and the perforation(s) on distal portion 420 of sleeve 416. Ball 402 disengages distal end 418 of inner catheter 410 and is passed through the remainder of the gastrointestinal tract by natural peristalsis.

Figure 4L:
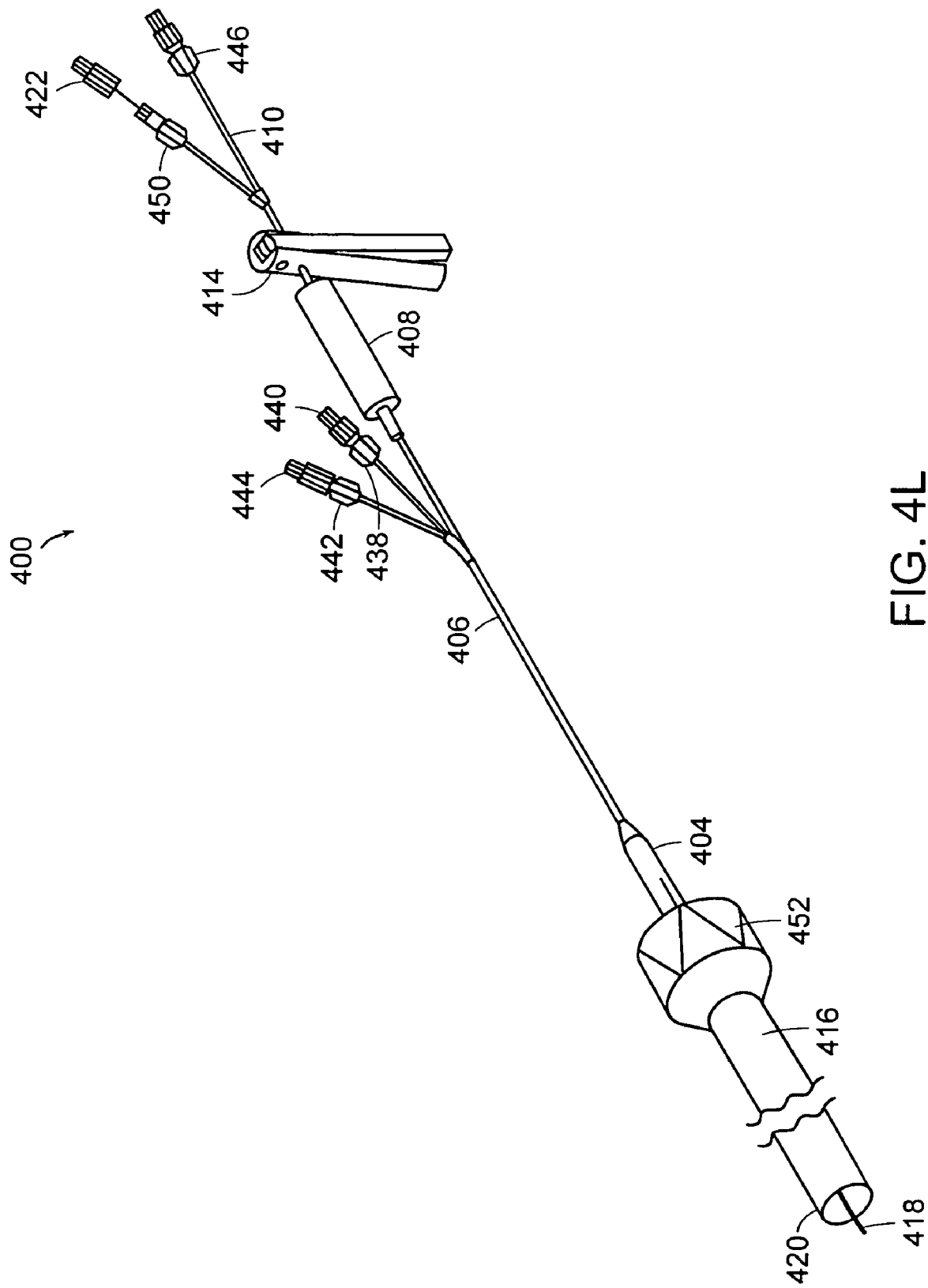

Optionally, a fluid (e.g., a gas or liquid) is directed into the gastrointestinal sleeve after the anchor has been deployed. At such a point in a placement process, stiffening wire 436 is no longer needed and can be removed from system 400 by pulling wire 436 proximally at stiffening wire port 446, and removing it entirely from stiffening wire lumen 434. Optionally, a fluid can then be directed through lumen 434 and into sleeve 416, thereby expanding at least a portion of sleeve 416. FIG. 4L illustrates system 400 after stiffening wire 436 has been removed and a fluid has been directed through stiffening wire port 446, through stiffening wire lumen 434, and into sleeve 416. Distal portion 420 of sleeve 416 has been expanded. Ball locking wire 422 has been pulled proximally from ball locking wire port 450. FIGS. 2T and 2U illustrates the release of a ball tip from an inner catheter.

Figure 5:
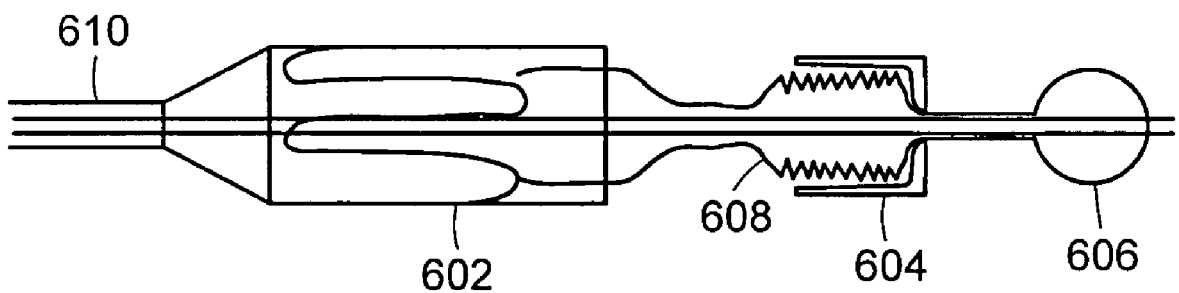
FIG. 5 illustrates an embodiment of a two-capsule delivery device that includes a first container, a second container, an atraumatic ball, and a sleeve of a gastrointestinal implant device.

In some embodiments of this invention, two capsules or containers are used to deliver or place a gastrointestinal device into a mammal. FIG. 5 illustrates one embodiment of a two-capsule delivery device that includes first container 602, second container 604, atraumatic ball 606, and sleeve 608 of a gastrointestinal implant device. A proximal portion of the gastrointestinal implant device, which includes an anchor, is stored in first container 602. A distal portion of the device, which includes sleeve 608, is stored within second container 604. Second container 604 or a portion of second container 604 fits coaxially inside of first container 602. Such a two-capsule embodiment is useful for reducing the amount of drag experienced when extending the sleeve portion of a gastrointestinal device through the distal intestines. This is because second container 604 is moving relative to the intestinal wall, while the portion of the sleeve that has been extended is relatively stationary with respect to the intestinal wall. In other words, rather than dragging the entire length of the extended sleeve material along the intestinal tract, essentially only second container 604 is moved relative to the intestinal wall. This reduces the amount of friction experienced when a practitioner of the invention extends the sleeve portion during a placement procedure of the invention.

Before insertion into a mammalian body, the distal end of sleeve 608 is secured or fastened inside of second container 604, while the anchor is secured or fastened within first container 602. A portion of the sleeve is also bundled into second container 604. Second container 604, including sleeve 608 is then placed inside of first container 602. First container 602 is attached to outer catheter 610 and inserted into the proximal duodenum. Second container 604 is attached to the distal end of the inner catheter. Second container 604 is advanced into the distal intestine along with the distal end of inner catheter and atraumatic ball 606. As second container 604 is advanced, sleeve 608 is released from the proximal end of second container 604. Once the distal end of the inner catheter is advanced to the desired location in the distal intestines, the distal end of sleeve 608 is unlocked from the first container. The anchor is then released from first container 602 and the device is secured within the gastrointestinal tract. The second container and atraumatic ball are passed through the digestive tract via natural peristalsis. Optionally, the second container and the atraumatic ball are formed from a single piece of material.

Figure 6:
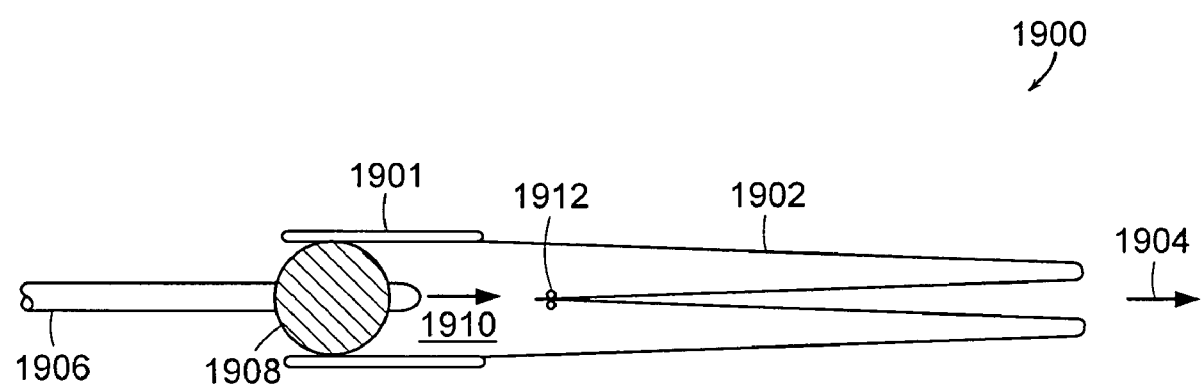
FIG. 6 illustrates a cross-section of an everting catheter system for delivery of a sleeve.

FIG. 6 is a cross-section of everting catheter system 1900 for delivery of a longer unsupported flexible sleeve 1902. A gastrointestinal implant device is shown with sleeve anchor 1901 and attached sleeve 1902 shown as delivered into the anatomy. The delivery catheter previously described is then removed. Balloon catheter 1906 is introduced into sleeve anchor 1901 and balloon 1908 inflated to seal the lumen of anchor 1901. Sleeve 1902 is folded inside itself and elastic band 1912 is used to seal the end of the sleeve. Fluid is then injected through balloon catheter shaft 1906 into sleeve lumen 1910, filling the lumen and pressurizing it. The pressure of the fluid is used to push the inner sleeve distally towards 1904. When sleeve 1902 has fully deployed distally, elastic band 1912 falls off of the closed end of sleeve 1902 and passes distally in the intestine until it is excreted. This mechanism permits deployment of a sleeve that is longer than (e.g., double) the length of the delivered device. This may be needed as it is difficult to access the distal parts of the intestine with guidewires. Generally, everting catheter system 1900 enables delivery of longer sleeves than are possible using some of the other delivery catheters described herein.

Figure 7B:
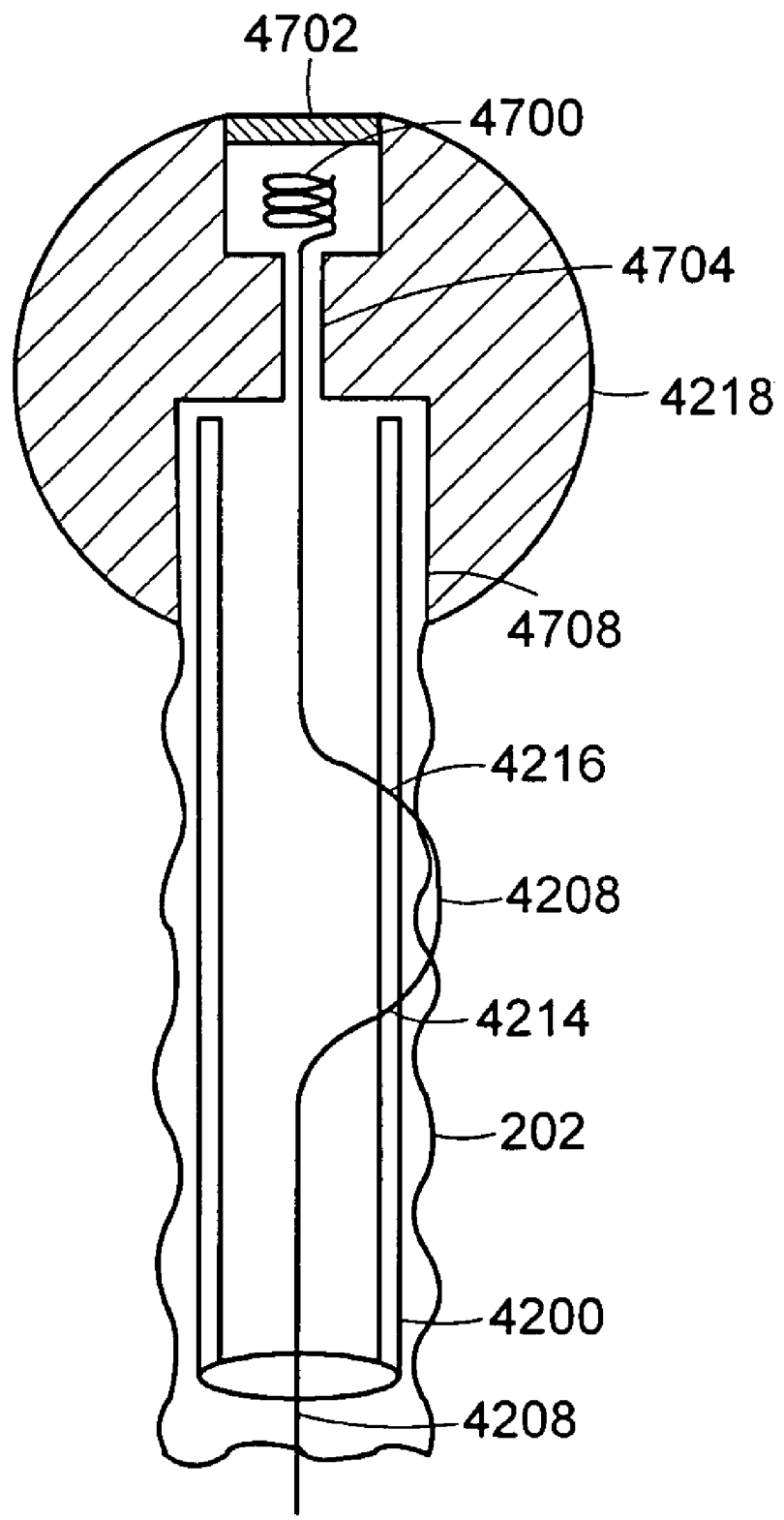
Figure 7C:
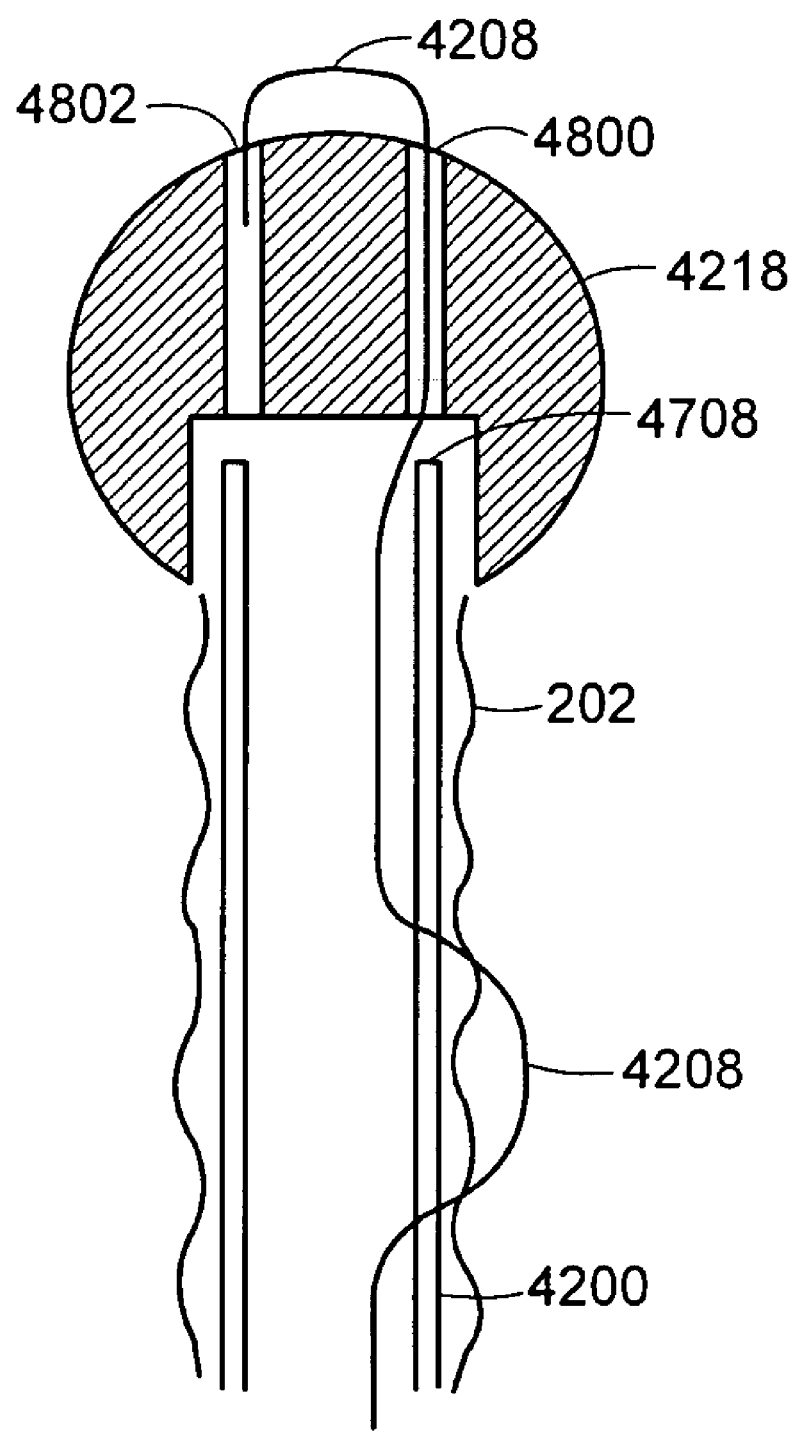

FIGS. 7A-7C illustrate embodiments for attaching a releasable atraumatic element to the distal end of a delivery catheter. FIG. 7A is a schematic view of the distal end of the catheter system illustrating a releasable ball tip mechanism. A sleeve retention wire 4208 travels through second lumen 4204 in catheter shaft 4200, exits second lumen 4204 through proximal skive hold 4218 and re-enters the second lumen through distal skive hole 4216.

The ends of a wire, or thread 4600 are attached to ball 4218 and thread 4600 is looped through sleeve retention wire 4208 to hold ball 4218 at the distal end of inner shaft 4200 of the catheter. Ball 4218 is released by pulling back on sleeve retention wire 4208 with fitting 4200 (FIG. 7A) until thread 4600 is no longer held by sleeve retention wire 4208. Ball 4218 then falls off the distal end of the inner shaft of catheter 4200 and exits the body through normal peristalsis through the intestines.

FIG. 7B is a schematic view of the distal end of the catheter illustrating an alternative embodiment of a releasable ball tip mechanism. Inner shaft 4200 fits in recess 4706 in ball 4218. Sleeve retention wire 4208 exits inner shaft 4200 through proximal skive hole 4214, pierces the sleeve and re-enters inner shaft 4200 through distal proximal skive hole 4216. The distal end of sleeve retention wire 4208 is formed into coil shape 4700 and sits in pocket 4702 in ball 4218. Pocket 4702 is connected to recess 4702 through hole 4704, which is of a smaller diameter than recess 4702 and pocket 4700. The distal end of sleeve retention wire 4208 can include a shape memory metal or metal alloy so that sleeve retention wire 4208 can be deformed and still return to approximately its original shape. In this way, wire 4208 can be assemble wire 4208 to ball 4218 and then the distal end of wire 4208 can regain its coiled shape to hold ball 4218 to the end of shaft 4200. Furthermore, wire 4208 can be can be pulled back in a proximal direction, the distal end of wire 4208 will straighten (thereby allowing the distal end of wire 4208 to be removed through hole 4704), and ball 4218 will be released from the end of shaft 4200.

FIG. 7C is yet another embodiment of a releasable ball tip mechanism. Inner shaft 4200 fits in recess 4706 in ball 4218. Sleeve retention wire 4208 exits inner shaft 4200 through proximal skive hole 4214, pierces the sleeve and re-enters the inner shaft 4200 through distal proximal skive hole 4216.

Ball 4218 includes two holes 4800, 4802 extending from recess 4706 to exterior surface of ball 4218. The distal end of sleeve retention wire 4208 passes through hole 166 and is looped back into hole 167. As sleeve retention wire 4208 is pulled proximally, wire 4218 is pulled back through hole 4802 and then through hold 4800 and ball 4218 is released from the distal end of the catheter.

Figure 8:
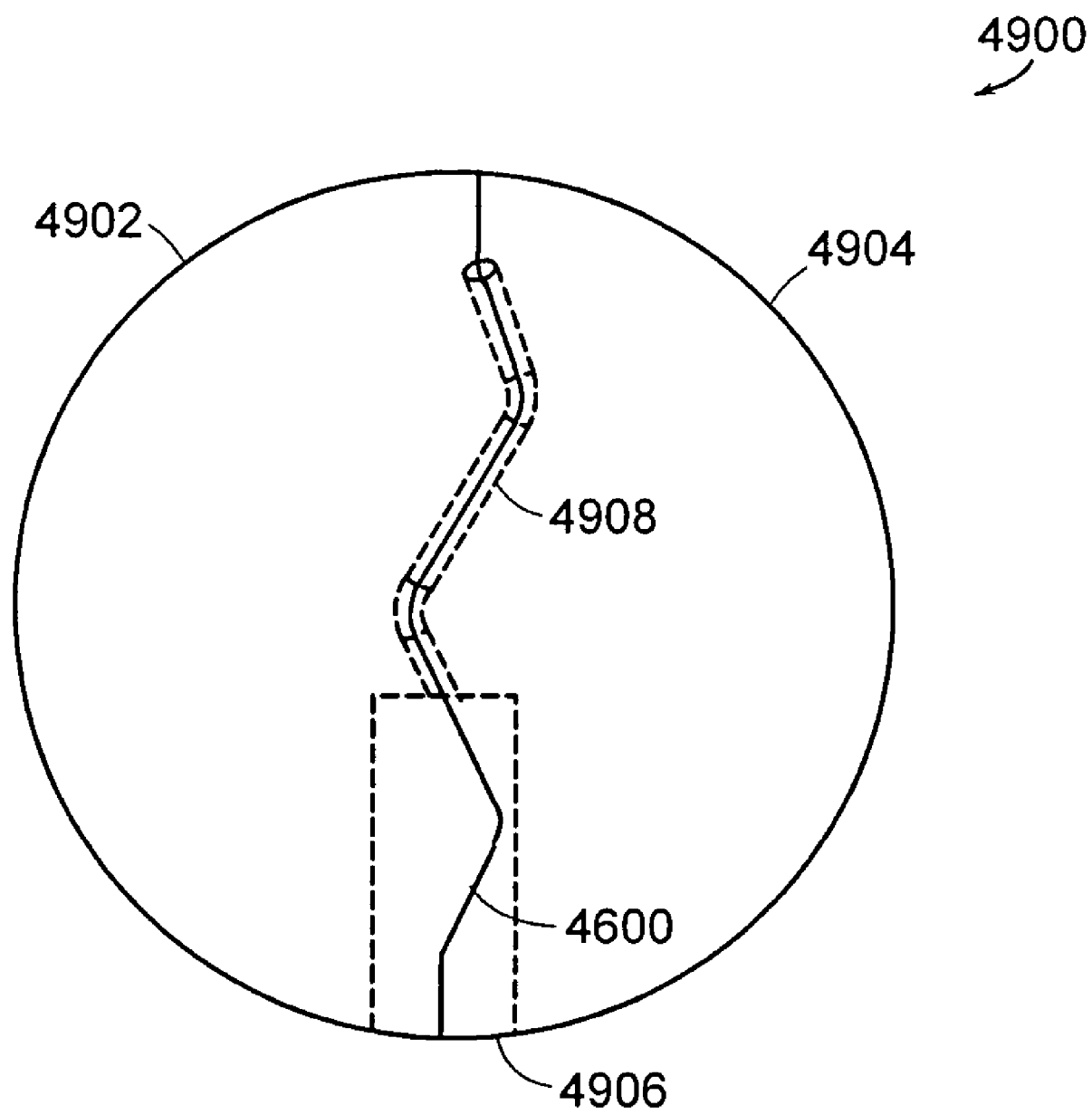
FIG. 8 illustrates a cross sectional view of an alternative embodiment of a solid spherical shaped atraumatic element.

FIG. 8 is a cross sectional view of an alternative embodiment of a solid spherical shaped atraumatic element. Ball 4900 is fabricated in two halves, 4902 and 4904. Sleeve retention wire 4006 fits into S-shaped track 4908. The S shape of track 4908 creates sufficient friction to hold the ball on the end of the catheter during delivery of the gastrointestinal implant device. Sleeve retention wire 4600 fits snugly in channel 4908 but can be pulled proximally to release sleeve retention wire 4600 from ball 4900. The catheter shaft fits in recess 4906.

Figure 9A:
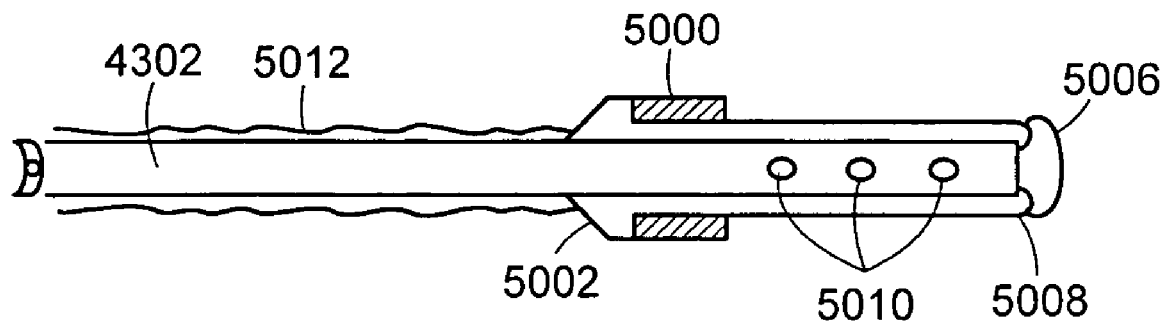
FIGS. 9A-9B illustrate sectional views of the distal ends of delivery catheters fitted with a low profile balloon.
Figure 9B:
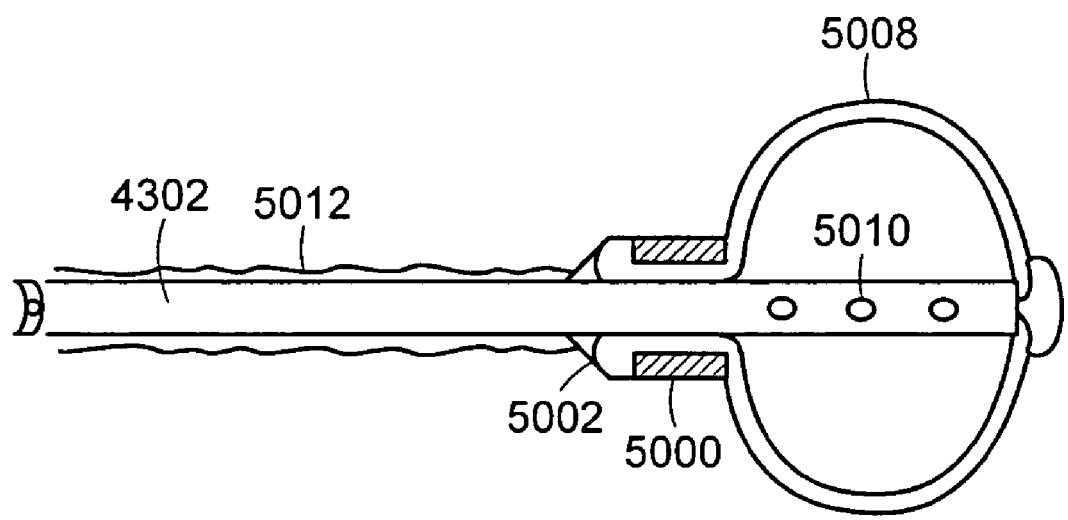

The distal end of a delivery catheter (e.g., an inner catheter) can includes an atraumatic tip comprising a low profile balloon instead of a releasable ball. FIGS. 9A-9B is a sectional view of the distal end of a delivery catheter fitted with a low profile balloon. FIG. 9A is a schematic view of the distal end of the catheter within an inflatable spherical shaped element. FIG. 9B is a schematic view of the distal end of the catheter after the inflatable spherical shaped element has been inflated;

Referring to FIG. 9A, sleeve 5012 is attached to the distal end of catheter shaft 4302. Filling holes 5010 connect with the inner lumen of the catheter to provide a passage for inflation of an inflatable spherical shaped element (balloon) 5008. Balloon 5008 is attached to shaft 4302 with metal band 5000 that has tapered proximal transition 5002 to minimize edges that could catch on sleeve 5012 after delivery of sleeve 5012. Metal band 5000 is about 0.003-0.005 inches (~0.076 to ~0.127 mm) thick. Balloon 5008 can be thin wall molded, tubular polyurethane or silicone. The balloon is stored along distal catheter shaft 4302 with the distal end pushed into the lumen of the catheter shaft and attached to catheter shaft 4302 with plug 5006 to keep the balloon from expanding beyond the tip of the catheter.

FIG. 9B illustrates the distal end of catheter 4302 after balloon 5002 has been expanded into a near-spherical shape. The balloon is expanded by fluid, which flows through the catheter shaft and enters balloon 5008 through the fluid passage holes from the catheter shaft. Plug 5006 at the end of the catheter shaft ensures that the balloon acts like the ball shown in the embodiment in FIG. 9B by limiting expansion of the balloon beyond the tip of the catheter, and the plug also provides some lateral strength to the balloon.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of placing a gastrointestinal implant device in a mammal, comprising the steps of:
    placing a gastrointestinal implant device in a container assembly, the implant device including an anchor and a floppy sleeve, the sleeve coupled to the anchor and folded into the container assembly;
    directing the container assembly, with the anchor and folded sleeve stored therein, into a mammalian gastrointestinal tract;
    removing at least a portion of the floppy sleeve from the container assembly by extending a portion of the floppy sleeve from the anchor and from container assembly to a location in the gastrointestinal tract that is distal relative to the assembly while the anchor is retained in the assembly; and
    subsequently removing the anchor from the container assembly and securing the anchor to a location in the gastrointestinal tract.

2. The method of claim 1, wherein the sleeve is extended to the location by advancing a catheter having an atraumatic tip.

3. The method of claim 2, wherein a distal portion of the catheter is less rigid than a proximal portion of the catheter.

4. The method of claim 1, wherein the assembly is directed to the duodenum of the gastrointestinal tract.

5. The method of claim 1, wherein at least a portion of the sleeve is directed into the jejunum of the gastrointestinal tract.

6. The method of claim 1, wherein the anchor is secured in the duodenum of the gastrointestinal tract.

7. The method of claim 1, wherein the anchor is self-expanding.

8. The method of claim 1, further including a step of directing a fluid into the gastrointestinal tract.

9. The method of claim 8, wherein the fluid is directed into the gastrointestinal tract before the assembly is directed into the duodenum.

10. The method of claim 8, wherein the fluid is directed into the gastrointestinal tract after the assembly is directed into the duodenum.

11. The method of claim 1, wherein the assembly includes a first chamber and the step of placing the device in the assembly includes storing the anchor in the first chamber.

12. The method of claim 11, wherein the step of removing the device from the assembly includes directing at least a portion of the floppy sleeve to a location in the gastrointestinal tract that is distal relative to the first chamber while the anchor is releasably secured in the first chamber.

13. The method of claim 11, wherein the assembly further includes a second chamber and the step of placing the device in the assembly includes storing at least a portion of the floppy sleeve in the second chamber.

14. The method of claim 13, wherein the step of removing the device from the assembly includes directing the second chamber to a location in the gastrointestinal tract that is distal relative to the first chamber while the anchor is releasably secured in the first chamber and the floppy sleeve is releasably secured in the second chamber.

15. The method of claim 1, wherein the portion of the floppy sleeve is extended by pulling the portion of the floppy sleeve with an extension that moves relative to the anchor.

16. The method of claim 1, wherein the anchor is retained in the assembly by an anchor lock as the portion of the floppy sleeve is extended.

17. A delivery system for placing a gastrointestinal implant device in a mammalian gastrointestinal tract comprising:
   a container assembly;
   a gastrointestinal implant device that includes a proximal end and a distal end stored within the container assembly, the proximal end including an anchor and the distal end including a floppy sleeve, coupled to the anchor and folded into the container assembly;
   a delivery extension configured to deliver the container assembly into the gastrointestinal tract with the anchor and floppy sleeve stored within the container assembly; and
   an inner extension to draw a portion of the sleeve from the anchor and from the container assembly as the anchor is retained therein.

18. The system of claim 17, further including an anchor locking mechanism located within the assembly.

19. The system of claim 18, wherein the anchor locking mechanism includes an anchor locking wire that extends through a portion of the device.

20. The system of claim 17, wherein the inner extension is a catheter releasably secured to the distal end of the sleeve.

21. The system of claim 20, wherein the catheter includes an atraumatic tip.

22. The system of claim 17, further including an anchor plunger for displacing the anchor from the container assembly.

23. The system of claim 17, wherein the anchor is self-expanding.

24. The system of claim 17, wherein the assembly includes a first chamber and a second chamber, the first chamber storing at least a portion of the proximal end and the second chamber storing at least a portion of the distal end.

25. The system of claim 24, wherein at least a portion of the second chamber is stored in the first chamber.

* * * * *